(12) United States Patent
Oost et al.

(10) Patent No.: US 9,006,276 B2
(45) Date of Patent: Apr. 14, 2015

(54) SUBSTITUTED OXINDOLE DERIVATIVES, MEDICAMENTS CONTAINING SAID DERIVATIVES AND USE THEREOF

(75) Inventors: Thorsten Oost, Biberach (DE); Wilfried Lubisch, Neckargemuend (DE); Wolfgang Wernet, Neustadt (DE); Wilfried Hornberger, Neustadt (DE); Liliane Unger, Ludwigshafen (DE); Herve Geneste, Neuhofen (DE); Astrid Netz, Mannheim (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 279 days.

(21) Appl. No.: 13/243,166

(22) Filed: Sep. 23, 2011

(65) Prior Publication Data
US 2013/0029966 A1    Jan. 31, 2013

Related U.S. Application Data

(62) Division of application No. 12/095,594, filed as application No. PCT/EP2006/069180 on Dec. 1, 2006, now Pat. No. 8,044,079.

(60) Provisional application No. 60/742,065, filed on Dec. 2, 2005.

(30) Foreign Application Priority Data

Dec. 2, 2005 (DE) .......................... 10 2005 059 484

(51) Int. Cl.
| | | |
|---|---|---|
| C07D 417/14 | (2006.01) |
| C07D 417/12 | (2006.01) |
| C07D 413/14 | (2006.01) |
| C07D 413/12 | (2006.01) |
| C07D 401/14 | (2006.01) |
| C07D 401/12 | (2006.01) |
| A61K 31/551 | (2006.01) |
| A61K 31/5377 | (2006.01) |
| A61K 31/496 | (2006.01) |
| A61K 31/4525 | (2006.01) |
| A61K 31/454 | (2006.01) |
| A61K 31/4439 | (2006.01) |
| A61K 31/427 | (2006.01) |
| A61K 31/422 | (2006.01) |

(52) U.S. Cl.
CPC .......... *C07D 401/14* (2013.01); *A61K 31/5377* (2013.01); *A61K 31/4439* (2013.01); *A61K 31/427* (2013.01); *C07D 401/12* (2013.01); *A61K 31/454* (2013.01); *A61K 31/422* (2013.01); *A61K 31/4525* (2013.01); *A61K 31/496* (2013.01); *A61K 31/551* (2013.01); *C07D 417/12* (2013.01); *C07D 413/12* (2013.01); *C07D 413/14* (2013.01); *C07D 417/14* (2013.01)

(58) Field of Classification Search
CPC .. C07D 417/14; C07D 417/12; C07D 413/14; C07D 413/12; C07D 401/14; C07D 401/12; A61K 31/551; A61K 31/5377; A61K 31/496; A61K 31/4525; A61K 31/454; A61K 31/4439; A61K 31/427; A61K 31/422
USPC ............ 514/374, 254.02, 210.21, 323, 235.2, 514/218, 365, 339, 253.09, 364; 540/575; 544/369, 137, 364; 546/201, 277.7; 548/235, 205, 131
See application file for complete search history.

(56) References Cited

U.S. PATENT DOCUMENTS

| | | | |
|---|---|---|---|
| 5,663,431 A | 9/1997 | Di Malta et al. |
| 5,773,612 A | 6/1998 | Wagnon et al. |
| 6,673,790 B1 | 1/2004 | Foulon |
| 7,803,834 B2 | 9/2010 | Oost et al. |
| 2003/0114683 A1 | 6/2003 | Roux et al. |

FOREIGN PATENT DOCUMENTS

| | | |
|---|---|---|
| FR | 2810320 | 6/2000 |
| WO | 93/15051 | 8/1993 |
| WO | 95/18105 | 6/1995 |
| WO | 98/25901 | 6/1998 |
| WO | 01/55130 | 8/2001 |
| WO | 01/55134 | 8/2001 |
| WO | 01/64668 | 9/2001 |
| WO | 01/98295 | 12/2001 |
| WO | 03/008407 | 1/2003 |
| WO | 2005/021534 | 3/2005 |
| WO | 2005/030755 | 4/2005 |

OTHER PUBLICATIONS

Oost et al. Bioorg. Med. Chem. Lett. 2011, 21, 3828-3831.*

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The invention relates to novel oxindole derivatives of general formula (I), wherein the substituents $R^1$, $R^2$, A, B, and Y are defined as in claim 1. The invention further relates to medicaments containing said derivatives, and use thereof for the prevention and/or treatment of vasopressin-dependent diseases.

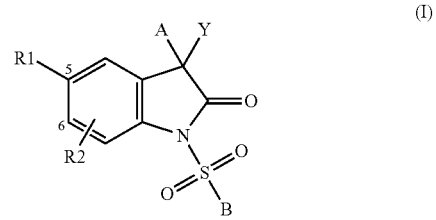

2 Claims, 1 Drawing Sheet

(56) References Cited

OTHER PUBLICATIONS

Greenberg et al. Kidney International, 2006, 69, 2124-2130.*
Robben et al. (J Am Soc Nephrol 18: 1534-1539, 2007.*
Mannucci, P.M. Treatment of Hemophilia, 2012, No. 11, 1-9.*
Koshimizu et al. Physiol. Rev. 2012. 92, 1813-1864.*
Holt et al. Journal of Cardiothoracic and Vascular Anesthesia, vol. 24, No. 2 Apr. 2010: pp. 330-347.*
Wersinger et al. Molecular Psychiatry 2002, 7, 975-984.*
Gal et al. CNS Drug Reviews, 2005, 11, 53-68.*
WebMD, Understanding Depression—Prevention, obtained from http://www.webmd.com/depression/guide/understanding-depression-prevention on Mar. 15, 2014.*
Serradeil-Le Gal et al., J. Pharm. Exp. Ther. (2002) 300:1122.
Griebel et al., Proc. Natl. Acad. Sci. (2002) 99:6370.
Thibonnier, M., Exp. Opin. Invest. Drugs. (1988) 7(5):729-740.
Notification of Transmittal of Translation of the International Preliminary Report on Patentability and translation of Written Opinion dated Jul. 17, 2008.

* cited by examiner

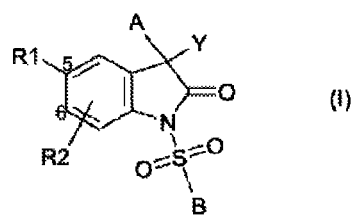
(1)

SUBSTITUTED OXINDOLE DERIVATIVES, MEDICAMENTS CONTAINING SAID DERIVATIVES AND USE THEREOF

CROSS-REFERENCE TO RELATED APPLICATIONS

This is a divisional of U.S. patent application Ser. No. 12/095,594, filed on Sep. 16, 2008, which is the U.S. national stage entry of International Patent Application No. PCT/EP2006/069180, filed on Dec. 1, 2006, which claims priority to U.S. Provisional Patent Application No. 60/742,065, filed on Dec. 2, 2005 and German Patent Application No. 102005059484.0, filed on Dec. 2, 2005, the contents of all of which are hereby incorporated by reference.

The present invention relates to novel substituted oxindole derivatives, medicaments containing same, and use thereof for the treatment of diseases.

Vasopressin (AVP) is an endogenous hormone which has various effects on organs and tissues. Vasopressin is related to oxytocin (OT), and therefore both peptides are combined into a vasopressin/oxytocin family. It is suspected that the vasopressin/oxytocin system plays a role in various medical conditions. Currently, three vasopressin receptors ($V1_a$, $V1_b$ or V3, and V2 receptors) and one oxytocin receptor (OT receptor) are known which mediate the effects of vasopressin and oxytocin. Antagonists of these receptors, in particular antagonists which bind specifically to only one of the above receptors, represent novel therapeutic approaches to the treatment of diseases (M. Thibonnier, Exp. Opin. Invest. Drugs 1998, 7(5), 729-740). For example, it has been found that a selective antagonist of the vasopressin V1 b receptor has anxiolytic and antidepressive effects in animal models (Griebel et al., PNAS 2002, 99, 6370; Serradeil-Le Gal et al., J. Pharm. Exp. Ther. 2002, 300, 1122). Since the described models have a certain predictive capability for the anticipated clinical effects, antagonists of the V1b receptor are of special interest for the treatment of emotional disorders or diseases, for example stress, anxiety states, and/or depression.

The present application describes novel substituted oxindoles which bear an arylsulfonyl group in the 1-position. 1-Phenylsulfonyl-1,3-dihydro-2H-indol-2-ones have previously been described as ligands for the vasopressin receptors. WO 93/15051, WO 95/18105, WO 98/25901, WO 01/55130, WO 01/55134, WO 01/064668, WO 01/98295, WO 05/021534 and WO 05/030755 describe compounds derived from the oxindole structure which bear an arylsulfonyl group in the 1-position. These compounds differ greatly in the substitution in the 3-position.

In particular in WO 93/15051 and WO 98/25901, 1-phenylsulfonyl-1,3-dihydro-2H-indol-2-ones are described as ligands for the vasopressin receptors in which the oxindole structure is substituted in the 3-position with two alkyl radicals, which likewise may be linked to a cycloalkyl radical (spiro linkage). Alternatively, the Spiro ring may contain heteroatoms such as oxygen and nitrogen (optionally with substituents).

WO 95/18105 describes 1-phenylsulfonyl-1,3-dihydro-2H-indol-2-ones as ligands for vasopressin receptors which bear a nitrogen substituent in the 3-position. Also bonded in the 3-position is a radical selected from alkyl, cycloalkyl, phenyl, and benzyl (each optionally containing substituents).

Other publications, for example WO 01/55130, describe compounds having rings containing nitrogen (for example, proline, homoproline, morpholine, tetrahydroisoquinoline, dihydroindole; each optionally containing substituents) which are bonded via their nitrogen atom in the 3-position of the oxindole structure, but substituted in both the 1-position and the 3-position on the oxindole ring with phenylsulfonyl or phenyl groups (optionally containing substituents).

WO 03/008407 describes 1-phenylsulfonyloxindoles in which pyridylpiperazines are bonded in the 3-position on the oxindole via an oxycarbonylgroup.

The object of the present invention is to provide further compounds for the treatment or prevention of various vasopressin-dependent diseases.

The compounds preferably have advantages compared to known compounds, such as for example improved metabolic stability and/or improved pharmacological activity. The advantages may be demonstrated, for example, by using suitable models which allow predictions to be made for the desired application in the treatment of patients.

BRIEF DESCRIPTION OF THE SEVERAL VIEWS OF THE DRAWINGS

FIG. 1 shows the general structure of the compound of general formula (I).

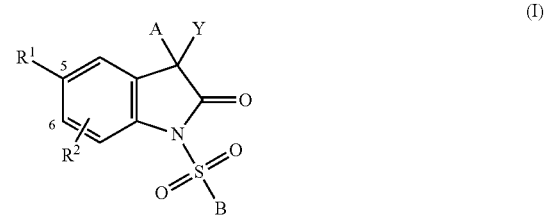

DESCRIPTION OF THE INVENTION

Surprisingly, it has been found that the stated object is achieved by use of compounds of general formula (I)

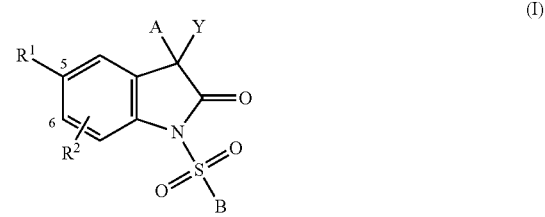

wherein

A is an aromatic, heteroaromatic, partially aromatic, or partially heteroaromatic mono- or bicyclic ring containing 1, 2, 3, 4, 5, 6, 7, 8, 9, or 10 carbon atoms as ring members, and the ring may also contain as ring members 0, 1, 2, 3, or 4 heteroatoms which are the same or different, independently selected from the group comprising nitrogen, oxygen, and sulfur, and which is substituted with the $R_A^1$ radical and which may also be substituted with one, two, or three $R_A^{11}$, $R_A^{12}$, and/or $R_A^{13}$ radicals which, independently of one another and independently of their respective occurrence, are selected from the group comprising bromine, chlorine, fluorine, CN, $CF_3$, $OCF_3$, $OCHF_2$, OH, O—$C_1$-$C_4$ alkyl, and $C_1$-$C_4$ alkyl;

$R_A^1$ is selected from the group comprising
$C_1$-$C_4$ alkylene-$R_A^2$, $C_0$-$C_3$ alkylene-O—$C_2$-$C_4$ alkylene-$R_A^2$, or $C_0$-$C_3$ alkylene-$NR_A^3$-$C_2$-$C_4$ alkylene-$R_A^2$;

$R_A^3$ is selected from the group comprising hydrogen and $C_1$-$C_4$ alkyl;

$R_A^2$ is selected from the group comprising
OH, $NH_2$, NH($C_1$-$C_4$ alkyl), N($C_1$-$C_4$ alkyl)($C_1$-$C_4$ alkyl), NH($C_2$-$C_4$ alkylene-OH), N($C_1$-$C_4$ alkyl)($C_2$-$C_4$ alkylene-OH), NH(C$_2$-C$_4$ alkylene-O—C$_1$-C$_4$ alkyl), N(C$_1$-C$_4$ alkyl)(C$_2$-C$_4$ alkylene-O—C$_1$-C$_4$ alkyl), NH(C$_3$-C$_7$ cycloalkyl), N(C$_1$-C$_4$ alkyl)(C$_3$-C$_7$ cycloalkyl), NH(C$_1$-C$_4$ haloalkyl), N(C$_1$-C$_4$ alkyl)(C$_1$-C$_4$ haloalkyl), and ring R$_A^4$;

R$_A^4$ independently of its respective occurrence is selected from the group comprising the particular individual radicals

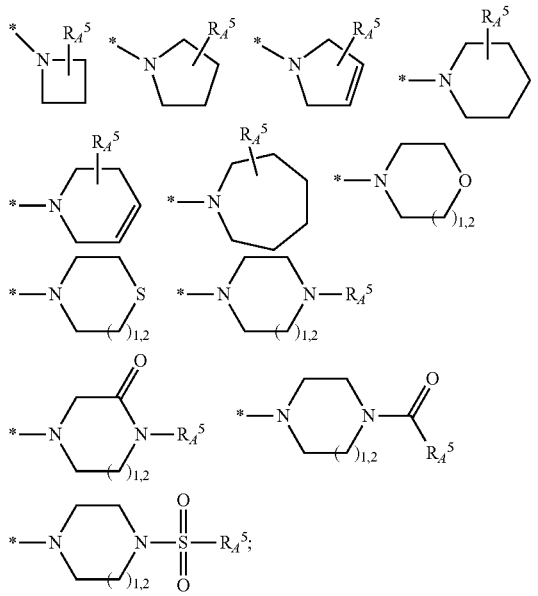

R$_A^5$ is selected from the group comprising hydrogen, hydroxy, and optionally substituted C$_1$-C$_4$ alkyl, such as hydroxy-C$_1$-C$_4$ alkyl, in particular hydrogen and C$_1$-C$_4$ alkyl;

B is an aromatic, heteroaromatic, partially aromatic, or partially heteroaromatic mono- or bicyclic ring containing 1, 2, 3, 4, 5, 6, 7, 8, 9, or 10 C atoms as ring members, and the ring may also contain as ring members 0, 1, 2, 3, or 4 heteroatoms which are the same or different, independently selected from the group comprising nitrogen, oxygen, and sulfur, and may be substituted with one, two, or three radicals R$_B^1$, R$_B^2$, and/or R$_B^3$ which, independently of one another and independently of their respective occurrence, are selected from the group comprising chlorine, bromine, fluorine, CN, CF$_3$, OCF$_3$, OCHF$_2$, OH, O—C$_1$-C$_4$ alkyl, and C$_1$-C$_4$ alkyl;

R$^1$ is selected from the group comprising hydrogen, bromine, chlorine, fluorine, iodine, CN, CF$_3$, OCF$_3$, OCHF$_2$, O—C$_1$-C$_4$ alkyl, C$_1$-C$_4$ alkyl, C$_1$-C$_4$ alkenyl, and C$_2$-C$_4$ alkynyl;

R$^2$ is selected from the group comprising hydrogen, C$_1$-C$_4$ alkyl, O—C$_1$-C$_4$ alkyl, chlorine, fluorine, and trifluoromethyl;

Y stands for a radical

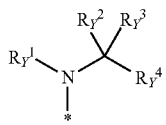

wherein
R$_Y^1$ is selected from the group comprising hydrogen and C$_1$-C$_4$ alkyl; and
R$_Y^2$ is selected from the group comprising hydrogen, phenyl, C$_1$-C$_6$ alkyl, and C$_3$-C$_7$ cycloalkyl, wherein R$_Y^1$ and R$_Y^2$ combined, together with the atom to which they are bonded, may also form a 4-, 5-, 6-, or 7-membered saturated or unsaturated carbocyclic ring containing a nitrogen atom, and the ring may contain one or two substituents R$_Y^6$ and/or R$_Y^7$ which, independently of one another and independently of their respective occurrence, are selected from the group comprising fluorine, OH, O-C$_1$-C$_4$ alkyl, phenyl, and C$_1$-C$_4$ alkyl; or when R$_Y^6$ and R$_Y^7$ occupy adjacent positions, R$_Y^6$ and R$_Y^7$ together with the respective C atom to which they are bonded may form a condensed substituted or unsubstituted benzene ring;

R$_Y^3$ is selected from the group comprising hydrogen and methyl;

R$_Y^4$ is a saturated, partially saturated, or unsaturated ring containing 1, 2, 3, 4, 5, or 6 C atoms as ring members, and the ring may also contain as ring members 1, 2, 3, or 4 heteroatoms which are the same or different, independently selected from the group comprising nitrogen, oxygen, and sulfur, and which may be substituted with one or two radicals R$_Y^8$ and/or R$_Y^9$, where R$_Y^8$ and R$_Y^9$ independently of one another and independently of their respective occurrence are selected from the group comprising chlorine, bromine, fluorine, CN, OH, O—C$_1$-C$_4$ alkyl, and C$_1$-C$_4$ alkyl;

and by tautomeric forms, prod rugs, and in particular physiologically tolerable salts of compounds of formula (I).

The subject matter of the invention, therefore, is compounds of formula (I), their tautomers, prodrugs, and in particular their physiologically tolerable salts.

One preferred embodiment of the present invention relates to compounds of general formula (I), as described above or in Claim 1, their tautomers, prod rugs, and physiologically tolerable salts, wherein the variables A, R$_A^1$, R$_A^2$, R$_A^3$, R$_A^4$, R$_A^5$, B, R$^1$, R$^2$, Y, R$_Y^1$, R$_Y^2$, R$_Y^3$, and R$_Y^4$ independently and preferably in combination have the following meanings:

A is a ring selected from the group comprising benzene, benzo[1,3]dioxol, thiophene, and pyridine, and is substituted with the R$_A^1$ radical and may also be substituted with one or two R$_A^{11}$ and/or R$_A^{12}$ radicals which independently of one another and independently of their respective occurrence are selected from the group comprising chlorine, fluorine, hydroxy, methoxy, ethoxy, propoxy, methyl, ethyl, and propyl;

R$_A^1$ is selected from the group comprising C$_1$-C$_4$ alkylene-R$_A^2$, O—C$_2$-C$_4$ alkylene-R$_A^2$, NR$_A^3$-C$_2$-C$_4$ alkylene-R$_A^2$, and CH$_2$—NR$_A^3$-C$_2$-C$_4$ alkylene-R$_A^2$;

R$_A^3$ is selected from the group comprising hydrogen and C$_1$-C$_4$ alkyl;

R$_A^2$ is selected from the group comprising
OH, NH$_2$, NH(C$_1$-C$_4$ alkyl), N(C$_1$-C$_4$ alkyl)(C$_1$-C$_4$ alkyl), NH(C$_2$-C$_4$ alkylene-OH), N(C$_1$-C$_4$ alkyl)(C$_2$-C$_4$ alkylene-OH), NH(C$_2$-C$_4$ alkylene-O—C$_1$-C$_4$ alkyl), N(C$_1$-C$_4$ alkyl)(C$_2$-C$_4$ alkylene-O—C$_1$-C$_4$ alkyl), and ring R$_A^4$;

R$_A^4$ independently of its respective occurrence is selected from the group comprising the particular individual radicals

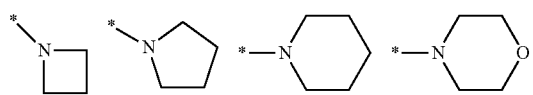

-continued

*—N◯N—R$_A^5$  *—N◯N—C(=O)R$_A^5$;

$R_A^5$ is selected from the group comprising hydrogen and $C_1$-$C_4$ alkyl;

B is an aromatic or heteroaromatic mono- or bicyclic ring containing 1, 2, 3, 4, 5, 6, 7, 8, 9, or 10 C atoms as ring members, and the ring may also contain as ring members 0, 1, 2, 3, or 4 heteroatoms which are the same or different, independently selected from the group comprising nitrogen, oxygen, and sulfur, and may be substituted with one or two radicals $R_B^1$ and/or $R_B^2$, wherein $R_B^1$ and $R_B^2$ are independently selected from the group comprising chlorine, fluorine, CN, OH, O—$C_1$-$C_4$ alkyl, and $C_1$-$C_4$ alkyl;

$R^1$ is selected from the group comprising hydrogen, chlorine, fluorine, CN, methoxy, and methyl;

$R^2$ is selected from the group comprising hydrogen, chlorine, fluorine, and methyl;

Y stands for a radical

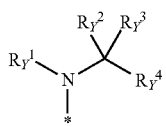

wherein $R_Y^1$ is selected from the group comprising hydrogen and $C_1$-$C_4$ alkyl; and $R_Y^2$ is selected from the group comprising hydrogen, phenyl, and $C_1$-$C_4$ alkyl;
wherein $R_Y^1$ and $R_Y^2$ combined, together with the respective atom to which they are bonded, may also form a 5- or 6-membered saturated or unsaturated carbocyclic ring containing a nitrogen atom, and the ring may contain a substituent $R_Y^6$ selected from the group comprising $C_1$-$C_4$ alkyl, O—$C_1$-$C_4$ alkyl, fluorine, and OH;

$R_Y^3$ is hydrogen;

$R_Y^4$ is a 5- or 6-membered heteroaromatic ring containing 1, 2, 3, 4, or 5 C atoms as ring members, and the ring may also contain as ring members 1, 2, 3, or 4 heteroatoms which are the same or different, and which are independently selected from the group comprising nitrogen, oxygen and sulfur, and may optionally be substituted with an $R_Y^8$ radical, wherein $R_Y^8$, independently of its occurrence, is selected from the group comprising $C_1$-$C_4$ alkyl.

The preferences described in this and subsequent embodiments with regard to the radicals A, $R_A^1$, $R_A^2$, $R_A^3$, $R_A^4$, $R_A^5$, B, $R^1$, $R^2$, Y, $R_Y^1$, $R_Y^2$, $R_Y^3$, and $R_Y^4$ apply independently of one another and with respect to the radicals considered separately, as well as in any given combination of the radicals. The preferences apply in particular with regard to all radicals in combination.

One particularly preferred embodiment relates to compounds of general formula (I), as described above or in Claim 1 or 2, wherein A is a benzene ring which is substituted with the $R_A^1$ radical and which may also be substituted with an $R_A^{11}$ radical;

$R_A^{11}$ is selected from the group comprising chlorine, fluorine, methoxy, ethoxy, propoxy, methyl, and ethyl;

$R_A^1$ is a radical selected from the group comprising the particular individual radicals

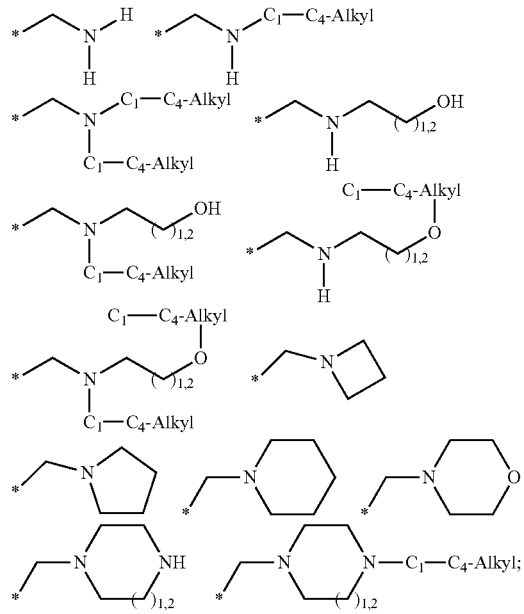

B is a ring selected from the group comprising benzene, pyridine, thiophene, and quinoline, and the ring may be substituted in each case with one or two radicals $R_B^1$ and/or $R_B^2$, wherein $R_B^1$ and $R_B^2$ are independently selected from the group comprising chlorine, fluorine, CN, methyl, ethyl, hydroxy, methoxy, and ethoxy;

$R^1$ is selected from the group comprising hydrogen, chlorine, fluorine, CN, methoxy, and methyl;

$R^2$ is selected from the group comprising hydrogen, chlorine, and fluorine;

Y is a radical selected from the group comprising the particular individual radicals

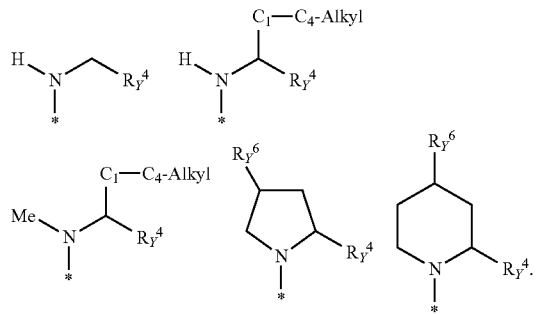

$R_Y^4$ is a radical selected from the group comprising pyridine, pyrimidine, pyrazine, pyridazine, furan, thiophene, pyrrole, oxazole, isoxazole, thiazole, imidazole, pyrazole, 1,2,4-oxadiazole, 1,2,5-oxadiazole, 1,3,4-oxadiazole, thiadiazole, triazole, 1,3,5-triazine, and tetrazole;

$R_Y^6$ is selected from the group comprising the radicals hydrogen, fluorine, and OH;

and tautomeric forms, prod rugs, and in particular physiologically tolerable salts of compounds of formula (I).

One preferred embodiment relates to compounds of general formula (I), as described above or in claim 1, wherein A is selected from the group comprising the particular individual radicals

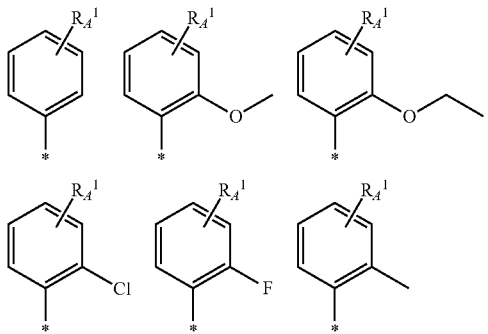

$R_A^1$ is a radical selected from the group comprising the particular individual radicals

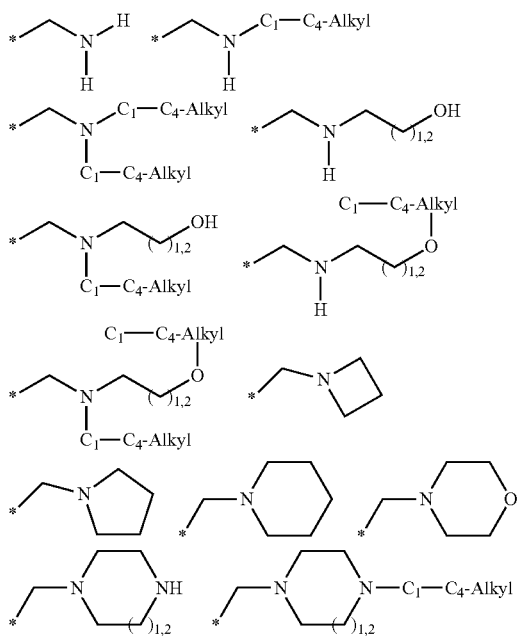

B is a ring selected from the group comprising the particular individual radicals

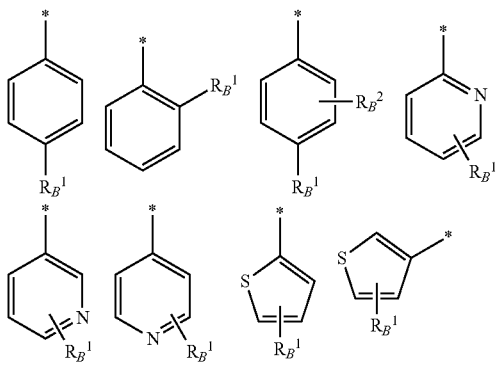

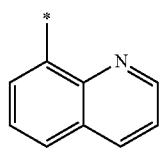

wherein
$R_B^1$ and $R_B^2$, independently of one another and independently of their respective occurrence, are selected from the group comprising hydrogen, chlorine, fluorine, CN, methyl, methoxy, and ethoxy;
$R^1$ is selected from the group comprising chlorine, fluorine, methoxy, and CN;
$R^2$ is selected from the group comprising hydrogen, chlorine, and fluorine;
Y is selected from the group comprising the particular individual radicals

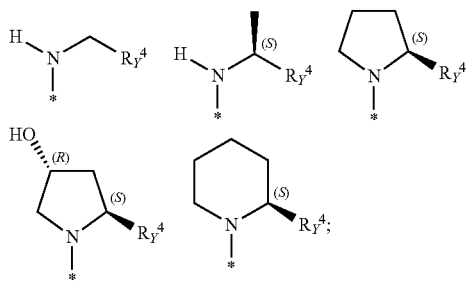

$R_Y^4$ is selected from the group comprising the particular individual radicals

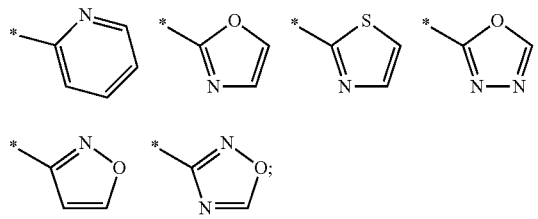

and tautomeric forms, prodrugs, and in particular physiologically tolerable salts of compounds of formula (I).

Also particularly preferred are mixtures of enantiomeric and diastereomeric forms of the compounds of formula (I) which include as a primary component compounds of formula (I) whose radicals Y have the stereochemistry shown here.

One particularly preferred embodiment relates to compounds of general formula (I) as described above or in claim 1, wherein
A is a radical selected from the group comprising the particular individual radicals

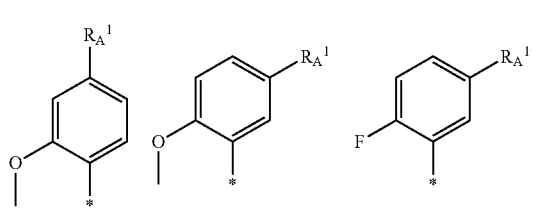

-continued

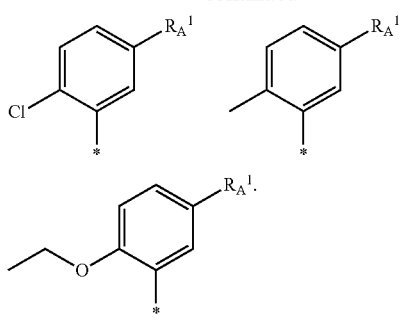

$R_A^1$ is a radical selected from the group comprising the particular individual radicals

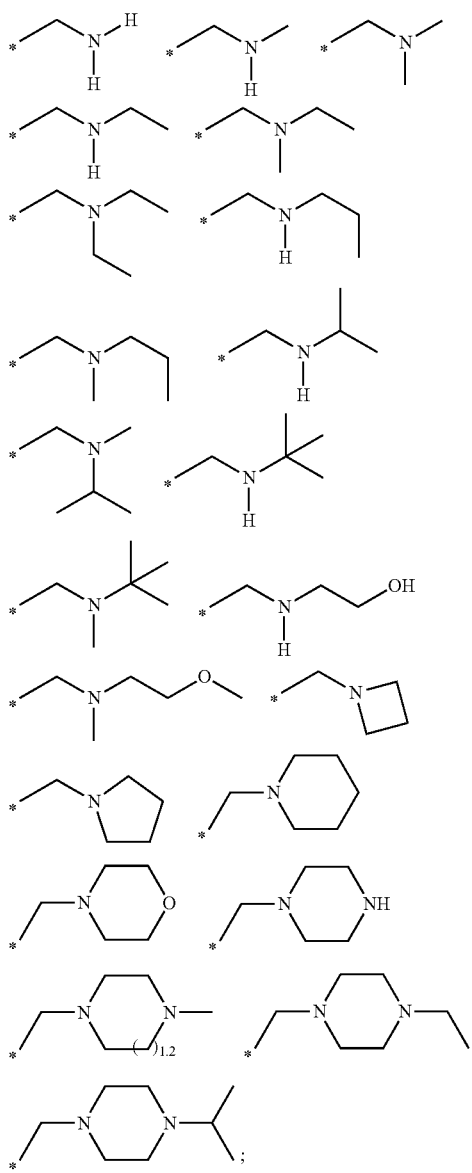

B is a radical selected from the group comprising the particular individual radicals

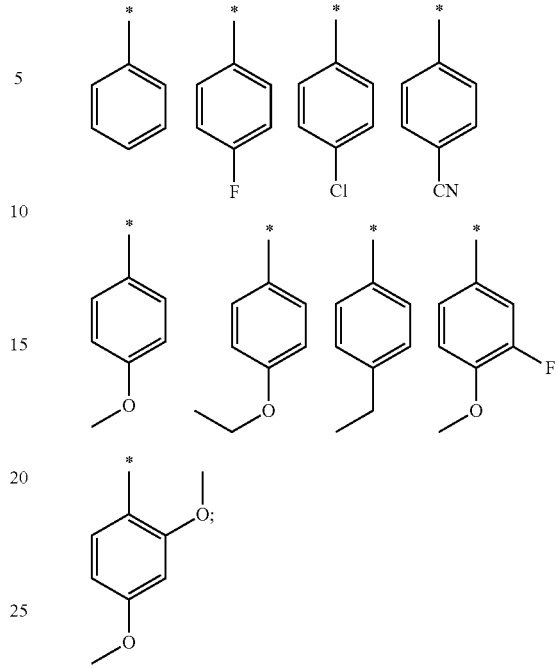

$R^1$ is selected from the group comprising chlorine, fluorine, and CN;

$R^2$ is selected from the group comprising hydrogen, chlorine, and fluorine;

Y is a radical selected from the group comprising the particular individual radicals

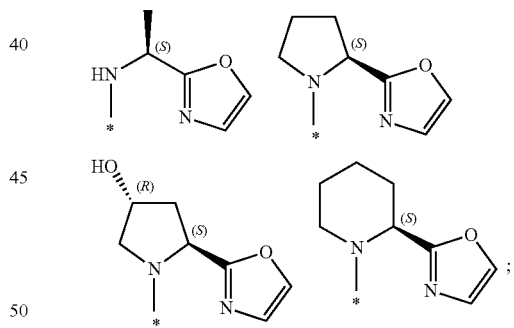

and tautomeric forms, prod rugs, and in particular physiologically tolerable salts of compounds of formula (I).

Also particularly preferred are mixtures of enantiomeric and diastereomeric forms of the compounds of formula (I) which include as a primary component compounds of formula (I) whose radicals Y have the stereochemistry shown here.

One very particularly preferred embodiment relates to compounds of general formula (I) as described above or in claim 1, wherein A is a radical selected from the group comprising the particular individual radicals

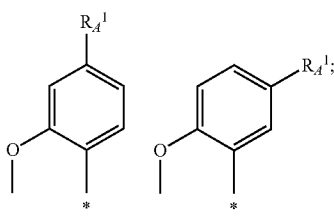

$R_A^1$ is a radical selected from the group comprising the particular individual radicals

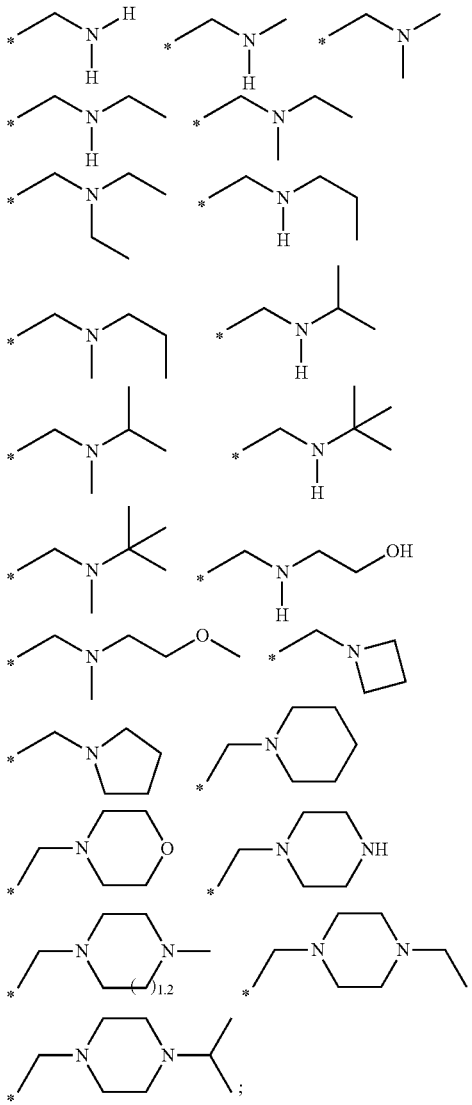

B stands for a radical

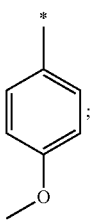

$R^1$ is selected from the group comprising chlorine and CN;
$R^2$ is selected from the group comprising hydrogen and chlorine;
Y is a radical selected from the group comprising the particular individual radicals

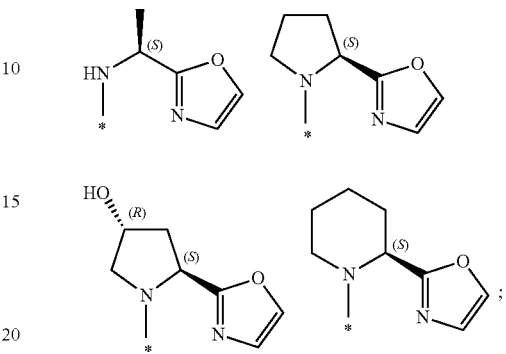

and tautomeric forms, prodrugs, and in particular physiologically tolerable salts of compounds of formula (I).

Also very particularly preferred are mixtures of enantiomeric and diastereomeric forms of the compounds of formula (I) which include as a primary component compounds of formula (I) whose radicals Y have the stereochemistry shown here.

One particularly preferred embodiment relates to compounds of general formula (I) as described above or in one of claims 1, wherein the radicals A, B, Y, $R^1$ and $R^2$ in each case independently have one of the meanings given above, and wherein the $R^2$ radical is bonded at the 6-position of the oxindole ring structure, and tautomeric forms, prodrugs, and in particular physiologically tolerable salts of compounds of formula (I).

One very particularly preferred embodiment relates to compounds of general formula (I) as described above or in one of claim 1, wherein the radicals A, B, and Y in each case independently have one of the meanings given above, and wherein the $R^1$ radical and the $R^2$ radical have the following meanings:
1) $R^1$=Cl or CN, and $R^2$=H;
or
2) $R^1$=Cl, and $R^2$=6-Cl;
and tautomeric forms, prodrugs, and in particular physiologically tolerable salts of compounds of formula (I).

One particularly preferred embodiment relates to compounds of general formula (I) given above, wherein the radicals A, B, $R^1$, and $R^2$ in each case independently have the meanings given above or in claim 1, and
Y stands for the radical

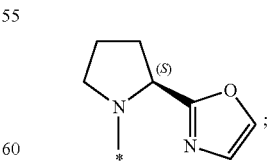

One particularly preferred embodiment relates to compounds of general formula (I) as described above or in claim 1, wherein the radicals A, B, Y, $R^1$ and $R^2$ in each case independently have one of the meanings given above, and wherein the $R^2$ radical is bonded at the 6-posilion of the oxindole ring structure, and tautomeric forms, prodrugs, and in particular physiologically tolerable salts of compounds of formula (I).

One very particularly preferred embodiment relates to compounds of general formula (I) as described above or in claim 1, wherein the radicals A, B, and Y in each case independently have one of the meanings given above, and wherein the R1 radical and the $R^2$ radical have the following meanings:

1) $R^1$=Cl or CN, and $R^2$=H;
or
2) $R^1$=Cl, and $R^2$=6-Cl;

and tautomeric forms, prodrugs, and in particular physiologically tolerable salts of compounds of formula(I).

One particularly preferred embodiment relates tu compounds of general formula (I) given above, wherein the radicals A, B, $R^1$, and $R^2$ in each case independently have the meanings given above or in claim 1, and
Y stands for the radical

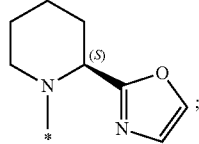

and tautomeric forms, prodrugs, and in particular physiologically tolerable salts of compounds of formula (1).

Also particularly preferred are mixtures of enantiomeric and diastereomeric forms of the compounds of formula (I) which include as a primary component compounds of formula (I) whose radicals Y have the stereochemistry shown here.

A further particularly preferred embodiment relates to compounds of general formula (I), wherein the radicals A. B, $R^1$, and $R^2$ in each case independently have the meanings given above or in claim 1, and
Y stands for the radical

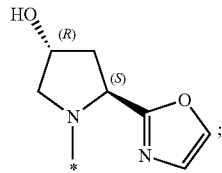

and tautomeric forms, prodrugs, and in particular physiologically tolerable salts of compounds of formula (I). Also particularly preferred arc mixtures of enantiomeric and diastereomeric forms of the compounds of formula (I) which include as a primary component compounds of formula (I) whose radicals Y have the stereochemistry shown here.

A further particularly preferred embodiment relates to compounds of general formula (I), wherein the radicals A, B, $R^1$ and $R^2$ in each case independently may have one of the meanings given above or in claim 1, and
Y stands for the radical

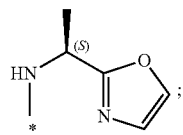

and tautomeric forms, prodrugs, and in particular physiologically tolerable salts of compounds of formula (I).

Also particularly preferred are mixtures of enantiomeric and diastereomeric forms of the compounds of formula (I) which include as a primary component compounds of formula (I) whose radicals Y have the stereochemistry shown here.

A further particularly preferred embodiment relates to compounds of general formula (I), wherein the radicals A, B, R1 and R2 in each case independently may have one of the meanings given above or in claim 1, and
Y stands for the radical

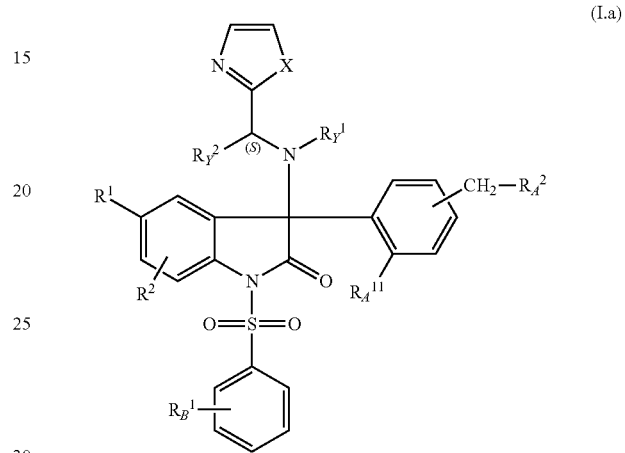

(I.a)

and tautomeric forms, prodrugs, and in particular physiologically tolerable salts of compounds of formula (I).

Also particularly preferred are mixtures of enantiomeric and diastereomeric forms of the compounds of formula (I) which include as a primary component compounds of formula (I) whose radicals Y have the stereochemistry shown here.

One very particularly preferred embodiment of the present invention relates to compounds of general formula (I.a), wherein the radicals $R^1$, $R^2$, $R_A^2$, $R_A^{11}$, $R_B^1$, $R_Y^1$, and $R_Y^2$, have one of the meanings given above, and X stands for O or S, preferably for O,
and tautomeric forms, prodrugs, and in particular physiologically tolerable salts of compounds of formula (I.a).

Also particularly preferred are mixtures of enantiomeric and diastereomeric forms of the compounds of formula (I.a) which include as a primary component compounds of formula (I.a) whose radicals Y have the stereochemistry shown here.

Particularly preferred are compounds of general formula (I) or (I.a) as given above or in claim 1, wherein the radicals A, B, Y, $R^1$, and $R^2$ in each case independently may have one of the meanings given above, and wherein the Y radical on the C atom bearing the $R_Y^4$ radical has the S configuration, and the carbon atom in the 3-position on the oxindol-2-one structure has either the R or the S configuration, and tautomeric forms, prodrugs, and in particular physiologically tolerable salts of compounds of formula (I) or (I.a).

Also particularly preferred are mixtures of enantiomeric and diastereomeric forms of the compounds of formula (I) or (I.a) which include as a primary component compounds of formula (I) or (I.a) whose radicals have the stereochemistry described here.

Particularly preferred are compounds of general formula (I) or (I.a) as given above or according to claim 1, wherein the radicals A, B, Y, $R^1$, and $R^2$ in each case independently may have one of the meanings given above, and wherein the compound is present in the form of the levorotatory stereoisomer with respect to the free base, and tautomeric forms, prodrugs, and in particular physiologically tolerable salts of compounds of formula (I) or (I.a).

Also particularly preferred are mixtures of enantiomeric and diastereomeric forms of the compounds of formula (I) or (I.a) which include as a primary component compounds of formula (I) or (I.a) whose radicals have the stereochemistry described here.

Particularly preferred are compounds of general formula (I) or (I.a) as given above or according to claim 1, characterized in that said compounds have a binding affinity Ki for the vasopressin receptor subtype V1b of less than approximately 100 nM, preferably between approximately 10 nM and approximately 100 nM, particularly preferably less than or equal to approximately 10 nM.

According to a further aspect of the present invention, at least one compound of general formula (I) or (I.a) as described above or according to one of claims 1 through 2 is provided for use as a medicament.

According to a further aspect of the present invention, a medicament containing at least one compound of general formula (I) or (I.a) is provided as described above or in one of claims 1 through 2.

According to a further aspect of the present invention, the use of at least one compound of general formula (I) or (I.a) as described above or according to one of claims 1 through 2 is provided for the treatment and/or prevention of at least one vasopressin-dependent disease, and/or for producing a medicament for the treatment and/or prevention of at least one vasopressin-dependent disease.

According to a further aspect of the present invention, the use of at least one compound of general formula (I) or (I.a) as described above or according to one of claims 1 through 2 is provided for the treatment and/or prevention of at least one disease. selected from the group comprising diabetes, inipidus, enuresis nocturna, incontinence, diseases characterized by blood clotting abnormalilies, and/or for delaying urination, and/or for producing a medicament for the treatment and/or prevention of at least one of the referenced diseases.

According to a further aspect of the present invention, the use of at least one compound of general formula (I) or (I.a) as described above or according to one of claims 1 through 2 is provided for the treatment and/or prevention of at least one disease selected from the group comprising hypertension, pulmonary hypertension, congestive heart failure, myocardial infarction, coronary spasm, unstable angina, percutaneous transluminal coronary angioplasty (PTCA), cardiac ischemia, disorders of the renal system, edema, renal vasospasm, necrosis of the renal cortex, hyponatremia, hypokalemia, Schwartz-Bartter syndrome, disorders of the gastrointestinal tract, gastric vasospasm, cirrhosis of the liver, ulcers of the stomach and intestine, emesis, emesis occurring during chemotherapy, and/or travel sickness, and/or for producing a medicament for the treatment and/or prevention of at least one of the referenced diseases.

According to a further aspect of the present invention, the use of at least one compound of general formula (I) or (I.a) as described above or according to one of claims 1 through 2 is provided for the treatment of affective disorders, and/or for producing a medicament for the treatment of affective disorders.

According to a further aspect of the present invention, the use of at least one compound of general formula (I) or (I.a) as described above or according to one of claims 1 through 2 is provided for the treatment of anxiety disorders and/or stress-related anxiety disorders, and/or for producing a medicament for the treatment of anxiety disorders and/or stress-related anxiety disorders.

According to a further aspect of the present invention, the use of at least one compound of general formula (I) or (I.a) as described above or according to one of claims 1 through 2 is provided for the treatment of memory disorders and/or Alzheimer's disease, and/or for producing a medicament for the treatment of memory disorders and/or Alzheimer's disease.

According to a further aspect of the present invention, the use of at least one compound of general formula (I) or (I.a) as described above or according to one of claims 1 through 2 is provided for the treatment of psychoses and/or psychotic disorders, and/or for producing a medicament for the treatment of psychoses and/or psychotic disorders.

According to a further aspect of the present invention, the use of at least one compound of general formula (I) or (I.a) as described above or according to one of claims 1 through 2 is provided for the treatment of Cushing's syndrome or other stress-related diseases, and/or for producing a medicament for the treatment of Cushing's syndrome or other stress-related diseases.

According to a further aspect of the present invention, the use of at least one compound of general formula (I) or (I.a) as described above [or] according to one of claims 1 through 2 is provided for the treatment of sleep disorders, and/or for producing a medicament for the treatment of sleep disorders.

According to a further aspect of the present invention, the use of at least one compound of general formula (I) or (I.a) as described above [or] according to one of claims 1 through 2 is provided for the treatment of depressive conditions, and/or for producing a medicament for the treatment of depressive conditions.

According to a further aspect of the present invention, the use of at least one compound of general formula (I) or (I.a) as described above [or] according to one of claims 1 through 2 is provided for the treatment of vasomotor symptoms and/or thermoregulatory malfunctions, such as "hot flush" symptoms, for example.

According to a further aspect of the present invention, the use of at least one compound of general formula (I) or (I.a) as described above [or] according to one of claims 1 through 2 is provided for the treatment and/or prevention of dependencies caused by drugs, medicaments, and/or other factors, for the treatment and/or prevention of stress resulting from withdrawal from one or more of the dependency-causing factors, and/or for the treatment and/or prevention of stress-induced relapse into the dependencies caused by drugs, medicaments, and/or other factors.

According to a further aspect of the present invention, the use of at least one compound of general formula (I) or (I.a) as described above [or] according to one of claims 1 through 2 is provided for the treatment and/or prevention of schizophrenia and/or psychosis.

According to a further aspect of the present invention, a method is provided for the treatment and/or prevention of at least one condition selected from the group comprising diabetes insipidus, enuresis nocturna, incontinence, diseases characterized by blood clotting abnormalities, and/or for delaying urination, in a patient, characterized in that the patient is administered an effective quantity of at least one compound of general formula (I) or (I.a) as described above or according to one of claims 1 through 2.

According to a further aspect of the present invention, a method is provided for the treatment and/or prevention of at least one condition selected from the group comprising hypertension, pulmonary hypertension, congestive heart failure, myocardial infarction, coronary spasm, unstable angina, percutaneous transluminal coronary angioplasty (PTCA), cardiac ischemia, disorders of the renal system, edema, renal vasospasm, necrosis of the renal cortex, hyponatremia, hypokalemia, Schwartz-Bartter syndrome, disorders of the gastrointestinal tract, gastric vasospasm, cirrhosis of the liver, ulcers of the stomach and intestine, emesis, emesis occurring during chemotherapy, and/or travel sickness in a patient, characterized in that the patient is administered an effective quantity of at least one compound of general formula (I) or (I.a).

According to a further aspect of the present invention, a method is provided for the treatment and/or prevention of affective disorders in a patient, characterized in that the patient is administered an effective quantity of at least one compound of general formula (I) or (I.a) as described above or according to one of claims 1 through 2.

According to a further aspect of the present invention, a method is provided for the treatment of anxiety disorders and/or stress-related anxiety disorders in a patient, characterized in that the patient is administered an effective quantity of at least one compound of general formula (I) or (I.a) as described above or according to one of claims 1 through 2.

According to a further aspect of the present invention, a method is provided for the treatment of memory disorders and/or Alzheimer's disease in a patient, characterized in that the patient is administered an effective quantity of at least one compound of general formula (I) or (I.a) as described above or according to one of claims 1 through 2.

According to a further aspect of the present invention, a method is provided for the treatment of psychoses and/or psychotic disorders in a patient, characterized in that the patient is administered an effective quantity of at least one compound of general formula (I) or (I.a) as described above or according to one of claims 1 through 2.

According to a further aspect of the present invention, a method is provided for the treatment of Cushing's syndrome in a patient, characterized in that the patient is administered an effective quantity of at least one compound of general formula (I) or (I.a) as described above or according to one of claims 1 through 2.

According to a further aspect of the present invention, a method is provided for the treatment and/or prevention of at least one condition selected from the group comprising hypertension. pulmonary hypertension, congestive heart failure, myocardial infarction, coronary spasm, unstable angina, percutaneous transluminal coronary angioplasty (PTCA), cardiac ischemia, disorders of the renal system, edema, renal vasospasm, necrosis of the renal cortex, hyponatremia, hypokalemia, Schwartz-Bartter syndrome, disorders of the gastrointestinal tract, gastric vasospasm, cirrhosis of the liver, ulcers of the stomach and intestine, emesis, emesis occurring during chemotherapy, and/or travel sickness in a patient, characterized in that the patient is administered an effective quantity of at least one compound of general formula (I) or (I.a).

According to a further aspect of the present invention, a method is provided for the treatment of depressive conditions in a patient, characterized in that the patient is administered an effective quantity of at least one compound of general formula (I) or (I.a) as described above or according to one of claims 1 through 2.

According to a further aspect of the present invention, a method is provided for the treatment and/or prevention of vasomotor symptoms and/or thermoregulatory malfunctions, such as "hot flush" symptoms, for example, in a patient, characterized in that the patient is administered an effective quantity of at least one compound of general formula (I) or (I.a) as described above or according to one of claims 1 through 2.

According to a further aspect of the present invention, a method is provided for the treatment and/or prevention of dependencies caused by drugs, medicaments, and/or other factors, for the treatment and/or prevention of stress resulting from withdrawal from one or more of the dependency-causing factors, and/or for the treatment and/or prevention of stress-induced relapse into the dependencies caused by drugs, medicaments, and/or other factors, in a patient, characterized in that the patient is administered an effective quantity of at least one compound of general formula (I) or (I.a) as described above or according to one of claims 1 through 2.

According to a further aspect of the present invention, a method is provided for the treatment and/or prevention of schizophrenia and/or psychosis in a patient, characterized in that the patient is administered an effective quantity of at least one compound of general formula (I) or (I.a) as described above or according to one of claims 1 through 2.

According to one preferred embodiment of the present invention, a method as described above or according to one of claims 1 through 2 is characterized in that the patient is a mammal, preferably a human being or a nonhuman mammal or a nonhuman transgenic mammal.

According to a further aspect of the present invention, a method is provided for preparing at least one compound of general formula (I) or (I.a) as described above or according to one of claims 1 through 2, characterized in that said compound may be prepared by a competent person skilled in the art and having knowledge of the technical teaching of the invention for carrying out and/or analogously carrying out method steps known as such.

A further preferred embodiment relates to compounds of general formula (I) or (I.a) as described above, characterized in that said compounds have selectivity for the vasopressin receptor subtype V1b with respect to at least one of the closely related vasopressin/oxytocin receptor subtypes (for example, vasopressin V1a, vasopressin V2, and/or oxytocin).

A further preferred embodiment relates to compounds of general formula (I) or (I.a) as described above, characterized in that said compounds have improved metabolic stability.

The metabolic stability of a compound may be measured, for example, by incubating a solution of the compound with liver microsomes of certain species (for example, rats, dogs, or humans), and determining the half-life value of the compound under these conditions (R. S. Obach, Curro Opin. Drug Discov. Devel. 2001, 4, 36-44). From higher half-life values, conclusions may be drawn concerning improved metabolic stability of the compound. Stability in the presence of human liver microsomes is of particular interest, since it allows a prediction of the metabolic decomposition of the compound in the human liver. Compounds having elevated metabolic stability (measured in the liver microsome test) are presumably also decomposed more slowly in the liver. The slower metabolic decomposition in the liver may result in higher or longer-lasting concentrations (effective levels) of the compound in the body, thereby increasing the elimination half-life value of the compounds according to the invention. Higher or longer-lasting effective levels may result in improved efficacy of the compound in the treatment or prevention of various vasopressin-dependent or oxytocin-dependent diseases. In addition, improved metabolic stability may result in increased bioavailability following oral administration, since after absorption in the intestine the compound has a lower rate of metabolic decomposition in the liver (referred to as the "first pass effect"). On account of an elevated concentration of the compound (effective level), increased oral bioavailability may result in improved efficacy of the compound following oral administration.

A further preferred embodiment relates to compounds of general formula (I) or (I.a) as described above, characterized in that, compared to the oxindole compounds known from the prior art, the compounds according to the invention have improved pharmacological activity in patients or applicable animal models which allow predictions to be made for use in treatment.

Any of these preferred definitions of a variable may be combined with any given definitions of the remaining variables.

A further preferred embodiment relates to compounds of general formula (I), selected from the group comprising Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and 91, discussed below, and tautomeric forms, prodrugs, and in particular physiologically tolerable salts, in addition to nonsalt forms of the compounds of formula (I). The compounds referenced above are particularly preferably provided in the form of the free base or in the form of acid addition products.

A further preferred embodiment relates to compounds of general formula (I) or (I.a) selected from the compounds from Examples 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, and 235 discussed below, and/or tautomeric forms, prodrugs, and in particular physiologically tolerable salts, in addition to nonsalt forms of the compounds of formula (I) or (I.a). The compounds referenced above are particularly preferably provided in the form of the free base or in the form of acid addition products.

The compounds according to the invention may be present as a mixture of diastereomers, or as a mixture of diastereomers in which one of the two diastereomers is concentrated, or in the form of essentially diastereomerically pure compounds (diastereomeric excess de>90%). The compounds are preferably present in the form of essentially diastereomerically pure compounds. The respective diastereomers, in turn, may [be present] in the form of a mixture of enantiomers (as the racemate, for example), as a mixture of enantiomers in which one of the two enantiomers is concentrated, or as essentially enantiomerically pure compounds (enantiomeric excess ee>90%). The respective diastereomers are preferably present in the form of essentially enantiomerically pure compounds. Compounds which are essentially diastereomerically and enantiomerically pure (de>90%, ee>90%) are particularly preferred.

In the sense of the description, physiologically tolerable salts, unless stated otherwise, may be formed by the following anions, for example:

Chloride, methanesulfonate, formate, trifluoroacetate, and/or acetate. Further acids which are suitable as salt-forming agents are listed in Fortschritte der Arzneimittelforschung [Advances in Drug Research], 1966, Birkhauser Verlag, Volume 10, pp. 224-285.

In the sense of the present description, unless stated otherwise the terms "alkyl," "cycloalkyl," "alkoxy," "haloalkyl," "alkenyl," "alkynyl," or "alkylene" as well as radicals derived therefrom always include unbranched and branched "alkyl," "cycloalkyl," "alkoxy," "haloalkyl," "alkenyl," "alkynyl," or "alkylene."

In the sense of the description, unless stated otherwise, "$C_0$ alkylene," "$(CH_2)_0$," or similar terms refer to a single bond.

In the sense of the description, unless stated otherwise, the terms "$C_1$-$C_6$ alkyl" and "$C_1$-$C_4$ alkyl" mean an optionally substituted straight-chain or branched, saturated hydrocarbon chain containing the number of carbon atoms stated in each case, i.e., containing 1 to 6 or 1 to 4 carbon atoms, respectively, for example methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, or 1-ethyl-2-methylpropyl, preferably methyl, ethyl, propyl, n-butyl, or isobutyl. In the sense of the description, unless stated otherwise, $C_1$-$C_4$ alkyl is preferably methyl, ethyl, n-propyl, isopropyl, n-butyl, sec-butyl, or t-butyl.

In the sense of the description, unless stated otherwise, the term "$C_1$-$C_6$ alkoxy" or "—O—$C_1$-$C_6$ alkyl" means a $C_1$-$C_6$ alkyl group, as defined above, which is optionally substituted via a bonded oxygen.

In the sense of the description, unless stated otherwise, the terms "$C_1$-$C_4$ alkylene" and "$C_0$-$C_4$ alkylene" (where $C_0$ alkylene means a single bond) mean an optionally substituted alkyl group containing 1 to 6 or 0 to 4 C atoms, respectively, as defined above, in which a hydrogen atom is replaced by a bond. Named in particular as examples are methylene, 1,2-ethylene, 1,2-propylene, 1,3-propylene, 1,2-butylene, 1,3-butylene, 2,3-butylene, 1,4-butylene, 2-methyl-1,3-propylene, 1,2-pentylene, 1,3-pentylene, 1,4-pentylene, 1,5-pentylene, 2,3-pentylene, 2,4-pentylene, 1-methyl-1,4-butylene, 2-methyl-1,4-butylene, 2-methyl-1,3-butylene, 2-ethyl-1,3-propylene, 3,4-hexylene, 3-methyl-2,4-pentylene, 3,5-heptylene, 2-ethyl-1,3-pentylene, 3-ethyl-3,5-heptylene, etc., preferably methylene, 1,2-ethylene, and 1,2-propylene.

In the sense of the description, unless stated otherwise, the term "$C_3$-$C_7$ cycloalkyl" means an optionally substituted, saturated hydrocarbon ring containing 3 to 7 ring members, such as cyclopropyl, cyclobutyl, cyclopentyl, cyclohexyl, or cycloheptyl.

In the sense of the description, unless stated otherwise, "$C_1$-$C_6$ haloalkyl" or "$C_1$-$C_4$ haloalkyl" means an optionally substituted $C_1$-$C_6$ alkyl or $C_1$-$C_4$ alkyl, as defined above, in which one, several, or all hydrogen atoms have been replaced by the same or different halogen atoms, as defined below.

In the sense of the description, unless stated otherwise, the term "$C_2$-$C_6$ alkenyl" means an optionally substituted branched or unbranched hydrocarbon chain containing 2 to 6 carbon atoms and having at least one double bond. The $C_2$-$C_6$ alkenyl preferably has one or two double bonds, most preferably one double bond. Examples of alkenyl groups are those given above for alkyl, wherein these groups have one or two double bonds, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl[sic; pentenyl], 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, and 1-ethyl-2-methyl-2-propenyl, in particular 2-propenyl, 2-butenyl, 3-methyl-2-butenyl, or 3-methyl-2-pentenyl.

In the sense of the description, unless stated otherwise, the term "$C_2$-$C_6$ alkynyl" means an optionally substituted, branched or unbranched hydrocarbon chain containing 2 to 6 carbon atoms and having at least one triple bond. The $C_2$-$C_6$ alkynyl preferably has one or two triple bonds, most preferably one triple bond. Examples of alkynyl groups are those given above for alkyl, wherein these groups have one or two triple bonds, for example ethynyl, 1-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl, preferably ethynyl, 1-propynyl, 1-butynyl, 1-methyl-2-propynyl, or 1-methyl-2-butynyl.

In the sense of the description, unless stated otherwise, the terms "3- to 10-membered carbocycle" or "4- to 7-membered carbocyclic ring" or "carbocyclic ring containing 2 to 10 C atoms" mean an optionally substituted, saturated, or completely or partially unsaturated hydrocarbon ring containing 3 to 10 C atoms or 4 to 7 C atoms or 2 to 10 C atoms, respectively, as ring atoms, for example cyclopropyl, cyclobutyl, cyclopentyl, cyclohexyl, cycloheptyl, cyclooctyl, cyclononyl, or cyclodecanyl. Unless explicitly stated or indicated in the associated structural formula, the carbocyclic ring may also contain heteroatoms as ring atoms. Unless stated otherwise, the heteroatom ring members may optionally be present instead of the C atom ring members or in addition to the C atom ring members.

In the sense of the description, unless stated otherwise, "halogen" is a halogen atom selected from, fluorine, chlorine, bromine, or iodine, preferably fluorine, chlorine, or bromine, more preferably fluorine or chlorine.

In the sense of the description, unless stated otherwise, the terms "$C_1$-$C_6$ haloalkyl" or "$C_1$-$C_4$ haloalkyl" refer to an optionally substituted alkyl radical, as defined above, which is partially or completely substituted by one or more radicals, which are the same or different, independently selected from the group comprising fluorine, chlorine, bromine, and iodine, for example $CH_2F$, $CHF_2$, $CF_3$, $CH_2Cl$, 2-fluoroethyl, 2-chloroethyl, and 2,2,2-trifluoroethyl.

In the sense of the description, unless stated otherwise, the radicals and groups when described by use of the terms "substituted" or "optionally substituted" are preferably singly or multiply, more preferably singly, doubly, or triply, most preferably singly or doubly, substituted. The term "in each case optionally substituted" is intended to clarify that not only the radical which immediately follows, but also all radicals named in the particular group may be independently substituted.

Examples of suitable substituents in the sense of the description and the terms "substituted," "optionally substituted," and "in each case optionally substituted," unless stated otherwise, contain the following: halogen, CN, $CF_3$, $CHF_2$, $OCF_3$, $OCHF_2$, $NO_2$, $NH_2$, OH, COOH, in each case branched or unbranched, optionally substituted $C_1$-$C_6$ alkyl, $C_3$-$C_7$ cycloalkyl, $C_1$-$C_6$ alkylene-O—$C_1$-$C_6$ alkyl, or $C_1$-$C_6$ thioalkyl, O—$C_1$-$C_4$ alkyl, N($C_1$-$C_4$ alkyl)$_2$, NH($C_1$-$C_4$ alkyl), aryl, —O-aryl, $C_1$-$C_4$ alkylene-O-aryl, NHCO—$C_1$-$C_4$ alkyl, NH—$SO_2$—$C_1$-$C_4$ alkyl, CO—$C_1$-$C_4$ alkyl, $SO_2$—$C_1$-$C_4$ alkyl, and NHCO-aryl, $NHSO_2$-aryl, $CONH_2$, $SO_2NH_2$, $SO_2$-aryl, SO—$C_1$-$C_4$ alkyl, SO-aryl, N-pyrrolidinyl, N-piperidinyl, and N-morpholinyl optionally substituted in the aryl radical. Preferred substituents are F, Cl, $CF_3$, $OCF_3$, $NH_2$, $NO_2$, OH, COOH, $C_1$-$C_4$ alkyl, methoxy, acetyl, NH-acetyl, and $SO_2NH_2$.

In the sense of the description, unless stated otherwise, terms in parentheses with subscript integers are understood to mean that the radicals in parentheses in each case may be the same or different. For example, in the sense of the description, "N($C_1$-$C_4$ alkyl)$_2$," stands for N($C_1$-$C_4$ alkyl)($C_1$-$C_4$ alkyl), where the two radicals ($C_1$-$C_4$ alkyl) may be the same or different.

In the sense of the description, unless stated otherwise, the symbol (*) in the chemical formulas of $R^1$, $R^2$, A, B, and Y in general formula (I) represent the linkage points of the stated radicals with the oxindole ring structure or with a group joined to the oxindole ring structure.

In the sense of the description, unless stated otherwise, the symbol (_____) represents a single bond, which, if it is bonded to a chiral center, is intended to mean that the corresponding compound is present either as an approximately 1:1 mixture (racemate, R/S form) of the two enantiomeric forms in relation to the chiral center, or as separate (R)-enantiomers and/or (S)-enantiomers in relation to the chiral center.

In the sense of the description, unless stated otherwise, the symbol "—SO—" means a sulfoxide group (—S(=O)—).

The symbol $( \ldots )_{1,2}$ means that the term in parentheses occurs once or twice. For example, "$(CH_2)_{1,2}$" (or an equivalent notation) means the radical $(CH_2)_1(=(CH_2))$, or alternatively, $(CH_2)_2$.

In the sense of the description, unless stated otherwise, the symbol "—S02-" means a radical selected from the group comprising the sulfone group (—(O=S=O)—) or alternatively, the sulfinic acid group (—(S=0)-0-), where the meaning of the sulfone group is preferably intended.

In the sense of the description, unless stated otherwise, the term "aromatic, heteroaromatic, partially aromatic, or partially heteroaromatic mono- or bicyclic ring" means a mono- or bicyclic ring in each case composed of C atoms ("aromatic" or "partially aromatic") or a combination of C atoms and heteroatoms ("heteroaromatic" or "partially heteroaromatic"), and having an aromatic number of double bonds in the ring ("monocyclic") or in the two rings ("bicyclic") ("aromatic" or "heteroaromatic"), or in only one of the rings ("partially aromatic" or "partially heteroaromatic").

Examples of aromatic rings are phenyl, naphthyl, fluorenyl, indenyl, and phenanthrenyl, with phenyl and naphthyl, which may be 1-naphthyl or 2-naphthyl, being preferred, and phenyl being most preferred.

Examples of heteroaromatic rings are 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl, and benzoxazolyl, 2,3-dihydro-1,4-benzodioxinyl, 1,3-benzodioxolyl, and 2,1,3-benzothiadiazolyl.

Examples of partially aromatic rings are 5,6,7,8-tetrahydronaphthalen-1-yl, 5,6,7,8-tetrahydronaphthalen-2-yl, and indan-4-yl and indan-5-yl.

Examples of partially heteroaromatic rings are benzo[1,3]dioxol-4-yl, benzo[1,3]dioxol-5-yl, 2,3-dihydrobenzo[1,4]dioxin-5-yl, and 2,3-dihydrobenzo[1,4]dioxin-6-yl.

In the sense of the description, unless stated otherwise, the terms "saturated, or completely or partially unsaturated, carbocyclic ring" or "saturated or unsaturated carbocyclic ring" mean a ring or ring system which is formed from C atoms and optionally from one or more heteroatoms, and which has no double bond present in the ring ("saturated"), or which has one or more conjugated, unconjugated, or only partially conjugated double bonds ("partially or completely unsaturated" or "unsaturated"). The carbocyclic ring may be a mono-, bi-, or tricyclic ring. In the sense of the description, unless stated otherwise, a bi- or tricyclic, saturated carbocycle may be a bicycloalkyl or tricycloalkyl radical containing 2 to 10 carbon atoms. For a bicycloalkyl radical, the ring system preferably contains 5 to 10, more preferably 6 to 10 carbon atoms. For a tricycloalkyl radical, the ring system may preferably contain 6 to 10, more preferably 6 to 10, [sic]carbon atoms. Examples of a bicycloalkyl radical include indanyl, camphyl, and norbornyl. Examples of a tricycloalkyl radical include adamantyl.

The term "in the sense of the description" encompasses the present application in all its parts, in particular the description, the claims, the drawings, and the abstract.

The compounds according to the invention are active after administration via various routes (for example, intravenous, intramuscular, oral), in particular oral.

The present invention also provides for use of the compounds according to the invention for the treatment and/or prevention of diseases in which the course of the disease is a function, at least partially, of vasopressin, i.e., diseases which exhibit an elevated vasopressin level which may directly or indirectly contribute to the clinical symptoms.

The present invention also provides for use of the compounds according to the invention for the treatment and/or prevention of diseases such as diabetes insipidus, enuresis nocturna, incontinence, diseases characterized by blood clotting abnormalities, and/or for delaying urination.

The present invention also provides for use of the compounds according to the invention for the treatment and/or prevention of the following diseases: hypertension, pulmonary hypertension, congestive heart failure, myocardial infarction, coronary spasm, unstable angina, percutaneous transluminal coronary angioplasty (PTCA), cardiac ischemia, disorders of the renal system, edema, renal vasospasm, necrosis of the renal cortex, hyponatremia, hypokalemia, Schwartz-Bartter syndrome, disorders of the gastrointestinal tract, gastric vasospasm, cirrhosis of the liver, ulcers of the stomach and intestine, emesis, emesis occurring during Chemotherapy, and travel sickness.

The compounds according to the invention may also be used for the treatment of various vasopressin-dependent symptoms caused by the central nervous system or changes in the hypothalamic pituitary adrenal (HPA) axis, for example for affective disorders such as depressive conditions and bipolar disorders. These include, for example, dysthymic disorders, phobias, post-traumatic stress disorders, general anxiety disorders, panic attacks, seasonal affective disorder, depression, and sleep disorders.

The compounds according to the invention may likewise be used for the treatment of anxiety disorders and stress-related anxiety disorders, for example generalized anxiety disorders, phobias, post-traumatic anxiety disorders, panic anxiety disorders, obsessive-compulsive anxiety disorders, acute stress-related anxiety disorders, and social phobias. The compounds according to the invention may also be used for the treatment of memory disorders, Alzheimer's disease, psychoses, psychotic disorders, sleep disorders, and/or Cushing's syndrome, in addition to all stress-related diseases.

The present invention further relates to pharmaceutical compositions containing an effective dose of a compound according to the invention or a pharmaceutically acceptable salt thereof, and suitable pharmaceutical carriers (excipients).

These excipients are selected depending on the pharmaceutical form and the desired type of administration.

The compounds according to the invention of general formula (I), or optionally suitable salts of these compounds, may be used to prepare pharmaceutical compositions for oral, sublingual, subcutaneous, intramuscular, intravenous, topical, intratracheal, intranasal, transdermal, or rectal administration, and administered to animals or humans in uniform administration forms, mixed with conventional pharmaceutical carriers, for prevention or treatment of the above disorders or diseases.

The suitable uniform administration forms (unit dosage forms) contain forms for oral administration, such as tablets, gelatin capsules, powders, granules, and solutions or suspensions for oral intake, forms for sublingual, buccal, intratracheal, or intranasal administration, aerosols, implants, forms for subcutaneous, intramuscular, or intravenous administration, and forms for rectal administration.

For topical administration the compounds according to the invention may be used in cremes, salves, or lotions.

To achieve the desired prophylactic or therapeutic effect, the dosage of the active component may vary between 0.01 and 50 mg per kg body weight per day.

Each unit dose may contain 0.05 to 5000 mg, preferably 1 to 1000 mg, of the active component in combination with a pharmaceutical carrier. This unit dose may be administered 1 to 5 times per day, so that a daily dosage of 0.5 to 25,000 mg, preferably 1 to 5000 mg, is administered.

If a solid composition in the form of tablets is prepared, the main component is mixed with a pharmaceutical carrier, such as gelatin, starch, lactose, magnesium stearate, talc, silicon dioxide, or the like.

The tablets may be coated with sucrose, a cellulose derivative, or another suitable substance, or may be treated in another way to obtain a sustained or delayed activity and to continuously release a predetermined quantity of the active component.

A preparation in the form of gelatin capsules is obtained by mixing the active component with an extender and filling the resulting mixture into soft or hard gelatin capsules.

A preparation in the form of a syrup or elixir or for administration in the form of drops may contain active components together with a sweetener, which preferably is calorie-free, methylparaben or propylparaben as antiseptic, a fragrance, and a suitable dye.

The water-dispersible powders or granules may contain the active components mixed with dispersants, wetting agents, or suspension agents such as polyvinylpyrrolidones, and sweeteners or flavorants.

Rectal administration is achieved by use of suppositories prepared with binders, for example cocoa butter or polyethylene glycols, which melt at the rectal temperature. Parenteral administration is achieved by using aqueous suspensions, isotonic salt solutions, or sterile, injectable solutions containing pharmacologically acceptable dispersants and/or wetting agents, for example propylene glycol or polyethylene glycol.

The active component may also be formulated as microcapsules or centrosomes, if suitable, together with one or more carriers or additives.

In addition to the compounds of general formula (I) or the pharmaceutically acceptable salts thereof, the compositions according to the invention may contain other active components which may be useful for treatment of the above-referenced disorders or diseases.

Therefore, the present invention further relates to pharmaceutical compositions in which multiple active components are present together, at least one of which is a compound according to the invention.

Preparation of the Compounds According to the Invention

Synthetic pathways for preparing the compounds according to the invention are described below by way of example.

The oxindoles according to the invention may be prepared, for example, according to the pathway illustrated in synthesis diagrams 1.A and 1.B. In synthesis diagrams 1.A and 1.B the variables have the same meanings as in general formula (I) or (I.a).

SYNTHESIS DIAGRAM 1.A

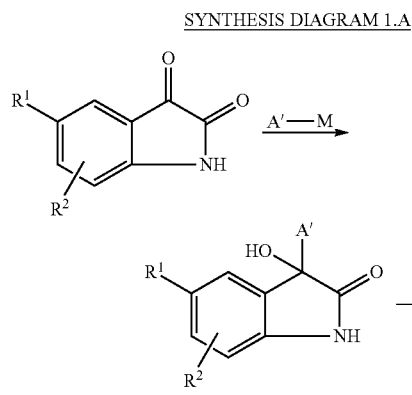

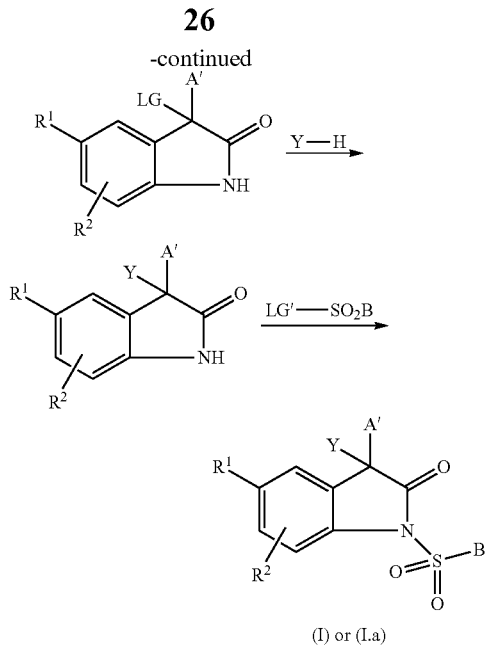

Compounds of general formula (I) or (I.a) may be synthesized, for example, in the manner shown in synthesis diagram 1.A. 3-Hydroxyoxindoles having a substituent A' in the 3-position, where A' has one of the meanings given for A or is a protected precursor of A, may be prepared by addition of organometallic compounds A'-M (M=Li, MgHal) at the 3-keto group of substituted isatines. The hydroxy group of the 3-hydroxyoxindoles thus obtained may be substituted by a leaving group LG (where LG stands for halogen, for example) using methods known to one skilled in the art. Reacting these compounds with primary or secondary amines Y—H results in 3-"Y"-substituted 3-aminooxindoles. Deprotonation of the oxindole nitrogen and sulfonylation with compounds of formula B—SO$_2$LG' (where LG' stands for halogen, for example, in particular chlorine) results in optionally protected compounds of general formula (I) or (I.a).

When A' is a protected precursor of a group A, compounds of general formula (I) or (I.a) are obtained by deprotection.

Other compounds of general formula (I) or (I.a) may be obtained by subsequent functionalization and/or derivatization, using methods known to one skilled in the art. The synthesis shown in synthesis diagram 1.A is explained in greater detail with reference to the route shown in synthesis diagram 1.B. The indicated synthesis pathway may be transferred to analogous compounds.

SYNTHESIS DIAGRAM 1.B

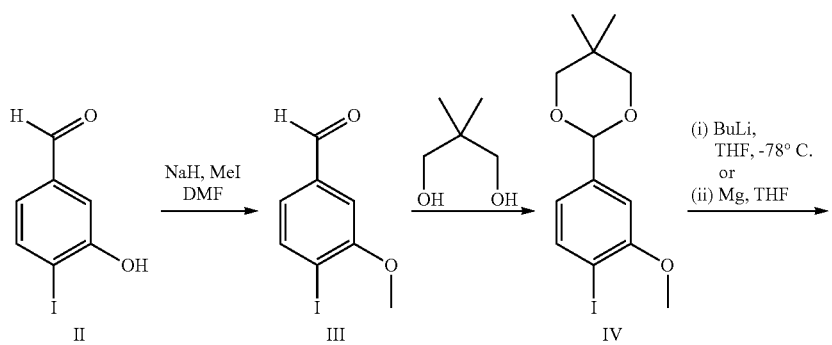

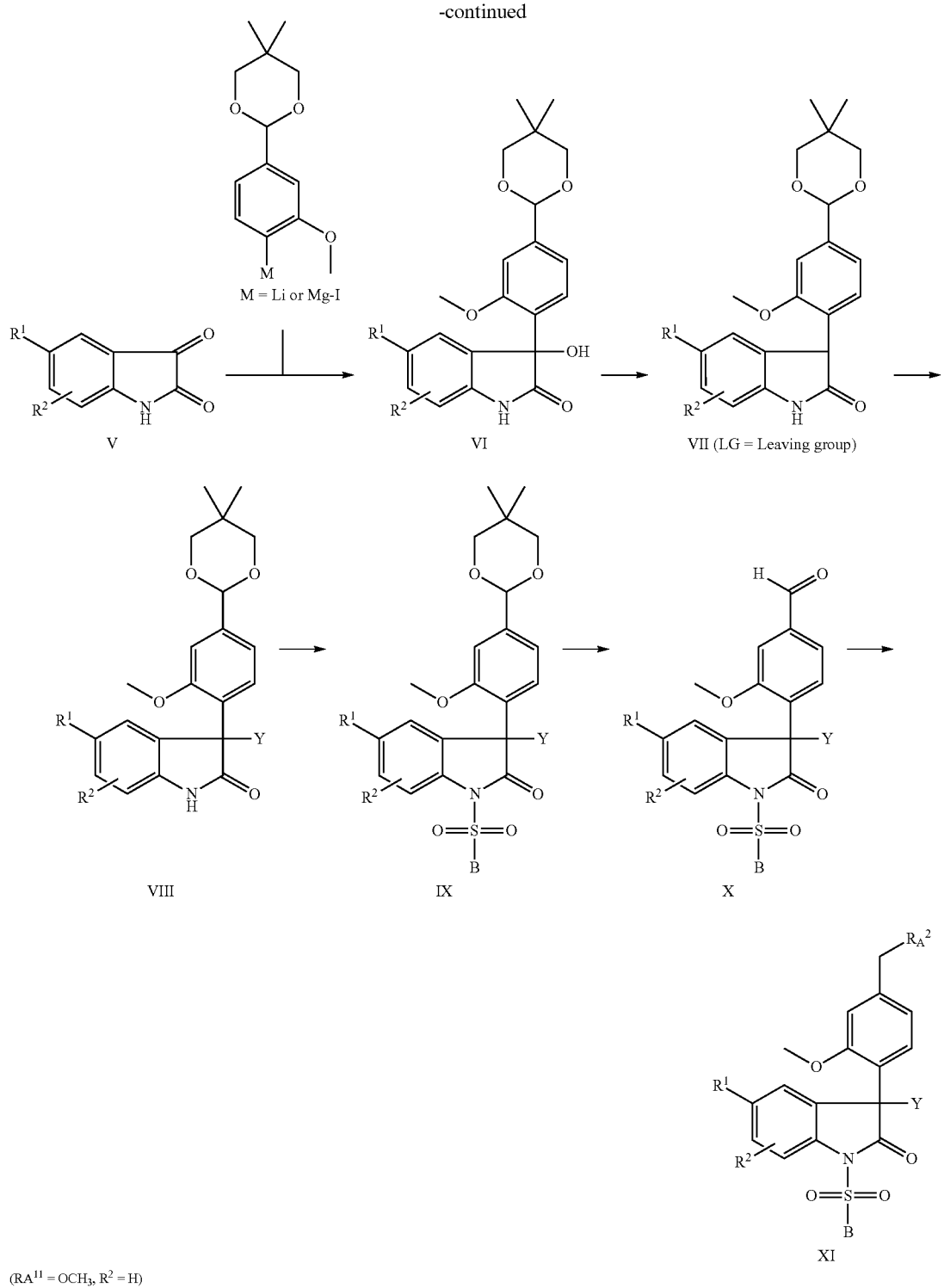

(RA[11] = OCH₃, R² = H)

Compounds in which an amino group $R_A^2$ is bonded to the ring A via a methylene group (benzylic amines) may be synthesized as shown in synthesis diagram 1.B. The 3-hydroxyoxindoles (VI) may be produced by addition of organolithium or Grignard compounds at the 3-keto group of the substituted isatines V in an etheric solvent such as THF. Using the example of $R_A^{11}$ =OCH₃, the lithium species may be obtained from iodine-aryl compound IV by treatment with organolithium reagents, for example n-butyl lithium, in THF at low temperatures. Alternatively, the corresponding Grignard compound may be produced from (IV) by treatment with magnesium in an etheric solvent such as THF. The cyclic acetal (IV) may be produced in two steps (methylation of the phenol oxygen, followed by protection of the aldehyde in the form of the acetal) from commercially available 3-hydroxy-4-iodobenzaldehyde (II). The isomeric structural unit (protected aldehyde function para to the methoxy group) may be prepared in an analogous manner from commercially available 3-bromo-4-methoxybenzaldehyde. In addition, the structural units having a protected aldehyde function may be analogously obtained from commercially available 3-bromo-4-fluorobenzaldehyde, 3-bromo-4-ethoxybenzaldehyde, and 3-bromo-4-methylbenzaldehyde, and may be used for the synthesis of compounds according to the invention which bear fluorine, ethoxy, or methyl as radical $R_A^{11}$ in the 2-position of the phenyl ring A. For the synthesis of compounds where $R_A^{11}$=H, commercially available Grignard compounds, for example (3-(1-pyrrolidinylmethyl)phenyl)magnesium bromide or (4-(1-pyrrolidinylmethyl)phenyl)magnesium bromide, may be reacted with the isatines (V).

When A is an aromatic heterocycle, metallated heteroaromatics bearing a protected formyl group may be prepared in an analogous manner (protection of the formyl function in the form of a cyclic acetal, followed by lithium-halogen exchange or insertion of magnesium into the heteroaryl-halogen bond), using, for example, commercially available 2-bromo-4-formyl-3-methoxypyridine, 6-bromo-2-formylpyridine, 5-bromo-3-formylpyridine, 2-bromo-4-formylpyridine, 2-bromo-5-formylpyridine, 4-bromo-2-formylthiophene, 3-bromo-2-formylthiophene, 5-bromo-2-formylthiophene, or 3-bromo-4-formylthiophene.

Compounds according to the invention in which radical A in general formula (I) is a 2-methoxypyridin-3-yl-radical may be prepared starting from 6-methoxypyridine-3-carbaldehyde. The aldehyde may be brominated ortho to the methoxy group (European Journal of Medicinal Chemistry (1977), 12(6), 531-6), and the resulting 5-bromo-6-methoxypyridine-3-carbaldehyde may then be protected in the form of the cyclic acetal. The organolithium species obtained by lithium-halogen exchange with butyl lithium may be added to substituted isatines as described above.

The 3-hydroxyoxindoles (VI) may be converted to the compounds (VII) bearing a leaving group LG in the 3-position, wherein the leaving group LG may be customary leaving groups, for example halides, mesylate, or tosylate. Using the example of LG=chlorine, the intermediate product (VII) may be prepared by treating the alcohol VI with thionyl chloride in the presence of a base, for example pyridine, in a solvent, for example dichloromethane. In the presence of a base such as N,N-diisopropylethylamine the compounds (VII) are then reacted with primary or secondary amines Y—H in a solvent, for example dichloromethane, to produce the corresponding 3-aminooxindoles (VIII), in which the radical Y is linked to the 3-carbon atom of the oxindole structure via a nitrogen atom. One of the preferred radicals Y is (S)-2-oxazol-2-yl-pyrrolidin-1-yl. The corresponding 2-(S)-pyrrolidin-2-yl-oxazole may be prepared in the form of the HBr salt according to US 2003/0069223. Other preferred radicals Yare (S)-2-oxazol-2-yl-piperidin-1-yl, (2S,4R)-4-hydroxy-2-oxazol-2-yl-pyrrolidin-1-yl, and (S)-1-oxazol-2-yl-ethylamino.

Compounds of formula Y-H are known, or may be prepared according to diagrams 2.A through 8 shown below.

As illustrated in synthesis diagram 2.A and in a manner analogous to the syntheses described in US 2003/0069223 for the HBr salt of 2-(S)-pyrrolidin-2-yl-oxazole, the HBr salt of (2S,4R)-4-hydroxy-2-oxazol-2-yl-pyrrolidine may be prepared starting from commercially available Cbz/tert-butyl-protected (2S,4R)-4-hydroxyproline (Cbz-Hyp(Tbu)-OH).

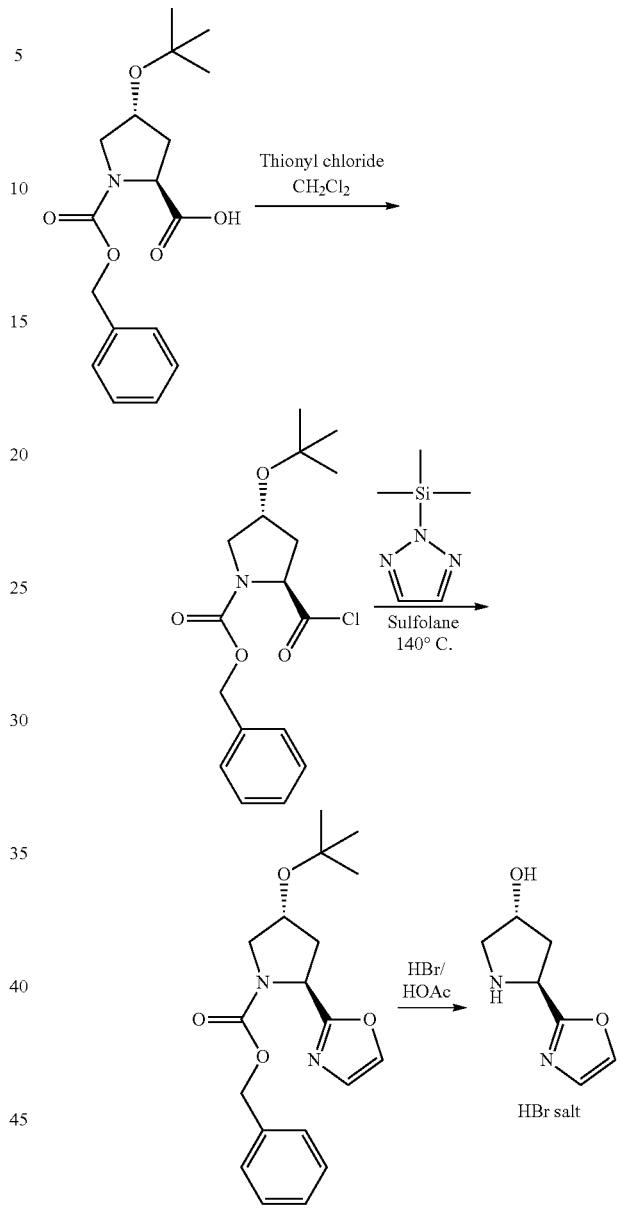

SYNTHESIS DIAGRAM 2.A

According to an alternative method described in synthesis diagram 2.B, the HBr salt of (2S,4R) -4-acetoxy-2-oxazol-2-yl-pyrrolidine may be prepared, starting with commercially available Cbz/tert-butyl-protected (2S,4R)-4-hydroxyproline (Cbz-Hyp(Tbu)-OH, Bachem). For this purpose, Cbz-Hyp(Tbu)-OH is coupled to aminoacetaldehyde dimethylacetal, using a coupling reagent (for example, N-(3-dimethylaminopropyl)-N'-ethylcarbodiimide hydrochloride (EDCI)/1-hydroxybenzotriazole (HOBt)), in a suitable solvent (DMF, for example). The aldehyde function is released by treating the resulting coupling product with an acid (aqueous hydrochloric acid, for example) in an organic solvent (acetone, for example). In a manner analogous to WO 2004/113353 the oxazole ring may be closed by cyclocondensation, using hexachloroethane, triphenylphosphine, and triethylamine in dichloromethane. Lastly, the Cbz protective group may be removed by treatment with hydrobromic acid/glacial acetic acid. Under these conditions the tert-butyl protective group may also be cleaved, and the resulting alcohol is acetylated. The deacetylation also takes place under the conditions of the aldehyde release (synthesis diagram 1.B, reaction from (IX) to (X)). This results in the (2S,4R)-4-hydroxy-2-oxazol-2-yl-pyrrolidin-1-yl compounds according to the invention.

SYNTHESIS DIAGRAM 2.B

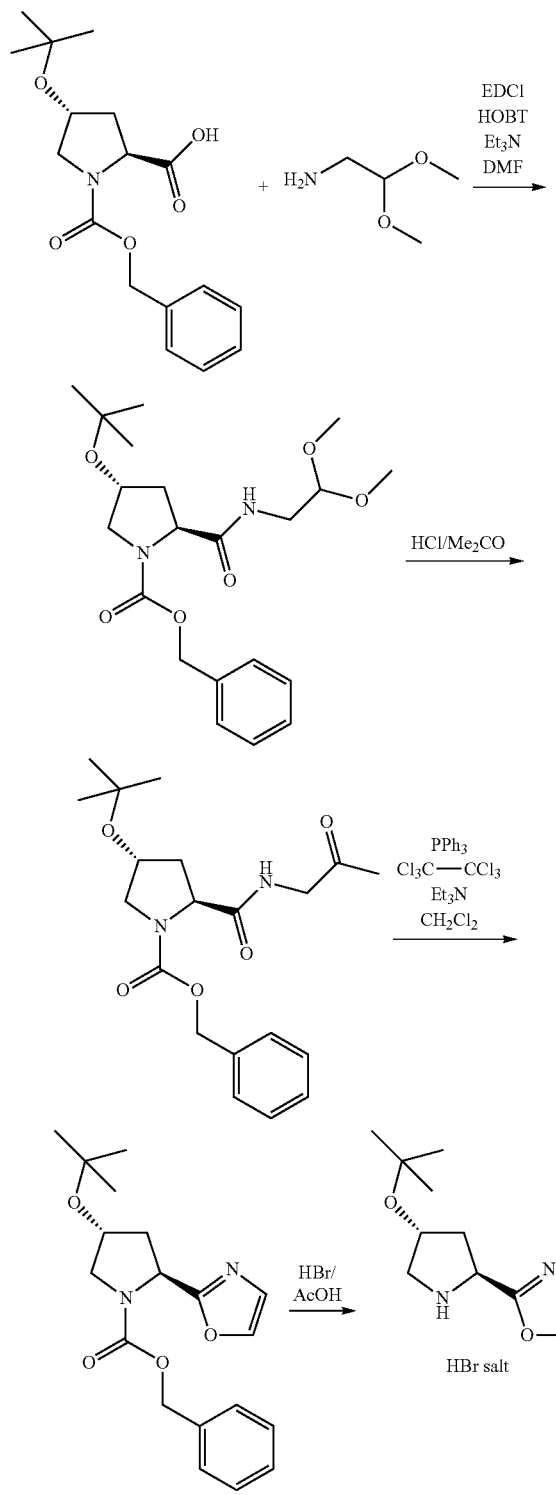

As illustrated in synthesis diagram 3, (S)-1-oxazol-2-yl-ethylamine may be prepared from phthalimide-protected L-alanine in three steps. Phthalimide-protected L-alanine (Pht-Ala-OH) may be converted to the corresponding acid chloride (Pht-Ala-Cl) by treatment, for example, with oxalyl chloride and catalytic quantities of N,N-dimethylformamide (DMF) in a suitable solvent (dichloromethane, for example). The phthalimide-protected oxazole structural unit may be obtained by treating the acid chloride with 2-trimethylsilanyl-2H-[1,2,3]triazole and heating in sulfolane. Removal of the phthalimide protective group, for example by using hydrazine hydrate in ethanol, results in the free (S)-1-oxazol-2-yl-ethylamine.

SYNTHESIS DIAGRAM 3

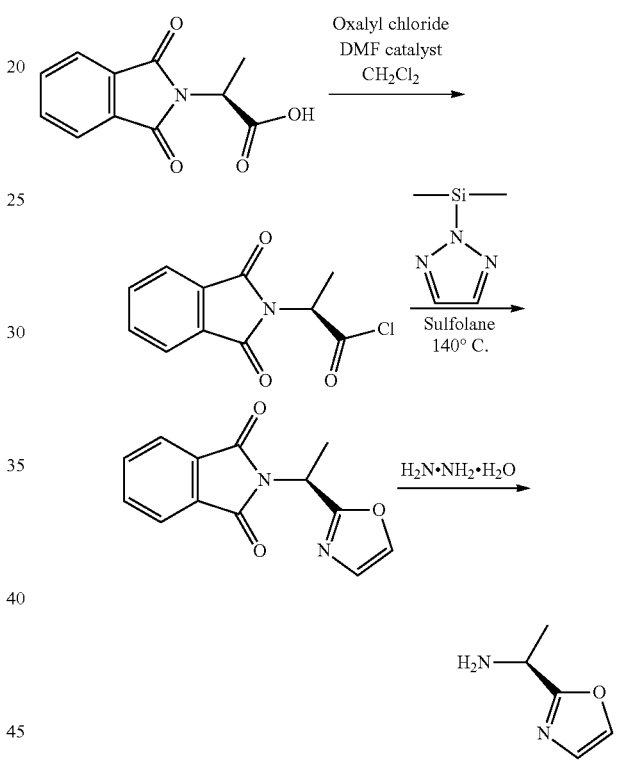

As illustrated in synthesis diagram 4, starting with (2S,4R)-4-tert-butoxy-2-oxazol-2-yl-pyrrolidin-1-carboxylic benzyl ester (see synthesis diagram 2.B for preparation), in a three-step reaction sequence the corresponding 4-alkoxy derivatives, for example the HBr salt of (2S,4R)-4-methoxy-2-oxazol-2-yl-pyrrolidine, may be prepared. In a first step the tert-butyl ether is cleaved under acidic conditions (for example, using trifluoroacetic acid in $CH_2Cl_2$). In a second step the free hydroxy function thus obtained is alkylated with an alkyl halide (methyl iodide, for example) following prior deprotonation with a strong base (NaH, for example). Lastly, the Cbz protective group for the amino function is removed by use of a hydrobromic acid/glacial acetic acid mixture. (2S,4R)-4-tert-butoxy-2-oxazol-2-yl-pyrrolidine may be obtained by catalytic hydrogenation (removal of the Cbz protective group) of (2S,4R)-4-tert-butoxy-2-oxazol-2-yl-pyrrolidine-1-carboxylic benzyl ester.

SYNTHESIS DIAGRAM 4

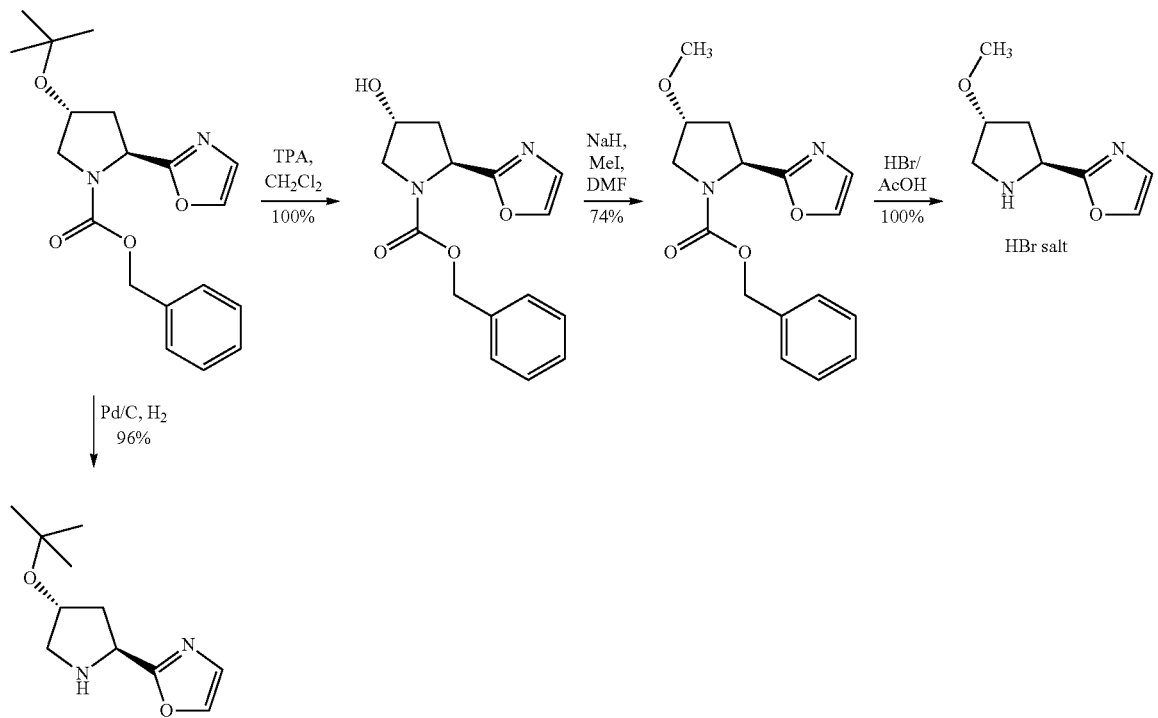

As illustrated in synthesis diagram 5, the HBr salt of (S)-2-methyl-2-oxazol-2-yl-pyrrolidine may be prepared, starting with commercially available (S)-2-methylpyrrolidine-2-carboxylic acid (H -alpha-Me-Pro-OH, Bachem). For this purpose the amino function is N-protected using a protective group (Cbz, for example), and is then coupled to aminoacetaldehyde dimethylacetal, using a coupling reagent (EDCl/HOBt, for example) in a suitable solvent (DMF, for example). The aldehyde function is released by treatment with an acid (aqueous hydrochloric acid, for example) in an organic solvent (acetone, for example). In a manner analogous to WO 20041113353 the oxazole ring may be closed by cyclocondensation, using hexachloroethane, triphenylphosphine, and triethylamine in dichloromethane. Lastly, the Cbz protective group may be removed by treatment with hydrobromic acid/glacial acetic acid.

The HBr salt of (2S,4R)-4-fluoro-2-oxazol-2-yl-pyrrolidine may be prepared in an analogous manner, starting with commercially available (2S,4R)-4- fluoropyrrolidine-2-carboxylic acid.

SYNTHESIS DIAGRAM 5

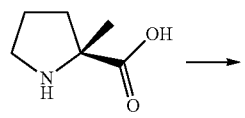

-continued

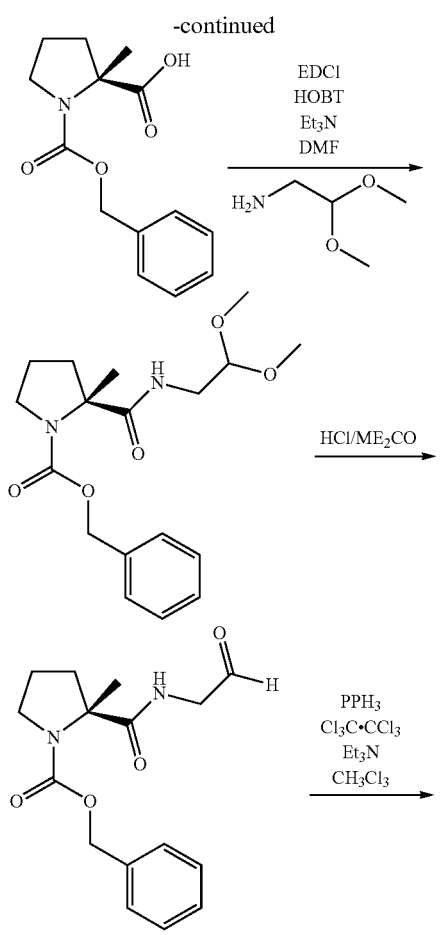

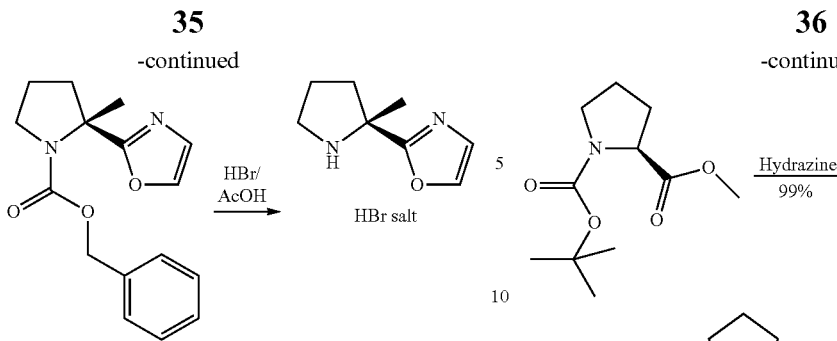

As shown in synthesis diagram 6 and in a manner analogous to WO 2002/102799, the TFA salt of (S)-3-pyrrolidin-2-yl-[1,2,4]oxadiazole may be prepared in three steps. In a first step hydroxylamine undergoes addition with commercially available (S)-1-N-Boc-2-cyanopyrrolidine. In a second step the obtained product and trimethyl orthoformiate are condensed together under acid catalysis (para-toluenesulfonic acid). Lastly, removal of the Boc protective group by use of trifluoroacetic acid results in the desired product.

The TFA salt of (S)-2-pyrrolidin-2-yl-[1,3,4]oxadiazole may likewise be prepared in three steps, as shown in synthesis diagram 6 and in a manner analogous to WO 2002/102799. In a first step hydrazine is used to convert commercially available Boc-Pro-OMe to the corresponding hydrazide. In a second step the obtained hydrazide is condensed with trimethyl orthoformiate under acid catalysis (p-TsOH). Removal of the Boc protective group by use of trifluoroacetic acid results in the desired product.

SYNTHESIS DIAGRAM 6

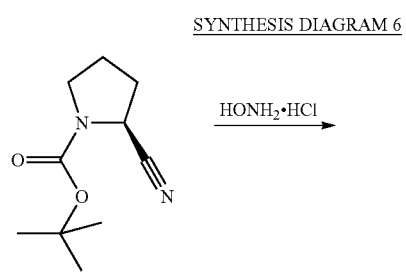

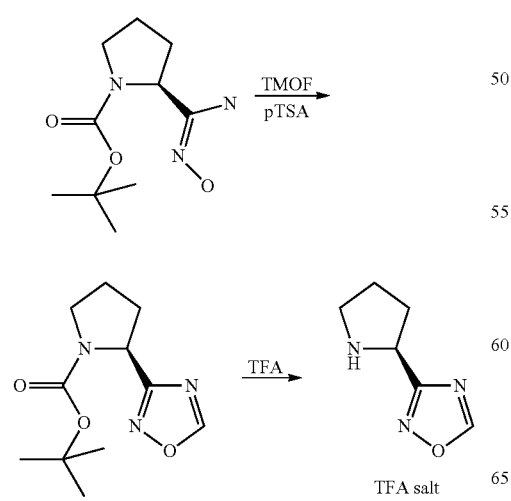

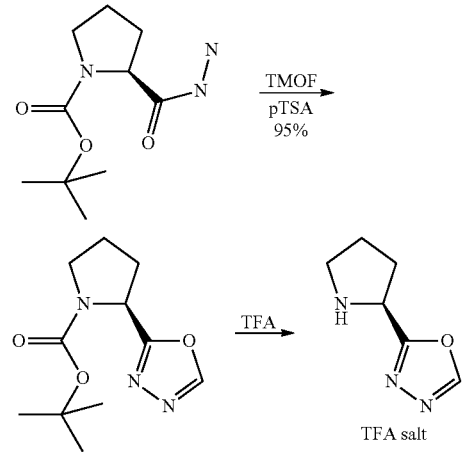

The HBr salt of 4-methyl-2-(S)-pyrrolidin-2-yl-oxazole may be prepared starting with commercially available Cbz-Pro-OH, as illustrated in synthesis diagram 7. The protected amino acid is coupled to 2-amino-1-propanol using a coupling reagent, for example N-(3-dimethylaminopropyl)-N'-ethylcarbodiimide hydrochloride (EDCI) in the presence of 1-hydroxybenzotriazole, in a solvent, for example DMF. The aldehyde function may be generated by oxidation with Dess-Martin reagent, or according to Swern (J. Org. Chem. 43, 2480 (1978)). In a manner analogous to WO 2004/113353 the oxazole ring may be closed by cyclocondensation, using hexachloroethane, triphenylphosphine, and triethylamine in dichloromethane. Lastly, the Cbz protective group may be removed by treatment with hydrobromic acid/glacial acetic acid.

SYNTHESIS DIAGRAM 7

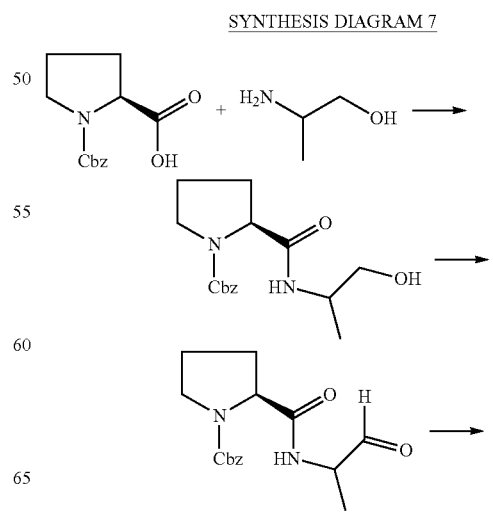

37

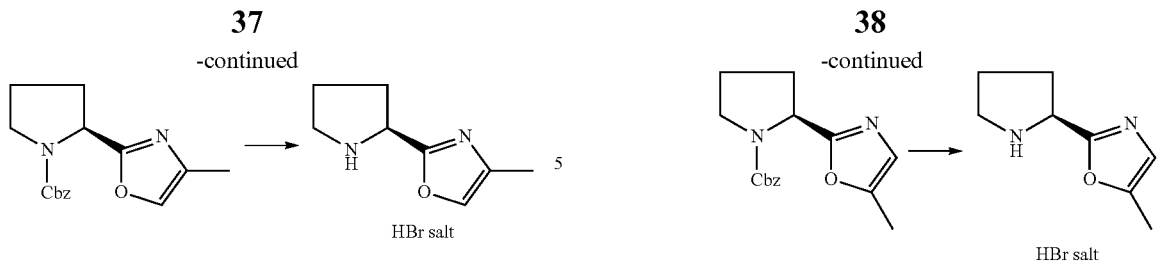

HBr salt

In an analogous manner the HBr salt of 5-methyl-2-(S)-pyrrolidin-2-yl-oxazole may be prepared starting with commercially available Cbz-Pro-OH (synthesis diagram 8). The protected amino acid is coupled to 1-amino-2-propanol using a coupling reagent (EDCI/HOBt, for example) in a suitable solvent (DMF, for example). The aldehyde function may be generated by oxidation with Dess-Martin reagent, or according to Swern (J. Org. Chem. 43, 2480 (1978)). In a manner analogous to WO 2004/113353, the oxazole ring may be closed by cyclocondensation, using hexachloroethane, triphenylphosphine, and triethylamine in dichloromethane. Lastly, the Cbz protective group may be removed by treatment with hydrobromic acid/glacial acetic acid.

SYNTHESIS DIAGRAM 8

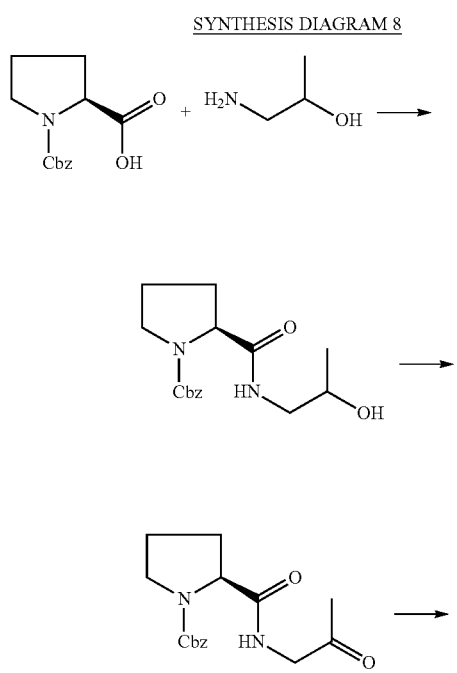

38

Compounds of formula LG-SO$_2$—B are known, for example from the prior art cited above. The sulfonylation of the oxindole nitrogen in (VIII) may be achieved by treatment with sulfonic acid chlorides B—SO$_2$Cl following deprotonation with a strong base, for example potassium tert-butylate or sodium hydride, in a solvent, for example DMF or THF. After cleaving the acetal protective group, for example by treatment with aqueous hydrochloric acid in acetone, the obtained aldehyde (X) may be reacted with primary or secondary amines in the presence of a reducing agent, for example sodium cyanoborohydride or solid phase-bound triacetoxyborohydride, in a solvent, for example THF, to produce the benzylamines (XI) (reductive amination: J. March, Advanced Organic Chemistry, 1992, 4th edition, Wiley, New York, pp. 411; 898). By treating the aldehyde (X) with a reducing agent, for example sodium borohydride, in a solvent, for example MeOH, the corresponding benzyl alcohol may be obtained ($R_A^2$=OH in synthesis diagram 1).

The cyano group as radical $R^1$ may be introduced, starting with the corresponding compounds where $R^1$=iodine, for example by heating compound (VIII) (where $R^1$=I) with zinc cyanide in DMF in the presence of catalytic quantities of palladium tetrakis(triphenylphosphine), or by heating with potassium cyanide and catalytic quantities of palladium tetrakis(triphenylphosphine) in THF (J. Med. Chem. 1996, 39, 5072-5082).

When Y is a chiral radical, compounds (VIII), (IX), (X), and (XI) may be present as a mixture of diastereomers. The two diastereomers may be separated, for example in the case of (VIII) and (X), by chromatography over silica gel, using a suitable eluent such as ethyl acetate in dichloromethane, or methanol in dichloromethane. It is preferred to process compounds (VIII), (IX), and (X) as diastereomerically pure compounds. However, if compounds (XI) according to the invention are present as a mixture of diastereomers, in many cases the diastereomers may be separated by chromatographic methods, for example over silica gel and using a suitable eluent such as methanol in dichloromethane, or by preparative HPLC using a suitable eluent such as acetonitrile in water with small quantities of trifluoroacetic acid.

Further compounds according to the invention may be prepared according to synthesis diagram 9.

SYNTHESIS DIAGRAM 9

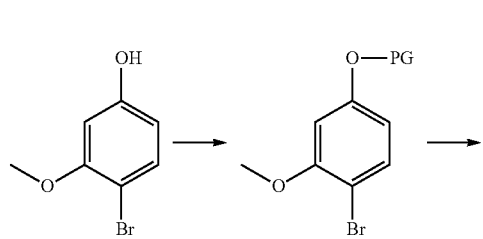

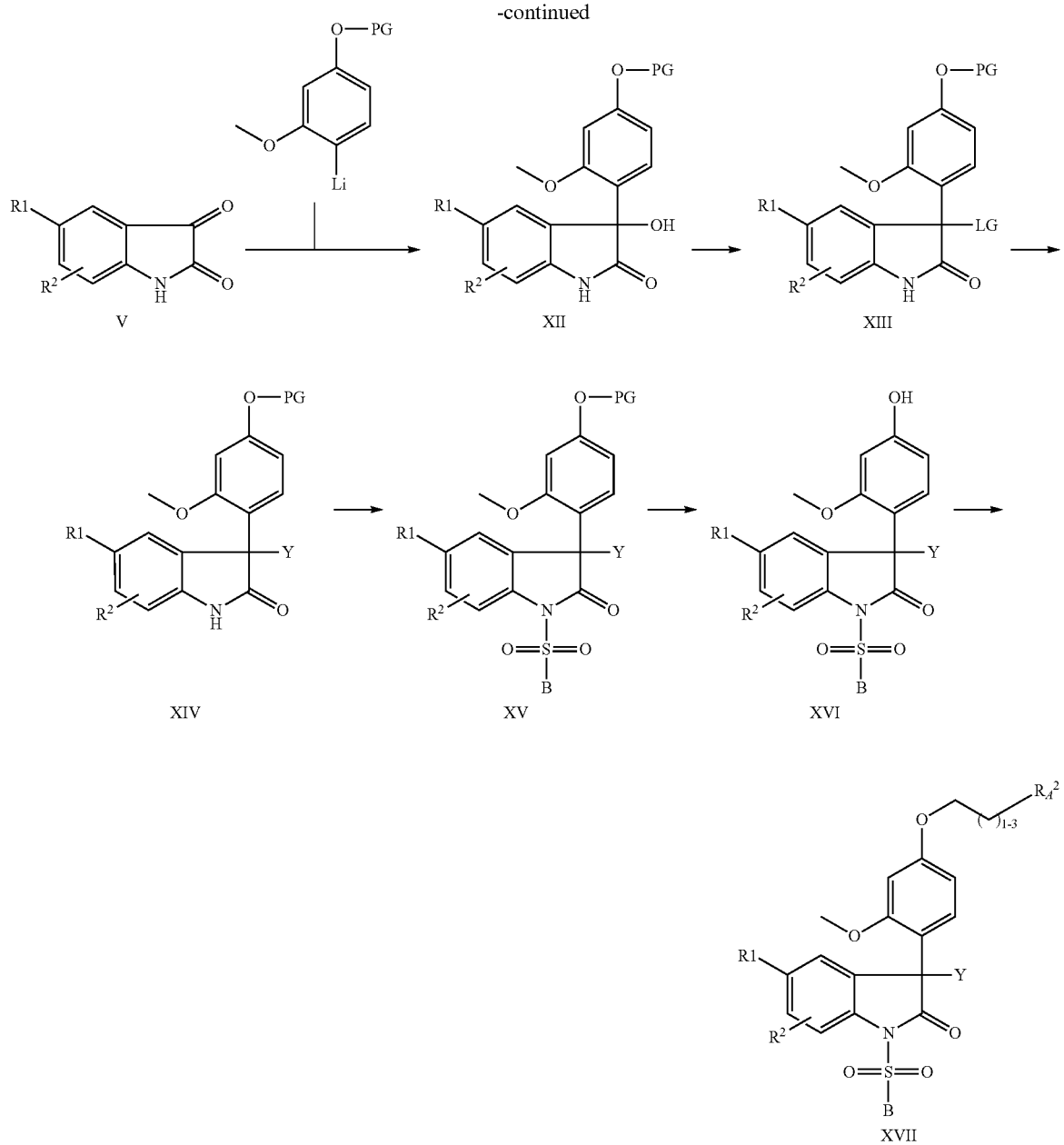

($R_A^{11}$ = OCH$_3$, R$_2$ = H)
PG = Protective group

In the manner shown in synthesis diagram 4, compounds may be synthesized in which an amino group $R_A^2$ is bonded to the ring A via an O-alkyl group. The 3-hydroxyoxindoles (XII) may be prepared by performing addition of organolithium or Grignard compounds at the 3-keto group of the substituted isatines (V). Using $R_A^{11}$=OCH$_3$ as an example, after protection of the phenolic oxygen function using a suitable protective group PG, for example triisopropylsilyl, starting with 4-bromo-3-methoxyphenol the corresponding lithium species may be obtained by treatment with organolithium reagents, for example n-butyl lithium, in an etheric solvent, for example THF, at low temperatures. Introduction of the leaving group LG, substitution of the leaving group LG with amines Y—H, and sulfonylation of the oxindole nitrogen are performed as described above (synthesis diagram 1), and result in the protected compound (XV). After removal of the protective group PG, when PG is triisopropylsilyl, for example, using tetrabutylammonium fluoride in THF, the phenolic oxygen function may be alkylated using alkyl halides containing substituted amino groups $R_A^2$, for example by heating the phenol (XVI) with the alkylation agents $R_A^2$—(C$_2$-C$_3$ alkyl)-Cl in DMF, in the presence of base such as potassium carbonate, in a microwave oven.

The invention is explained in greater detail below with reference to examples, without being limited to the stated examples.

EXPERIMENTAL PORTION

Example 1

5-Chloro-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one, levorotatory diastereomer A) 2-(3-Bromo-4-methoxyphenyl)-5,5-dimethyl-[1,3]dioxane 3-Bromo-4-methoxybenzaldehyde (60.0 g, 279 mmol) was dissolved in toluene (600 mL), and after addition of neopentyl glycol (32.0 g, 306 mmol) and Amberlyst-15 (3.6 g) the reaction mixture was heated under reflux for 2 hours on a water separator. After cooling, the reaction mixture was filtered, washed twice with water, and then concentrated under reduced pressure. The oil residue was combined with heptane, and the product which precipitated was filtered off and washed with heptane. Yield: 57.3 g (68% of theoretical). MS (API-ES, pos) m/z=301, 303 [M+H]$^+$ B) 5-Chloro-3-[5-(5,5-dimethyl-[1,3]dioxan-2-yl)-2-methoxyphenyl]-3-hydroxy-1,3-dihydroindol-2-one Magnesium shavings (2.2 g, 89 mmol) were placed in THF (30 mL) and etched with several iodine crystals. A solution of 2-(3-bromo-4-methoxyphenyl)-5,5-dimethyl[1,3]dioxane (26.0 g, 86 mmol) in THF (80 mL) was added thereto, with stirring. After initiation of the reaction (identifiable by the exothermic evolution of heat), the rate of dropwise addition was decreased so that the reaction mixture was just at the boiling point. The reaction mixture was stirred for an additional 20 min and then was cooled to room temperature. The Grignard solution thus obtained was pumped into an ice-cold solution of the 5-chlorisatin sodium salt (prepared by treating a solution of 5-chlorisatin (13.1 g, 72 mmol) in THF (400 mL) with one equivalent of sodium hydride for one hour at 0° C.), and was then stirred for 5 hours at room temperature. The reaction solution was combined with aqueous ammonium chloride solution, with stirring, and the batch was extracted twice with ethyl acetate. The combined organic phase was washed with water and saturated sodium chloride solution, dried over magnesium sulfate, and concentrated under reduced pressure. Treatment of the residue with diethyl ether resulted in crystallization of the desired product. Yield: 19.2 g (66%) of a white solid. MS (API-ES, pos) m/z=386 [M+H—H$_2$O]$^+$.

C) 5-Chloro-3-[5-(5,5-dimethyl-[1,3]dioxan-2-yl)-2-methoxyphenyl]-3-((S)-2-oxazol-2-yl-pyrrolidin-1-yl)-1,3-dihydroindol-2-one, levorotatory diastereomer A solution of the reaction product according to step B (19.2 g, 26 mmol) in dichloromethane (96 mL) was combined with pyridine (3.03 mL, 37.6 mmol) and thionyl chloride (2.72 mL, 37.3 mmol), with ice cooling, and was stirred at 0° C. for 100 min. The reaction solution was quenched with water, with stirring, and the batch was extracted with dichloromethane. The organic phase was washed with water and saturated sodium chloride solution, dried over magnesium sulfate, and concentrated under reduced pressure. To a solution of the resulting 3-chlorooxindole intermediate in dichloromethane (96 mL) were added N,N-diisopropylethylamine (17.6 mL, 101 mmol), 2-(S)-pyrrolidin-2-yl-oxazole, and HBr salt (5.41 g, 24.7 mmol, prepared according to US 2003/0069223), and the reaction mixture was stirred for 18 hours at room temperature. The reaction mixture was concentrated under reduced pressure, and the residue was divided between ethyl acetate and water. The aqueous phase was extracted again with ethyl acetate. The combined organic phase was washed with water and saturated sodium chloride solution, dried over magnesium sulfate, and concentrated under reduced pressure. The residue was chromatographically purified over silica gel (eluent gradient 40-50% ethyl acetate in dichloromethane). Yield: 3.33 g (25%) of the previously eluted diastereomer. MS (API-ES, pos) m/z=524 [M+H]$^+$; [a]$^{20}_D$ –200, c=0.1 in CHCl$_3$.

D) 5-Chloro-3-[5-(5,5-dimethyl-[1,3]dioxan-2-yl)-2-methoxyphenyl]-1-(4-methoxybenzenesulfonyl)-3-((S)-2-oxazol-2-yl-pyrrolidin-1-yl)-1,3-dihydroindol-2-one A solution of the reaction product according to step C (3.33 g of the previously eluted levorotatory diastereomer, 6.35 mmol) in DMF (30 mL) was combined with sodium hydride (305 mg, 60% dispersion in mineral oil, 7.63 mmol) at 0° C. After 15 min, 4-methoxybenzenesulfonic acid chloride (1.45 g, 6.99 mmol) was added to the reaction solution, with ice cooling, and stirred for an additional 45 min at room temperature. The batch was carefully combined with water and extracted twice with ethyl acetate. The combined organic phase was washed with water and saturated sodium chloride solution, dried over magnesium sulfate, and concentrated under reduced pressure. The residue was chromatographically purified over silica gel (eluent gradient 4-18% ethyl acetate in dichloromethane). Yield: 3.66 g (83%). MS (API-ES, pos) m/z=694 [M+H]$^+$ E) 3-[5-Chloro-1-(4-methoxybenzenesulfonyl)-3-((S)-2-oxazol-2-yl-pyrrolidin-1-yl)-1,3-dihydroindol-2-one-3-yl]-4-methoxybenzaldehyde A solution of the reaction product according to step D (3.66 g, 5.27 mmol) in a mixture of acetone (120 mL) and 2 N aqueous hydrochloric acid (80 mL) was stirred for 4.5 hours at room temperature. The reaction mixture was diluted with dichloromethane and was neutralized by adding 2 N sodium hydroxide solution. The reaction mixture was extracted twice with dichloromethane. The organic phase was washed with water, dried over magnesium sulfate, and concentrated under reduced pressure. Yield: 3.19 g (99%) of a beige solid. MS (API-ES, pos) m/z=608 [M+H]$^+$ F) 5-Chloro-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one, levorotatory diastereomer A solution of the reaction product according to step E (1500 mg, 2.47 mmol) in THF (10 mL) was combined with N-methylpiperazine (0.30 mL, 2.71 mmol) and MP-triacetoxyborohydride resin (Argonaut, 2.80 g, f=2.2 mmol/g, 6.17 mmol) and shaken for 48 hours at room temperature. The solid phase reagent was filtered off and washed with dichloromethane. The organic phase was washed with water, dried with magnesium sulfate, and concentrated under reduced pressure. The residue was chromatographically purified over silica gel (eluent gradient 4-20% methanol in dichloromethane). Yield: 1100 mg (64%); NMR (400 MHz, $d_6$-DMSO) δ=8.05 (d, 2H), 7.90 (br s, 1H), 7.80 (br s, 1H), 7.4 (m, 1H), 7.25 (m, 3H), 7.10 (d, 1H), 7.00 (br s, 1H), 6.85 (s, 1H), 6.80 (d, 1H), 4.80 (m, 1H), 3.85 (s, 3H), 3.00-3.30 (m, 5H), 2.80 (m, 1H), 2.10-2.40 (m, 12H), 1.85 (m, 2H), 1.60 (m, 3H); MS (API-ES, pos) m/z=692 [M+H]$^+$; [a]$^{20}_D$-188, c=0.1 in CHCl$_3$.

Example 2

5-Chloro-3-(5-hydroxymethyl-2-methoxyphenyl)-1-(4-methoxybenzenesulfonyl)-3-((S)-2-oxazol-2-yl-pyrrolidin-1-yl)-1,3-dihydroindol-2-one The benzyl alcohol was prepared in a manner analogous to Example 1, with omission of N-methylpiperazine as reactant in step F. MS (API-ES, pos) m/z=610 [M+H]$^+$ In a manner analogous to that described in Example 1, and using the synthesis steps described in synthesis diagram 1, the following compounds 3 through 43 were prepared in diastereomerically pure form. In some cases the compounds were purified by preparative reverse-phase HPLC (eluent: gradient of 10% to 80% acetonitrile in water, 0.1% trifluoroacetic acid or 0.2% acetic acid as modulator), and when the compounds contained a basic nitrogen in the molecule, precipitated as trifluoroacetic acid salts or acetic acid salts, respectively.

Example 3

5-Chloro-1-(4-methoxybenzenesulfonyl)-3-(2-methoxy-5-methylaminomethylphenyl)-3-((S)-2-oxazol-2-yl-pyrrolidin-1-yl)-1,3-dihydroindol-2-one, trifluoroacetic acid salt MS (API-ES, pos) m/z=623 [M+H]$^+$ Example 4

5-Chloro-3-(5-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one MS (API-ES, pos) m/z=637 [M+H]$^+$ Example 5

5-Chloro-3-(5-ethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=637 [M+H]$^+$ Example 6

5-Chloro-3-{5-[(ethylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=651 [M+H]$^+$ Example 7

5-Chloro-3-(5-diethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=665 [M+H]$^+$ Example 8

5-Chloro-3-[5-(isopropylaminomethyl)-2-methoxyphenyl]-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=651 [M+H]$^+$ Example 9

5-Chloro-3-{5-[(isopropylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=665 [M+H]$^+$ Example 10

5-Chloro-3-{5-[(2-hydroxyethylamino)methyl]-2-methoxyphenyl}-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=653 [M+H]$^+$ Example 11

5-Chloro-1-(4-methoxybenzenesulfonyl)-3-(2-methoxy-5-piperazin-1-ylmethylphenyl)-3-((S)-2-oxazol-2-yl-pyrrolidin-1-yl)-1,3-dihydroindol-2-one MS (API-ES, pos) m/z=678 [M+H]$^+$ Example 12

3-(5-Azetidin-1-ylmethyl-2-methoxy-phenyl)-5-chloro-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=649 [M+H]$^+$ Example 13

5-Chloro-1-(4-methoxybenzenesulfonyl)-3-(2-methoxy-5-pyrrolidin-1-ylmethylphenyl)-3-((S)-2-oxazol-2-yl-pyrrolidin-1-yl)-1,3-dihydroindol-2-one MS (API-ES, pos) m/z=663 [M+H]$^+$ Example 14

5-Chloro-1-(4-methoxybenzenesulfonyl)-3-(2-methoxy-5-piperidin-1-ylmethylphenyl)-3-((S)-2-oxazol-2-yl-pyrrolidin-1-yl)-1,3-dihydroindol-2-one, trifluoroacetic acid salt MS (API-ES, pos) m/z=677 [M+H]$^+$ Example 15

5-Chloro-3-(4-hydroxymethyl-2-methoxyphenyl)-1-(4-methoxybenzenesulfonyl)-3-((S)-2-oxazol-2-yl-pyrrolidin-1-yl)-1,3-dihydroindol-2-one MS (API-ES, pos) m/z=610 [M+H]$^+$ Example 16

5-Chloro-1-(4-methoxybenzenesulfonyl)-3-(2-methoxy-4-methylaminomethylphenyl)-3-((S)-2-oxazol-2-yl-pyrrolidin-1-yl)-1,3-dihydroindol-2-one, trifluoroacetic acid salt
MS (API-ES, pos) m/z=623 [M+H]$^+$

Example 17

5-Chloro-3-4-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=637 [M+H]$^+$

Example 18

5-Chloro-3-[(4-[(ethylmethylamino)methyl]-2-methoxyphenyl]-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=651 [M+H]$^+$

Example 19

5-Chloro-3-(4-diethylaminomethyl-2-methoxyphenyl)-1-(4-methoxybenzenesulfonyl)-3-((S)-2-oxazol-2-yl-pyrrolidin-1-yl)-1,3-dihydroindol-2-one, acetic acid salt MS (API-ES, pos) m/z=665 [M+H]$^+$

Example 20

5-Chloro-1-(4-methoxybenzenesulfonyl)-3-(2-methoxy-4-propylaminomethylphenyl)-3-((S)-2-oxazol-2-yl-pyrrolidin-1-yl)-1,3-dihydroindol-2-one, trifluoroacetic acid salt MS (API-ES, pos) m/z=651 [M+H]$^+$

Example 21

5-Chloro-3-[(4-[(isopropylmethylamino)methyl]-2-methoxyphenyl]-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=665 [M+H]$^+$

Example 22

5-Chloro-1-(4-methoxybenzenesulfonyl)-3-(2-methoxy-4-{[(2-methoxyethyl)methylamino]methyl}phenyl)-3-((S)-2-oxazol-2-yl-pyrrolidin-1-yl)-1,3-dihydroindol-2-one, trifluoroacetic acid salt MS (API-ES, pos) m/z=681 [M+H]$^+$

Example 23

5-Chloro-1-(4-methoxybenzenesulfonyl)-3-[2-methoxy-4-(4-methylpiperazin-1-ylmethyl)phenyl]-3-((S)-2-oxazol-2-yl-pyrrolidin-1-yl)-1,3-dihydroindol-2-one, trifluoroacetic acid salt MS (API-ES, pos) m/z=692 [M+H]$^+$

Example 24

5-Chloro-1-(4-methoxybenzenesulfonyl)-3-(2-methoxy-4-piperazin-1-ylmethylphenyl)-3-((S)-2-oxazol-2-yl-pyrrolidin-1-yl)-1,3-dihydroindol-2-one, trifluoroacetic acid salt MS (API-ES, pos) m/z=678 [M+H]$^+$

Example 25

5-Chloro-1-(4-methoxybenzenesulfonyl)-3-(2-methoxy-4-pyrrolidin-1-ylmethylphenyl)-3-((S)-2-oxazol-2-yl-pyrrolidin-1-yl)-1,3-dihydroindol-2-one MS (API-ES, pos) m/z=663 [M+H]$^+$

Example 26

5-Chloro-1-(4-methoxybenzenesulfonyl)-3-(2-methoxy-4-piperidin-1-ylmethylphenyl)-3-((S)-2-oxazol-2-yl-pyrrolidin-1-yl)-1,3-dihydroindol-2-one MS (API-ES, pos) m/z=677 [M+H]$^+$

Example 27

6-Chloro-3-(5-hydroxymethyl-2-methoxyphenyl)-1-(4-methoxybenzenesulfonyl)-3-((S)-2-oxazol-2-yl-pyrrolidin-1-yl)-1,3-dihydroindol-2-one MS (API-ES, pos) m/z=610 [M+H]$^+$

Example 28

6-Chloro-3-(5-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=637 [M+H]$^+$

Example 29

6-Chloro-3-(5-ethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=637 [M+H]$^+$

Example 30

6-Chloro-3-{5-[(ethylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=651 [M+H]$^+$

Example 31

6-Chloro-3-(5-diethylaminomethyl-2-methoxyphenyl)-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=665 [M+H]$^+$

Example 32

6-Chloro-1-(4-methoxybenzenesulfonyl)-3-(2-methoxy-5-propylaminomethylphenyl)-3-((S)-2-oxazol-2-yl-pyrrolidin-1-yl)-1,3-dihydroindol-2-one, trifluoroacetic acid salt MS (API-ES, pos) m/z=651 [M+H]$^+$

Example 33

6-Chloro-3-{5-[(isopropylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=665 [M+H]$^+$

Example 34

6-Chloro-1-(4-methoxybenzenesulfonyl)-3-(2-methoxy-5-{[(2-methoxyethyl)methylamino]methyl}phenyl)-3-((S)-2-oxazol-2-yl-pyrrolidin-1-yl)-1,3-dihydroindol-2-one, trifluoroacetic acid salt MS (API-ES, pos) m/z=681 [M+H]$^+$

Example 35

6-Chloro-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one, trifluoroacetic acid salt MS (API-ES, pos) m/z=692 [M+H]$^+$

Example 36

6-Chloro-1-(4-methoxybenzenesulfonyl)-3-(2-methoxy-5-piperazin-1-ylmethylphenyl)-3-((S)-2-oxazol-2-yl-pyrrolidin-1-yl)-1,3-dihydroindol-2-one, trifluoroacetic acid salt MS (API-ES, pos) m/z=678 [M+H]$^+$

Example 37

6-Chloro-1-(4-methoxybenzenesulfonyl)-3-(2-methoxy-5-morpholin-4-ylmethylphenyl)-3-((S)-2-oxazol-2-yl-pyrrolidin-1-yl)-1,3-dihydroindol-2-one, trifluoroacetic acid salt MS (API-ES, pos) m/z=679 [M+H]$^+$

Example 38

3-(5-Azetidin-1-ylmethyl-2-methoxyphenyl)-6-chloro-1-(4-methoxybenzenesulfonyl)-3-((S)-2-oxazol-2-yl-pyrrolidin-1-yl)-1,3-dihydroindol-2-one, trifluoroacetic acid salt MS (API-ES, pos) m/z=649 [M+H]$^+$

Example 39

6-Chloro-1-(4-methoxybenzenesulfonyl)-3-(2-methoxy-5-pyrrolidin-1-ylmethylphenyl)-3-((S)-2-oxazol-2-yl-pyrrolidin-1-yl)-1,3-dihydroindol-2-one, trifluoroacetic acid salt MS (API-ES, pos) m/z=663 [M+H]$^+$

Example 40

6-Chloro-1-(4-methoxybenzenesulfonyl)-3-(2-methoxy-5-piperidin-1-ylmethylphenyl)-3-((S)-2-oxazol-2-yl-pyrrolidin-1-yl)-1,3-dihydroindol-2-one, trifluoroacetic acid salt MS (API-ES, pos) m/z=677 [M+H]$^+$

Example 41

5-Cyano-3-(4-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one MS (API-ES, pos) m/z=628 [M+H]$^+$

Example 42

5-Cyano-1-(4-methoxybenzenesulfonyl)-3-[2-methoxy-4-(4-methylpiperazin-1-ylmethyl)phenyl]-3-((S)-2-oxazol-2-yl-pyrrolidin-1-yl)-1,3-dihydroindol-2-one, trifluoroacetic acid salt MS (API-ES, pos) m/z=683 [M+H]$^+$

Example 43

5-Cyano-1-(4-methoxybenzenesulfonyl)-3-(2-methoxy-4-morpholin-4-ylmethylphenyl)-3-((S)-2-oxazol-2-yl-pyrrolidin-1-yl)-1,3-dihydroindol-2-one, trifluoroacetic acid salt MS (API-ES, pos) m/z=670 [M+H]$^+$ In an analogous manner the following compounds may be prepared in diastereomerically pure form, using the synthesis steps described in synthesis diagram 1 and using the correspondingly substituted starting compounds:

Example 44

5-Cyano-3-(5-hydroxymethyl-2-methoxyphenyl)-1-(4-methoxybenzenesulfonyl)-3-((S)-2-oxazol-2-yl-pyrrolidin-1-yl)-1,3-dihydroindol-2-one

Example 45

5-Cyano-1-(4-methoxybenzenesulfonyl)-3-(2-methoxy-5-methylaminomethylphenyl)-3-((S)-2-oxazol-2-yl-pyrrolidin-1-yl)-1,3-dihydroindol-2-one; MS (API-ES, pos) m/z=614 [M+H]$^+$

Example 46

5-Cyano-3-(5-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=628 [M+H]$^+$

Example 47

5-Cyano-3-(5-ethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=628 [M+H]$^+$

Example 48

5-Cyano-3-{5-[(ethylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one; MS (API-ES, pos) m/z=642 [M+H]$^+$

Example 49

5-Cyano-3-(5-diethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=656 [M+H]$^+$

Example 50

5-Cyano-1-(4-methoxybenzenesulfonyl)-3-(2-methoxy-5-propylaminomethylphenyl)-3-((S)-2-oxazol-2-yl-pyrrolidin-1-yl)-1,3-dihydroindol-2-one; MS (API-ES, pos) m/z=642 [M+H]$^+$

Example 51

5-Cyano-1-(4-methoxybenzenesulfonyl)-3-{2-methoxy-5-[(methylpropylamino)methyl]phenyl}-3-((S)-2-oxazol-2-yl-pyrrolidin-1-yl)-1,3-dihydroindol-2-one

Example 52

5-Cyano-3-[5-(isopropylaminomethyl)-2-methoxyphenyl]-1-(4-methoxybenzenesulfonyl)-3-((S)-2-oxazol-2-yl-pyrrolidin-1-yl)-1,3-dihydroindol-2-one; MS (API-ES, pos) m/z=642 [M+H]$^+$

Example 53

5-Cyano-3-{5-[(isopropylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one; MS (API-ES, pos) m/z=656 [M+H]$^+$

Example 54

5-Cyano-3-{5-[(2-hydroxyethylamino)methyl]-2-methoxyphenyl}-1-(4-methoxybenzenesulfonyl)-3-((S)-2-oxazol-2-yl-pyrrolidin-1-yl)-1,3-dihydroindol-2-one; MS (API-ES, pos) m/z=644 [M+H]$^+$

Example 55

5-Cyano-1-(4-methoxybenzenesulfonyl)-3-(2-methoxy-5-{[(2-methoxyethyl)methylamino]methyl}phenyl)-3-((S)-2-oxazol-2-yl-pyrrolidin-1-yl)-1,3-dihydroindol-2-one; MS (API-ES, pos) m/z=672 [M+H]$^+$

Example 56

5-Cyano-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=683 [M+H]$^+$

Example 57

5-Cyano-1-(4-methoxybenzenesulfonyl)-3-(2-methoxy-5-piperazin-1-ylmethylphenyl)-3-((S)-2-oxazol-2-yl-pyrrolidin-1-yl)-1,3-dihydroindol-2-one; MS (API-ES, pos) m/z=669 [M+H]$^+$

Example 58

5-Cyano-1-(4-methoxybenzenesulfonyl)-3-(2-methoxy-5-morpholin-4-ylmethylphenyl)-3-((S)-2-oxazol-2-yl-pyrrolidin-1-yl)-1,3-dihydroindol-2-one; MS (API-ES, pos) m/z=670 [M+H]$^+$

Example 59

3-(5-Azetidin-1-ylmethyl-2-methoxyphenyl)-5-cyano-1-(4-methoxybenzenesulfonyl)-3-((S)-2-oxazol-2-yl-pyrrolidin-1-yl)-1,3-dihydroindol-2-one

Example 60

5-Cyano-1-(4-methoxybenzenesulfonyl)-3-(2-methoxy-5-pyrrolidin-1-ylmethylphenyl)-3-((S)-2-oxazol-2-yl-pyrrolidin-1-yl)-1,3-dihydroindol-2-one; MS (API-ES, pos) m/z=654 [M+H]$^+$

Example 61

5-Cyano-1-(4-methoxybenzenesulfonyl)-3-(2-methoxy-5-piperidin-1-ylmethylphenyl)-3-((S)-2-oxazol-2-yl-pyrrolidin-1-yl)-1,3-dihydroindol-2-one; MS (API-ES, pos) m/z=668 [M+H]$^+$

Example 62

5,6-Dichloro-3-(5-hydroxymethyl-2-methoxyphenyl)-1-(4-methoxybenzenesulfonyl)-3-((S)-2-oxazol-2-yl-pyrrolidin-1-yl)-1,3-dihydroindol-2-one

Example 63

5,6-Dichloro-1-(4-methoxybenzenesulfonyl)-3-(2-methoxy-5-methylaminomethylphenyl)-3-((S)-2-oxazol-2-yl-pyrrolidin-1-yl)-1,3-dihydroindol-2-one; MS (API-ES, pos) m/z=657 [M+H]$^+$

Example 64

5,6-Dichloro-3-(5-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=671 [M+H]$^+$

Example 65

5,6-Dichloro-3-(5-ethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=671 [M+H]$^+$

Example 66

5,6-Dichloro-3-{5-[(ethylmethylamino)methyl]-2-methoxyphenyl}-1-(4-methoxybenzenesulfonyl)-3-((S)-2-oxazol-2-yl-pyrrolidin-1-yl)-1,3-dihydroindol-2-one

Example 67

5,6-Dichloro-3-(5-diethylaminomethyl-2-methoxyphenyl)-1-(4-methoxybenzenesulfonyl)-3-((S)-2-oxazol-2-yl-pyrrolidin-1-yl)-1,3-dihydroindol-2-one

Example 68

5,6-Dichloro-1-(4-methoxybenzenesulfonyl)-3-(2-methoxy-5-propylaminomethylphenyl)-3-((S)-2-oxazol-2-yl-pyrrolidin-1-yl)-1,3-dihydroindol-2-one; MS (API-ES, pos) m/z=685 [M+H]$^+$

Example 69

5,6-Dichloro-1-(4-methoxybenzenesulfonyl)-3-{2-methoxy-5-[(methylpropylamino)methyl]phenyl}-3-((S)-2-oxazol-2-yl-pyrrolidin-1-yl)-1,3-dihydroindol-2-one

Example 70

5,6-Dichloro-3-[5-(isopropylaminomethyl)-2-methoxyphenyl]-1-(4-methoxybenzenesulfonyl)-3-((S)-2-oxazol-2-yl-pyrrolidin-1-yl)-1,3-dihydroindol-2-one; MS (API-ES, pos) m/z=685 [M+H]$^+$

Example 71

5,6-Dichloro-3-{5-[(isopropylmethylamino)methyl]-2-methoxyphenyl}-1-(4-ethoxybenzenesulfonyl)-3-((S)-2-oxazol-2-yl-pyrrolidin-1-yl)-1,3-dihydroindol-2-one

Example 72

5,6-Dichloro-3-{5-[(2-hydroxyethylamino)methyl]-2-methoxyphenyl}-1-(4-ethoxybenzenesulfonyl)-3-((S)-2-oxazol-2-yl-pyrrolidin-1-yl)-1,3-dihydro-indol-2-one

Example 73

5,6-Dichloro-1-(4-methoxybenzenesulfonyl)-3-(2-methoxy-5-{[(2-methoxyethyl)methylamino]methyl}phenyl)-3-((S)-2-oxazol-2-yl-pyrrolidin-1-yl)-1,3-dihydro-indol-2-one

Example 74

5,6-Dichloro-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=726 [M+H]+

Example 75

5,6-Dichloro-1-(4-methoxybenzenesulfonyl)-3-(2-methoxy-5-piperazin-1-ylmethylphenyl)-3-((S)-2-oxazol-2-yl-pyrrolidin-1-yl)-1,3-dihydroindol-2-one

Example 76

5,6-Dichloro-1-(4-methoxybenzenesulfonyl)-3-(2-methoxy-5-morpholin-4-ylmethylphenyl)-3-((S)-2-oxazol-2-yl-pyrrolidin-1-yl)-1,3-dihydroindol-2-one

Example 77

3-(5-Azetidin-1-ylmethyl-2-methoxyphenyl)-5,6-dichloro-1-(4-methoxybenzenesulfonyl)-3-((S)-2-oxazol-2-yl-pyrrolidin-1-yl)-1,3-dihydroindol-2-one

Example 78

5,6-Dichloro-1-(4-methoxybenzenesulfonyl)-3-(2-methoxy-5-pyrrolidin-1-ylmethylphenyl)-3-((S)-2-oxazol-2-yl-pyrrolidin-1-yl)-1,3-dihydroindol-2-one; MS (API-ES, pos) m/z=697 [M+H]+

Example 79

5,6-Dichloro-1-(4-methoxybenzenesulfonyl)-3-(2-methoxy-5-piperidin-1-ylmethylphenyl)-3-((S)-2-oxazol-2-yl-pyrrolidin-1-yl)-1,3-dihydroindol-2-one

Example 80

5-Chloro-1-(4-ethoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=706 [M+H]+

Example 81

5-Chloro-1-(4-cyanobenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=687 [M+H]+

Example 82

5-Chloro-1-(4-fluorobenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=680 [M+H]+

Example 83

5-Chloro-1-(4-chlorobenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one

Example 84

1-(Benzenesulfonyl)-5-chloro-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=662 [M+H]+

Example 85

5-Chloro-1-(4-ethylbenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=690 [M+H]+

Example 86

5-Chloro-1-(2,4-dimethoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=722 [M+H]+

Example 87

5-Chloro-1-(3-fluoro-4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=710 [M+H]+

Example 88

5-Chloro-3-[5-(4-ethylpiperazin-1-ylmethyl)-2-methoxyphenyl]-1-(4-methoxybenzenesulfanyl)-3-((S)-2-oxazol-2-yl-pyrrolidin-1-yl)-1,3-dihydroindol-2-one; MS (API-ES, pos) m/z=706 [M+H]+

Example 89

5-Chloro-3-[5-(4-isopropylpiperazin-1-ylmethyl)-2-methoxyphenyl]-1-(4-ethoxybenzenesulfonyl)-3-((S)-2-oxazol-2-yl-pyrrolidin-1-yl)-1,3-dihydroindol-2-one; MS (API-ES, pos) m/z=720 [M+H]+

Example 90

3-[5-(4-Acetylpiperazin-1-ylmethyl)-2-methoxyphenyl]-5-chloro-1-(4-methoxybenzenesulfonyl)-3-((S)-2-oxazol-2-yl-pyrrolidin-1-yl)-1,3-dihydroindol-2-one; MS (API-ES, pos) m/z=720 [M+H]+

Example 91

5-Chloro-1-(4-methoxybenzenesulfonyl)-3-[2-methoxy-5-(4-methyl-[1,4]diazepan-1-ylmethyl)phenyl]-3-((S)-2-oxazol-2-yl-pyrrolidin-1-yl)-1,3-dihydroindol-2-one; MS (API-ES, pos) m/z=706 [M+H]+

Example 92

5-Chloro-3-{5-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=722 [M+H]$^+$

Example 93

6-Chloro-3-{5-[(2-hydroxyethylamino)methyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=653 [M+H]$^+$

Example 94

5-Cyano-3-[5-(4-isopropylpiperazin-1-ylmethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=711 [M+H]$^+$

Example 95

5-Cyano-3-[5-(4-acetylpiperazin-1-ylmethyl)-2-methoxyphenyl]-1-(4-methoxybenzenesulfonyl)-3-((S)-2-oxazol-2-yl-pyrrolidin-1-yl)-1,3-dihydroindol-2-one; MS (API-ES, pos) m/z=711 [M+H]$^+$

Example 96

5-Chloro-1-(4-methoxybenzenesulfonyl)-3-(2-methoxy-5-(morpholin-4-ylmethyl)phenyl)-3-((S)-2-oxazol-2-yl-pyrrolidin-1-yl)-1,3-dihydroindol-2-one; MS (API-ES, pos) m/z=679 [M+H]$^+$

Example 97

5-Cyano-1-(4-methoxybenzenesulfonyl)-3-(2-methoxy-4-methylaminomethylphenyl)-3-((S)-2-oxazol-2-yl-pyrrolidin-1-yl)-1,3-dihydroindol-2-one; trifluoroacetic acid salt; MS (API-ES, pos) m/z=614 [M+H]$^+$

Example 98

5-Cyano-3-(4-ethylaminomethyl-2-methoxyphenyl)-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=628 [M+H]$^+$

Example 99

5-Cyano-1-(4-methoxybenzenesulfonyl)-3-(2-methoxy-4-(propylaminomethyl)phenyl)-3-((S)-2-oxazol-2-yl-pyrrolidin-1-yl)-1,3-dihydroindol-2-one; trifluoroacetic acid salt; MS (API-ES, pos) m/z=642 [M+H]$^+$

Example 100

5-Cyano-3-[4-(isopropylaminomethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=642 [M+H]$^+$

Example 101

5-Cyano-1-(4-methoxybenzenesulfonyl)-3-(2-methoxy-4-(pyrrolidin-1-ylmethyl)phenyl)-3-((S)-2-oxazol-2-yl-pyrrolidin-1-yl)-1,3-dihydroindol-2-one; trifluoroacetic acid salt; MS (API-ES, pos) m/z=254 [M+H]$^+$

Example 102

5-Chloro-3-(5-dimethylaminomethyl-2-methoxyphenyl)-3-((2S,4R)-4-hydroxy-2-oxazol-2-yl-pyrrolidin-1-yl)-1-(4-methoxybenzenesulfonyl)-1,3-dihydroindol-2-one; trifluoroacetic acid salt; MS (API-ES, pos) m/z=653 [M+H]$^+$

Example 103

5-Chloro-3-((2S,4R)-4-hydroxy-2-oxazol-2-yl-pyrrolidin-1-yl)-1-(4-methoxybenzenesulfonyl)-3-[2-methoxy-5-(4-methylpiperazin-1-ylmethyl)phenyl]-1,3-dihydroindol-2-one; trifluoroacetic acid salt; MS (API-ES, pos) m/z=708 [M+H]$^+$

Example 104

5,6-Dichloro-3-[5-(4-isopropylpiperazin-1-ylmethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=754 [M+H]$^+$

Example 105

5-Chloro-3-((2S,4R)-4-hydroxy-2-oxazol-2-yl-pyrrolidin-1-yl)-1-(4-methoxybenzenesulfonyl)-3-(2-methoxy-5-(methylaminomethyl)phenyl)-1,3-dihydroindol-2-one; trifluoroacetic acid salt; MS (API-ES, pos) m/z=639 [M+H]$^+$

Example 106

5,6-Dichloro-3-[5-(tert-butylaminomethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=699 [M+H]$^+$

Example 107

5,6-Dichloro-3-{5-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=756 [M+H]$^+$

Example 108

5-Chloro-3-(5-dimethylaminomethyl-2-methoxyphenyl)-1-(4-methoxybenzenesulfonyl)-3-[(oxazol-2-ylmethyl)amino]-1,3-dihydroindol-2-one; trifluoroacetic acid salt; MS (API-ES, pos) m/z=597 [M+H]$^+$

Example 109

5-Chloro-1-(4-methoxybenzenesulfonyl)-3-(2-methoxy-5-pyrrolidin-1-ylmethylphenyl)-3-[(oxazol-2-ylmethyl)amino]-1,3-dihydroindol-2-one; trifluoroacetic acid salt; MS (API-ES, pos) m/z=623 [M+H]$^+$

Example 110

5-Chloro-1-(4-methoxybenzenesulfonyl)-3-[2-methoxy-5-(4-methylpiperazin-1-ylmethyl)phenyl]-3-[(oxazol-2-ylmethyl)amino]-1,3-dihydroindol-2-one; trifluoroacetic acid salt; MS (API-ES, pos) m/z=652 [M+H]$^+$

Example 111

5-Chloro-3-{5-[(2-hydroxyethylamino)methyl]-2-methoxyphenyl}-1-(4-methoxybenzenesulfonyl)-3-[(oxazol-2-ylmethyl)amino]-1,3-dihydroindol-2-one; trifluoroacetic acid salt; MS (API-ES, pos) m/z=613 [M+H]$^+$

Example 112

5-Chloro-1-(3-bromo-4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; MS (API-ES, pos) m/z=770 [M+H]$^+$

Example 113

5-Chloro-3-((2S,4R)-4-hydroxy-2-oxazol-2-yl-pyrrolidin-1-yl)-1-(4-methoxybenzenesulfonyl)-3-(2-methoxy-5-(piperazin-1-ylmethyl)phenyl)-1,3-dihydroindol-2-one; MS (API-ES, pos) m/z=694 [M+H]$^+$

Example 114

5-Chloro-3-((2S,4R)-4-hydroxy-2-oxazol-2-yl-pyrrolidin-1-yl)-1-(4-methoxybenzenesulfonyl)-3-(2-methoxy-5-(pyrrolidin-1-ylmethyl)phenyl)-1,3-dihydroindol-2-one; trifluoroacetic acid salt; MS (API-ES, pos) m/z=679 [M+H]$^+$

Example 115

5-Chloro-3-((2S,4R)-4-hydroxy-2-oxazol-2-yl-pyrrolidin-1-yl)-1-(4-methoxybenzenesulfonyl)-3-(2-methoxy-5-(propylaminomethyl)phenyl)-1,3-dihydroindol-2-one; trifluoroacetic acid salt; MS (API-ES, pos) m/z=667 [M+H]$^+$

Example 116

5-Chloro-1-(4-methoxybenzenesulfonyl)-3-(2-methoxy-5-(propylaminomethyl)phenyl)-3-((S)-2-oxazol-2-yl-pyrrolidin-1-yl)-1,3-dihydroindol-2-one; trifluoroacetic acid salt; MS (API-ES, pos) m/z=651 [M+H]$^+$

Example 117

5-Chloro-3-(5-dimethylaminomethyl-2-methoxyphenyl)-1-(4-methoxybenzenesulfonyl)-3-(2-thiazol-2-yl-pyrrolidin-1-yl)-1,3-dihydroindol-2-one; trifluoroacetic acid salt; MS (API-ES, pos) m/z=653 [M+H]$^+$

Example 118

5-Chloro-1-(4-methoxybenzenesulfonyl)-3-(2-methoxy-5-(pyrrolidin-1-ylmethyl)phenyl)-3-(2-thiazol-2-yl-pyrrolidin-1-yl)-1,3-dihydroindol-2-one; trifluoroacetic acid salt; MS (API-ES, pos) m/z=679 [M+H]$^+$

Example 119

5-Chloro-1-(4-methoxybenzenesulfonyl)-3-[2-methoxy-5-(4-methylpiperazin-1-ylmethyl)phenyl]-3-(2-thiazol-2-yl-pyrrolidin-1-yl)-1,3-dihydroindol-2-one; trifluoroacetic acid salt; MS (API-ES, pos) m/z=708 [M+H]$^+$

Example 120

5-Chloro-1-(4-methoxybenzenesulfonyl)-3-(2-methoxy-5-methylaminomethylphenyl)-3-(2-pyridin-2-yl-pyrrolidin-1-yl)-1,3-dihydroindol-2-one; trifluoroacetic acid salt; MS (API-ES, pos) m/z=633 [M+H]$^+$

Example 121

5-Chloro-1-(4-methoxybenzenesulfonyl)-3-(2-methoxy-5-(piperazin-1-ylmethyl)phenyl)-3-(2-thiazol-2-yl-pyrrolidin-1-yl)-1,3-dihydroindol-2-one; trifluoroacetic acid salt; MS (API-ES, pos) m/z=694 [M+H]$^+$

Example 122

5-Chloro-3-(5-dimethylaminomethyl-2-methoxyphenyl)-1-(4-methoxybenzenesulfonyl)-3-(2-pyridin-2-yl-pyrrolidin-1-yl)-1,3-dihydroindol-2-one; trifluoroacetic acid salt; MS (API-ES, pos) m/z=647 [M+H]$^+$

Example 123

5-Chloro-1-(4-methoxybenzenesulfonyl)-3-(2-methoxy-5-propylaminomethylphenyl)-3-(2-Pyridin-2-yl-pyrrolidin-1-yl)-1,3-dihydroindol-2-one; trifluoroacetic acid salt; MS (API-ES, pos) m/z=661 [M+H]$^+$

Example 124

5-Chloro-1-(4-methoxybenzenesulfonyl)-3-[2-methoxy-5-(4-methylpiperazin-1-ylmethyl)phenyl]-3-(2-pyridin-2-yl-pyrrolidin-1-yl)-1,3-dihydroindol-2-one; trifluoroacetic acid salt; MS (API-ES, pos) m/z=702 [M+H]$^+$

Example 125

5-Chloro-1-(4-methoxybenzenesulfonyl)-3-[2-methoxy-5-(3-oxopiperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=692 [M+H]$^+$

Example 126

5-Chloro-1-(4-methoxybenzenesulfonyl)-3-(2-methoxy-5-piperazin-1-ylmethylphenyl)-3-(2-pyridin-2-yl-pyrrolidin-1-yl)-1,3-dihydroindol-2-one; trifluoroacetic (2S,4R) acid salt; MS (API-ES, pos) m/z=688 [M+H]$^+$

Example 127

5-Chloro-3-{4-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=722 [M+H]$^+$

Example 128

5-Chloro-1-(4-methoxybenzenesulfonyl)-3-[2-methoxy-5-(4-methylpiperazin-1-ylmethyl)phenyl]-3-((S)-1-oxazol-2-yl-ethylamino)-1,3-dihydroindol-2-one; trifluoroacetic acid salt; MS (API-ES, pos) m/z=666 [M+H]$^+$

Example 129

5-Chloro-1-(4-methoxybenzenesulfonyl)-3-(2-methoxy-5-methylaminomethylphenyl)-3-[(oxazol-2-ylmethyl)amino]-1,3-dihydroindol-2-one; trifluoroacetic acid salt; MS (API-ES, pos) m/z=583 [M+H]$^+$

Example 130

5-Chloro-1-(4-methoxybenzenesulfonyl)-3-{2-methoxy-5-[(2,2,2-trifluoroethylamino)methyl]phenyl}-3-((S)-2-oxazol-2-yl-pyrrolidin-1-yl)-1,3-dihydroindol-2-one; trifluoroacetic acid salt; MS (API-ES, pos) m/z=691 [M+H]$^+$

Example 131

5-Chloro-3-(4-ethylaminomethyl-2-methoxyphenyl)-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=637 [M+H]$^+$

Example 132

5-Chloro-1-(4-methoxybenzenesulfonyl)-3-(2-methoxy-5-propylaminomethylphenyl)-3-(2-thiazol-2-yl-pyrrolidin-1-yl)-1,3-dihydroindol-2-one; trifluoroacetic acid salt; MS (API-ES, pos) m/z=667 [M+H]$^+$

Example 133

5-Chloro-3-(5-dimethylaminomethyl-2-methoxyphenyl)-1-(4-methoxybenzenesulfonyl)-3-((S)-1-oxazol-2-yl-ethylamino)-1,3-dihydroindol-2-one; trifluoroacetic acid salt; MS (API-ES, pos) m/z=611 [M+H]$^+$

Example 134

5-Chloro-1-(4-methoxybenzenesulfonyl)-3-(2-methoxy-5-propylaminomethylphenyl)-3-((S)-1-oxazol-2-yl-ethylamino)-1,3-dihydroindol-2-one; trifluoroacetic acid salt; MS (API-ES, pos) m/z=625 [M+H]$^+$

Example 135

5-Chloro-1-(4-methoxybenzenesulfonyl)-3-(2-methoxy-5-(piperazin-1-ylmethyl)phenyl)-3-((S)-1-oxazol-2-yl-ethylamino)-1,3-dihydroindol-2-one; trifluoroacetic acid salt; MS (API-ES, pos) m/z=652 [M+H]$^+$

Example 136

5-Chloro-3-[4-(isopropylaminomethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=651 [M+H]$^+$

Example 137

5-Chloro-3-{4-[(2-hydroxyethylamino)methyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=653 [M+H]$^+$

Example 138

5-Chloro-1-(4-methoxybenzenesulfonyl)-3-[2-methoxy-4-(3-oxopiperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=692 [M+H]$^+$

Example 139

5-Chloro-3-[5-(tert-butylaminomethyl)-2-methoxyphenyl]-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=665 [M+H]$^+$

Example 140

5-Chloro-3-{5-[(2-hydroxyethylamino)methyl]-2-methoxyphenyl}-1-(4-methoxybenzenesulfonyl)-3-((S)-1-oxazol-2-yl-ethylamino)-1,3-dihydroindol-2-one; trifluoroacetic acid salt; MS (API-ES, pos) m/z=627 [M+H]$^+$

Example 141

5-Chloro-3-[2-methoxy-5-(4-methylpiperazin-1-ylmethyl)phenyl]-3-((S)-2-oxazol-2-yl-pyrrolidin-1-yl)-1-(4-trifluoromethoxybenzenesulfonyl)-1,3-dihydroindol-2-one; trifluoroacetic acid salt; MS (API-ES, pos) m/z=746 [M+H]$^+$

Example 142

5-Cyano-3-{5-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; MS (API-ES, pos) m/z=713 [M+H]$^+$

Example 143

5-Cyano-1-(4-methoxy-benzenesulfonyl)-3-[2-methoxy-5-(3-oxo-piperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=683 [M+H]$^+$

Example 144

5-Cyano-1-(4-methoxybenzenesulfonyl)-3-[2-methoxy-5-(4-methyl-[1,4]diazepan-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=697 [M+H]$^+$

Example 145

5-Chloro-1-(4-difluoromethoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=728 [M+H]$^+$

Example 146

5-Chloro-1-(4-methoxybenzenesulfonyl)-3-(2-methoxy-4-(morpholin-4-ylmethyl)phenyl)-3-((S)-2-oxazol-2-yl-pyrrolidin-1-yl)-1,3-dihydroindol-2-one; trifluoroacetic acid salt; MS (API-ES, pos) m/z=679 [M+H]$^+$

Example 147

5-Cyano-3-{4-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; MS (API-ES, pos) m/z=713 [M+H]$^+$

Example 148

5-Cyano-3-[4-(4-ethylpiperazin-1-ylmethyl)-2-methoxyphenyl]-1-(4-methoxybenzenesulfonyl)-3-((S)-2-oxazol-2-yl-pyrrolidin-1-yl)-1,3-dihydroindol-2-one; MS (API-ES, pos) m/z=697 [M+H]$^+$

Example 149

5-Cyano-3-((2S,4R)-4-hydroxy-2-oxazol-2-yl-pyrrolidin-1-yl)-1-(4-methoxybenzenesulfonyl)-3-[2-methoxy-5-(4-methylpiperazin-1-ylmethyl)phenyl]-1,3-dihydroindol-2-one-5; trifluoroacetic acid salt; MS (API-ES, pos) m/z=699 [M+H]$^+$

Example 150

5-Cyano-3-(5-dimethylaminomethyl-2-methoxyphenyl)-3-((2S,4R)-4:-hydroxy-2-oxazol-2-yl-pyrrolidin-1-yl)-1-(4-methoxybenzenesulfonyl)-1,3-dihydroindol-2-one; trifluoroacetic acid salt; MS (API-ES, pos) m/z=644 [M+H]$^+$

Example 151

5-Cyano-3-(5-ethylaminomethyl-2-methoxyphenyl)-3-((2S,4R)-4-hydroxy-2-oxazol-2-yl-pyrrolidin-1-yl)-1-(4-methoxybenzenesulfonyl)-1,3-dihydroindol-2-one; trifluoroacetic acid salt; MS (API-ES, pos) m/z=644 [M+H]$^+$

Example 152

5-Chloro-3-[4-(4-ethylpiperazin-1-ylmethyl)-2-methoxyphenyl]-3-((S)-2-oxazol-2-yl-pyrrolidin-1-yl-1-(4-cyanobenzenesulfonyl)-1,3-dihydroindol-2-one; trifluoroacetic acid salt; MS (API-ES, pos) m/z=701 [M+H]$^+$

Example 153

5-Cyano-1-(4-methoxybenzenesulfonyl)-3-(2-methoxy-4-piperazin-1-ylmethylphenyl)-3-((S)-2-oxazol-2-yl-pyrrolidin-1-yl)-1,3-dihydroindol-2-one; trifluoroacetic acid salt; MS (API-ES, pos) m/z=669 [M+H]$^+$

Example 154

5-Cyano-3-{4-[(2-hydroxyethylamino)methyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=644 [M+H]$^+$

Example 155

5-Chloro-1-(4-methoxybenzenesulfonyl)-3-(2-methoxy-5-methylaminomethylphenyl)-3-(2-thiazol-2-yl-pyrrolidin-1-yl)-1,3-dihydroindol-2-one; trifluoroacetic acid salt; MS (API-ES, pos) m/z=639 [M+H]$^+$

Example 156

5-Chloro-3-(4-dimethylaminomethyl-2-methoxyphenyl)-3-((S)-2-oxazol-2-yl-pyrrolidin-1-yl)-1-(4-cyanobenzenesulfonyl)-1,3-dihydroindol-2-one; trifluoroacetic acid salt; MS (API-ES, pos) m/z=632 [M+H]$^+$

Example 157

5-Chloro-3-(2-methoxy-4-pyrrolidin-1-ylmethylphenyl)-3-((S)-2-oxazol-2-ylpyrrolidin-1-yl)-1-(4-cyanobenzenesulfonyl)-1,3-dihydroindol-2-one; trifluoroacetic acid salt; MS (API-ES, pos) m/z=658 [M+H]$^+$

Example 158

5-Chloro-3-[2-methoxy-4-(4-methylpiperazin-1-ylmethyl)phenyl]-3-((S)-2-oxazol-2-yl-pyrrolidin-1-yl)-1-(4-cyanobenzenesulfonyl)-1,3-dihydroindol-2-one; trifluoroacetic acid salt; MS (API-ES, pos) m/z=687 [M+H]$^+$

Example 159

5-Chloro-3-(2-methoxy-4-propylaminomethylphenyl)-3-((S)-2-oxazol-2-yl-pyrrolidin-1-yl)-1-(4-cyanobenzenesulfonyl)-1,3-dihydroindol-2-one; trifluoroacetic acid salt; MS (API-ES, pos) m/z=646 [M+H]$^+$

Example 160

5-Cyano-3-((2S,4R)-4-hydroxy-2-oxazol-2-yl-pyrrolidin-1-yl)-1-(4-methoxybenzenesulfonyl)-3-(2-methoxy-5-piperazin-1-ylmethylphenyl)-1,3-dihydroindol-2-one; trifluoroacetic acid salt; MS (API-ES, pos) m/z=685 [M+H]$^+$

Example 161

5-Chloro-3-(5-allylaminomethyl-2-methoxyphenyl)-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=649 [M+H]$^+$

Example 162

5-Chloro-3-(2-methoxy-4-piperazin-1-ylmethylphenyl)-3-((S)-2-oxazol-2-yl-pyrrolidin-1-yl)-1-(4-cyanobenzenesulfonyl)-1,3-dihydroindol-2-one; trifluoroacetic acid salt; MS (API-ES, pos) m/z=673 [M+H]$^+$

Example 163

5-Cyano-3-((2S,4R)-4-hydroxy-2-oxazol-2-yl-pyrrolidin-1-yl)-1-(4-methoxybenzenesulfonyl)-3-(2-methoxy-5-methylaminomethylphenyl)-1,3-dihydroindol-2-one; trifluoroacetic acid salt; MS (API-ES, pos) m/z=630 [M+H]$^+$

Example 164

5-Chloro-1-(4-methoxybenzenesulfonyl)-3-[2-methoxy-5-(4-methylpiperazin-1-ylmethyl)pyridin-3-yl]-3-((S)-2-oxazol-2-yl-pyrrolidin-1-yl)-1,3-dihydroindol-2-one; MS (API-ES, pos) m/z=693 [M+H]$^+$

Example 165

5-Chloro-3-((2S,4R)-4-hydroxy-2-oxazol-2-yl-pyrrolidin-1-yl)-1-(4-methoxybenzenesulfonyl)-3-[2-methoxy-4-(4-methylpiperazin-1-ylmethyl)phenyl]-1,3-dihydroindol-2-one; MS (API-ES, pos) m/z=708 [M+H]$^+$

Example 166

5-Chloro-3-((2S,4R)-4-hydroxy-2-oxazol-2-yl-pyrrolidin-1-yl)-3-[4-(4-isopropylpiperazin-1-ylmethyl)-2-methoxyphenyl]-1-(4-methoxybenzenesulfonyl)-1,3-dihydroindol-2-one; MS (API-ES, pos) m/z=736 [M+H]$^+$

Example 167

5-Chloro-1-(4-methoxybenzenesulfonyl)-3-(2-methoxy-5-methylaminomethylpyridin-3-yl)-3-((S)-2-oxazol-2-yl-pyrrolidin-1-yl)-1,3-dihydroindol-2-one; MS (API-ES, pos) m/z=624 [M+H]$^+$

Example 168

5-Chloro-3-(5-cyclopropylaminomethyl-2-methoxyphenyl)-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=649 [M+H]$^+$

Example 169

5-Chloro-3-((2S,4R)-4-hydroxy-2-oxazol-2-yl-pyrrolidin-1-yl)-1-(4-methoxybenzenesulfonyl)-3-(2-methoxy-4-piperidin-1-ylmethylphenyl)-1,3-dihydroindol-2-one; MS (API-ES, pos) m/z=693 [M+H]$^+$

Example 170

5-Chloro-3-{4-[(ethylmethylamino)methyl]-2-methoxyphenyl}-3-((2S,4R)-4-hydroxy-2-oxazol-2-yl-pyrrolidin-1-yl)-1-(4-methoxybenzenesulfonyl)-1,3-dihydroindol-2-one; MS (API-ES, pos) m/z=667 [M+H]$^+$

Example 171

5-Chloro-3-[2-methoxy-5-(4-methylpiperazin-1-ylmethyl)phenyl]-3-((S)-2-oxazol-2-yl-pyrrolidin-1-yl)-1-(thiophene-2-sulfonyl)-1,3-dihydroindol-2-one; MS (API-ES, pos) m/z=668 [M+H]$^+$

Example 172

5-Cyano-3-(4-dimethylaminomethyl-2-methoxyphenyl)-3-((2S,4R)-4-hydroxy-2-oxazol-2-yl-pyrrolidin-1-yl)-1-(4-methoxybenzenesulfonyl)-1,3-dihydroindol-2-one; MS (API-ES, pos) m/z=644 [M+H]$^+$

Example 173

5-Chloro-3-[2-fluoro-5-(4-methylpiperazin-1-ylmethyl)phenyl]-1-(4-methoxybenzenesulfonyl)-3-((S)-2-oxazol-2-yl-pyrrolidin-1-yl)-1,3-dihydroindol-2-one; MS (API-ES, pos) m/z=680 [M+H]$^+$

Example 174

5-Chloro-3-(5-dimethylaminomethyl-2-fluorophenyl)-1-(4-methoxybenzenesulfonyl)-3-((S)-2-oxazol-2-yl-pyrrolidin-1-yl)-1,3-dihydroindol-2-one; MS (API-ES, pos) m/z=625 [M+H]$^+$

Example 175

5-Chloro-3-[2-fluoro-5-(isopropylaminomethyl)phenyl]-1-(4-methoxybenzenesulfonyl)-3-((S)-2-oxazol-2-yl-pyrrolidin-1-yl)-1.3-dihydroindol-2-one; MS (API-ES, pos) m/z=639 [M+H]$^+$

Example 176

5-Chloro-3-(5-ethylaminomethyl-2-fluorophenyl)-1-(4-methoxybenzenesulfonyl)-3-((S)-2-oxazol-2-yl-pyrrolidin-1-yl)-1,3-dihydroindol-2-one; acetic acid salt; MS (API-ES, pos) m/z=625 [M+H]$^+$

Example 177

5-Cyano-3-((2S,4R)-4-hydroxy-2-oxazol-2-yl-pyrrolidin-1-yl)-1-(4-methoxybenzenesulfonyl)-3-(2-methoxy-5-propylaminomethylphenyl)-1,3-dihydroindol-2-one; trifluoroacetic acid salt; MS (API-ES, pos) m/z=658 [M+H]$^+$

Example 178

5-Cyano-3-((2S,4R)-4-hydroxy-2-oxazol-2-yl-pyrrolidin-1-yl)-1-(4-methoxybenzenesulfonyl)-3-[2-methoxy-4-(4-methylpiperazin-1-ylmethyl)phenyl]-1,3-dihydroindol-2-one; MS (API-ES, pos) m/z=699 [M+H]$^+$

Example 179

5-Cyano-3-[4-(4-ethylpiperazin-1-ylmethyl)-2-methoxyphenyl]-3-((2S,4R)-4-hydroxy-2-oxazol-2-yl-pyrrolidin-1-yl)-1-(4-methoxybenzenesulfonyl)-1,3-dihydroindol-2-one; MS (API-ES, pos) m/z=713 [M+H]$^+$

Example 180

5-Chloro-3-((2S,4R)-4-hydroxy-2-oxazol-2-yl-pyrrolidin-1-yl)-3-[2-methoxy-4-(4-methylpiperazin-1-ylmethyl)phenyl]-1-(4-cyanobenzenesulfonyl)-1,3-dihydroindol-2-one; MS (API-ES, pos) m/z=703 [M+H]$^+$

Example 181

5-Chloro-3-[4-(4-ethylpiperazin-1-ylmethyl)-2-methoxyphenyl]-3-((2S,4R)-4-hydroxy-2-oxazol-2-yl-pyrrolidin-1-yl)-1-(4-cyanobenzenesulfonyl)-1,3-dihydroindol-2-one; MS (API-ES, pos) m/z=717 [M+H]$^+$

Example 182

5-Chloro-3-(4-dimethylaminomethyl-2-methoxyphenyl)-3-((2S,4R)-4-hydroxy-2-oxazol-2-yl-pyrrolidin-1-yl)-1-(4-cyanobenzenesulfonyl)-1,3-dihydroindol-2-one; MS (API-ES, pos) m/z=648 [M+H]$^+$

Example 183

5-Chloro-3-((2S,4R)-4-hydroxy-2-oxazol-2-yl-pyrrolidin-1-yl)-3-(2-methoxy-4-(pyrrolidin-1-ylmethyl)phenyl)-1-(4-cyanobenzenesulfonyl)-1,3-dihydroindol-2-one; MS (API-ES, pos) m/z=674 [M+H]$^+$

Example 184

5-Chloro-1-(4-methoxybenzenesulfonyl)-3-[6-(4-methylpiperazin-1-ylmethyl)benzo[1,3]dioxol-4-yl]-3-((S)-2-oxazol-2-yl-pyrrolidin-1-yl)-1,3-dihydroindol-2-one; MS (API-ES, pos) m/z=706 [M+H]$^+$

Example 185

5-Chloro-1-(4-methoxybenzenesulfonyl)-3-(6-methylaminomethylbenzo[1,3]dioxol-4-yl)-3-((S)-2-oxazol-2-yl-pyrrolidin-1-yl)-1,3-dihydroindol-2-one; MS (API-ES, pos) m/z=637 [M+H]$^+$

Example 186

5-Chloro-3-(6-dimethylaminomethylbenzo[1,3]dioxol-4-yl)-1-(4-methoxybenzenesulfonyl)-3-((S)-2-oxazol-2-yl-pyrrolidin-1-yl)-1,3-dihydroindol-2-one; acetic acid salt; MS (API-ES, pos) m/z=651 [M+H]$^+$

Example 187

5-Chloro-3-[6-(isopropylaminomethyl)benzo[1,3]dioxol-4-yl]-1-(4-methoxybenzenesulfonyl)-3-((S)-2-oxazol-2-yl-pyrrolidin-1-yl)-1,3-dihydroindol-2-one; acetic acid salt; MS (API-ES, pos) m/z=665 [M+H]$^+$

Example 188

5-Chloro-3-(6-ethylaminomethylbenzo[1,3]dioxol-4-yl)-1-(4-methoxybenzenesulfonyl)-3-((S)-2-oxazol-2-yl-pyrrolidin-1-yl)-1,3-dihydroindol-2-one; acetic acid salt; MS (API-ES, pos) m/z=651 [M+H]$^+$

Example 189

5-Chloro-3-(4-ethylaminomethyl-2-methoxyphenyl)-3-((2S,4R)-4-hydroxy-2-oxazol-2-yl-pyrrolidin-1-yl)-1-(4-cyanobenzenesulfonyl)-1,3-dihydroindol-2 one; MS (API-ES, pos) m/z=648 [M+H]$^+$

Example 190

5-Chloro-3-((2S,4R)-4-hydroxy-2-oxazol-2-yl-pyrrolidin-1-yl)-3-(2-methoxy-4-methylaminomethylphenyl)-1-(4-cyanobenzenesulfonyl)-1,3-dihydroindol-2 one; MS (API-ES, pos) m/z=634 [M+H]$^+$

Example 191

5-Cyano-3-[5-(4-hydroxypiperidin-1-ylmethyl)-2-methoxyphenyl]-1-(4-methoxybenzenesulfonyl)-3-((S)-2-oxazol-2-yl-pyrrolidin-1-yl)-1,3-dihydroindol-2-one; MS (API-ES, pos) m/z=684 [M+H]$^+$

Example 192

5-Chloro-1-(4-methoxybenzenesulfonyl)-3-[2-methoxy-3-(4-methylpiperazin-1-ylmethyl)phenyl]-3-((S)-2-oxazol-2-yl-pyrrolidin-1-yl)-1,3-dihydroindol-2-one; MS (API-ES, pos) m/z=692 [M+H]$^+$

Example 193

5-Chloro-3-[4-(4-ethylpiperazin-1-ylmethyl)-2-methoxyphenyl]-6-fluoro-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=724 [M+H]$^+$

Example 194

5-Chloro-3-(3-dimethylaminomethyl-2-methoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=637 [M+H]$^+$

Example 195

5-Chloro-1-(4-methoxybenzenesulfonyl)-3-(2-methoxy-3-pyrrolidin-1-ylmethylphenyl)-3-((S)-2-oxazol-2-yl-pyrrolidin-1-yl)-1,3-dihydroindol-2-one; MS (API-ES, pos) m/z=663 [M+H]$^+$

Example 196

5-Chloro-1-(4-cyanobenzenesulfonyl)-3-{4-[(2-hydroxyethylamino)methyl]-2-methoxyphenyl}-3-((2S,4R)-4-hydroxy-2-oxazol-2-yl-pyrrolidin-1-yl)-2,3-dihydroindol-2-one; MS (API-ES, pos) m/z=644 [M+H]$^+$

Example 197

5-Chloro-1-(4-cyanobenzenesulfonyl)-3-{4-[4-(2-hydroxyethyl)piperazin-1-ylmethyl]-2-methoxyphenyl}-3-((S)-2-oxazol-2-yl-pyrrolidin-1-yl)-2,3-dihydroindol-2-one; MS (API-ES, pos) m/z=717 [M+H]$^+$

Example 198

5-Chloro-6-fluoro-1-(4-methoxybenzenesulfonyl)-3-[2-methoxy-5-(4-methylpiperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=710 [M+H]$^+$

Example 199

5-Chloro-3-[4-(4-ethylpiperazin-1-ylmethyl)-2-methoxyphenyl]-4-fluoro-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=724 [M+H]$^+$

Example 200

5-Chloro-6-fluoro-1-(4-methoxybenzenesulfonyl)-3-(2-methoxy-5-piperazin-1-ylmethylphenyl)-3-((S)-2-oxazol-2-yl-pyrrolidin-1-yl)-1,3-dihydroindol-2-one; trifluoroacetic acid salt; MS (API-ES, pos) m/z=696 [M+H]$^+$

Example 201

5-Chloro-6-fluoro-1-(4-methoxybenzenesulfonyl)-3-[2-methoxy-4-(4-methylpiperazin-1-ylmethyl)phenyl]-3-((S)-2-oxazol-2-yl-pyrrolidin-1-yl)-1,3-dihydroindol-2-one; trifluoroacetic acid salt; MS (API-ES, pos) m/z=710 [M+H]$^+$

Example 202

5-Chloro-3-[2-ethoxy-5-(4-methylpiperazin-1-ylmethyl)phenyl]-1-(4-methoxybenzenesulfonyl)-3-((S)-2-oxazol-2-yl-pyrrolidin-1-yl)-1,3-dihydroindol-2-one; MS (API-ES, pos) m/z=706 [M+H]$^+$

Example 203

5-Chloro-3-(2-ethoxy-5-methylaminomethylphenyl)-1-(4-methoxybenzenesulfonyl)-3-((S)-2-oxazol-2-yl-pyrrolidin-1-yl)-1,3-dihydroindol-2-one; MS (API-ES, pos) m/z=637 [M+H]$^+$

Example 204

5-Chloro-3-(5-dimethylaminomethyl-2-ethoxyphenyl)-1-(4-methoxybenzenesulfonyl)-3-((S)-2-oxazol-2-yl-pyrrolidin-1-yl)-1,3-dihydroindol-2-one; MS (API-ES, pos) m/z=651 [M+H]$^+$

Example 205

5-Chloro-3-[2-ethoxy-5-(isopropylaminomethyl)phenyl]-1-(4-methoxybenzenesulfonyl)-3-((S)-2-oxazol-2-yl-pyrrolidin-1-yl)-1,3-dihydroindol-2-one; MS (API-ES, pos) m/z=665 [M+H]$^+$

Example 206

5-Chloro-3-(2-ethoxy-5-ethylaminomethylphenyl)-1-(4-methoxybenzenesulfonyl)-3-((S)-2-oxazol-2-yl-pyrrolidin-1-yl)-1,3-dihydroindol-2-one; MS (API-ES, pos) m/z=651 [M+H]$^+$

Example 207

5-Chloro-1-(4-methoxybenzenesulfonyl)-3-[2-methoxy-5-(4-methylpiperazin-1-ylmethyl)phenyl]-3-((S)-2-[1,2,4]oxadiazol-3-yl-pyrrolidin-1-yl)-1,3-dihydroindol-2-one; trifluoroacetic acid salt; MS (API-ES, pos) m/z=693 [M+H]$^+$

Example 208

5-Chloro-1-(4-methoxybenzenesulfonyl)-3-(2-methoxy-5-piperazin-1-ylmethylphenyl)-3-((S)-2-[1,2,4]oxadiazol-3-yl-pyrrolidin-1-yl)-1,3-dihydroindol-2-one; trifluoroacetic acid salt; MS (API-ES, pos) m/z=679 [M+H]$^+$

Example 209

5-Chloro-3-(5-dimethylaminomethyl-2-methoxyphenyl)-1-(4-methoxybenzenesulfonyl)-3-((S)-2-[1,2,4]oxadiazol-3-yl-pyrrolidin-1-yl)-1,3-dihydroindol-2-one; trifluoroacetic acid salt; MS (API-ES, pos) m/z=638 [M+H]$^+$

Example 210

5-Chloro-1-(4-methoxybenzenesulfonyl)-3-(2-methoxy-5-pyrrolidin-1-ylmethylphenyl)-3-((S)-2-[1,2,4]oxadiazol-3-yl-pyrrolidin-1-yl)-1,3-dihydroindol-2-one; trifluoroacetic acid salt; MS (API-ES, pos) m/z=664 [M+H]$^+$

Example 211

5-Chloro-6-fluoro-1-(4-methoxybenzenesulfonyl)-3-(2-methoxy-4-piperazin-1-ylmethylphenyl)-3-((S)-2-oxazol-2-yl-pyrrolidin-1-yl)-1,3-dihydroindol-2-one; trifluoroacetic acid salt; MS (API-ES, pos) m/z=696 [M+H]$^+$

Example 212

5-Chloro-6-fluoro-3-{4-[4-(2-hydroxyethyl)piperazin-1-ylmethyl]-2-methoxyphenyl}-1-(4-methoxybenzenesulfonyl)-3-((S)-2-oxazol-2-yl-pyrrolidin-1-yl)-1,3-dihydroindol-2-one; trifluoroacetic acid salt; MS (API-ES, pos) m/z=740 [M+H]$^+$

Example 213

3-((2S,4R)-4-tert-butoxy-2-oxazol-2-yl-pyrrolidin-1-yl)-5-chloro-1-(4-methoxybenzenesulfonyl)-3-(2-methoxy-5-pyrrolidin-1-ylmethylphenyl)-1,3-dihydroindol-2-one; MS (API-ES, pos) m/z=735 [M+H]$^+$

Example 214

3-((2S,4R)-4-tert-butoxy-2-oxazol-2-yl-pyrrolidin-1-yl)-5-chloro-1-(4-methoxybenzenesulfonyl)-3-[2-methoxy-5-(4-methyl piperazin-1-ylmethyl)phenyl]-1,3-dihydroindol-2-one; MS (API-ES, pos) m/z=764 [M+H]⁺

Example 215

5-Chloro-3-((2S,4R)-4-tert-butoxy-2-oxazol-2-yl-pyrrolidin-1-yl)-3-{5-[4-(2-hydroxyethyl)piperazin-1-ylmethyl]-2-methoxyphenyl}-1-(4-methoxybenzenesulfonyl)-1,3-dihydroindol-2-one; MS (API-ES, pos) m/z=794 [M+H]⁺

Example 216

5-Chloro-3-(5-ethylaminomethyl-2-methoxyphenyl)-1-(4-methoxybenzenesulfonyl)-3-((S)-2-[1,2,4]oxadiazol-3-yl-pyrrolidin-1-yl)-1,3-dihydroindol-2-one; trifluoroacetic acid salt; MS (API-ES, pos) m/z=638 [M+H]⁺

Example 217

5-Chloro-3-((2S,4R)-4-hydroxy-2-oxazol-2-yl-pyrrolidin-1-yl)-1-(4-methoxybenzenesulfonyl)-3-(2-methoxy-4-methylaminomethylphenyl)-1,3-dihydroindol-2-one; trifluoroacetic acid salt; MS (API-ES, pos) m/z=639 [M+H]⁺

Example 218

3-((2S,4R)-4-tert-butoxy-2-oxazol-2-yl-pyrrolidin-1-yl)-5-chloro-3-(5-dimethylaminomethyl-2-methoxyphenyl)-1-(4-methoxybenzenesulfonyl)-1,3-dihydroindol-2-one; MS (API-ES, pos) m/z=709 [M+H]⁺

Example 219

3-((2S,4R)-4-tert-butoxy-2-oxazol-2-yl-pyrrolidin-1-yl)-5-chloro-3-(5-ethylaminomethyl-2-methoxyphenyl)-1-(4-methoxybenzenesulfonyl)-1,3-dihydroindol-2-one; MS (API-ES, pos) m/z=709 [M+H]⁺

Example 220

5-Cyano-3-((2S,4R)-4-hydroxy-2-oxazol-2-yl-pyrrolidin-1-yl)-1-(4-methoxybenzenesulfonyl)-3-(2-methoxy-5-morpholin-4-ylmethylphenyl)-1,3-dihydroindol-2-one; trifluoroacetic acid salt; MS (API-ES, pos) m/z=686 [M+H]⁺

Example 221

5-Cyano-3-[5-(4-ethylpiperazin-1-ylmethyl)-2-methoxyphenyl]-3-((2S,4R)-4-hydroxy-2-oxazol-2-yl-pyrrolidin-1-yl)-1-(4-methoxybenzenesulfonyl)-2,3-dihydro-1H-indol-2-one; trifluoroacetic acid salt; MS (API-ES, pos) m/z=713 [M+H]⁺

Example 222

5-Cyano-3-{5-[4-(2-hydroxyethyl)piperazin-1-ylmethyl]-2-methoxyphenyl}-3-((2S,4R)-4-hydroxy-2-oxazol-2-yl-pyrrolidin-1-yl)-1-(4-methoxybenzenesulfonyl)-2,3-dihydro-1H-indol-2-one; trifluoroacetic acid salt; MS (API-ES, pos) m/z=729 [M+H]⁺

Example 223

5-Chloro-3-(5-dimethylaminomethyl-2-methoxyphenyl)-1-(4-methoxybenzenesulfonyl)-3-((2S,4R)-4-methoxy-2-oxazol-2-yl-pyrrolidin-1-yl)-1,3-dihydroindol-2-one; trifluoroacetic acid salt; MS (API-ES, pos) m/z=667 [M+H]⁺

Example 224

5-Chloro-1-(4-methoxybenzenesulfonyl)-3-[2-methoxy-5-(4-methylpiperazin-1-ylmethyl)phenyl]-3-((2S,4R)-4-methoxy-2-oxazol-2-yl-pyrrolidin-1-yl)-1,3-dihydroindol-2-one; trifluoroacetic acid salt; MS API-ES, pos) m/z=722 [M+H]⁺

Example 225

5-Chloro-1-(4-methoxybenzenesulfonyl)-3-[2-methoxy-5-(4-methylpiperazin-1-ylmethyl)phenyl]-3-((S)-2-methyl-2-oxazol-2-yl-pyrrolidin-1-yl)-1,3-dihydroindol-2-one; trifluoroacetic acid salt; MS (API-ES, pos) m/z=706 [M+H]⁺

Example 226

5-Chloro-3-{5-[4-(2-hydroxyethyl)piperazin-1-ylmethyl]-2-methoxyphenyl}-1-(4-methoxybenzenesulfonyl)-3-((S)-2-methyl-2-oxazol-2-yl-pyrrolidin-1-yl)-1,3-dihydroindol-2-one; trifluoroacetic acid salt; MS (API-ES, pos) m/z=736 [M+H]⁺

Example 227

5-Chloro-1-(4-methoxybenzenesulfonyl)-3-(2-methoxy-5-methylaminomethylphenyl)-3-((S)-2-methyl-2-oxazol-2-yl-pyrrolidin-1-yl)-1,3-dihydroindol-2-one; trifluoroacetic acid salt; MS (API-ES, pos) m/z=637 [M+H]⁺

Example 228

5-Cyano-3-((2S,4R)-4-fluoro-2-oxazol-2-yl-pyrrolidin-1-yl)-1-(4-methoxybenzenesulfonyl)-3-[2-methoxy-5-(4-methylpiperazin-1-ylmethyl)phenyl]-1,3-dihydroindol-2-one; trifluoroacetic acid salt; MS (API-ES, pos) m/z=701 [M+H]⁺

Example 229

5-Cyano-3-((2S,4R)-4-fluoro-2-oxazol-2-yl-pyrrolidin-1-yl)-3-{5-[4-(2-hydroxyethyl)piperazin-1-ylmethyl]-2-methoxyphenyl}-1-(4-methoxybenzenesulfonyl)-1,3-dihydroindol-2-one; trifluoroacetic acid salt; MS (API-ES, pos) m/z=731 [M+H]⁺

Example 230

5-Cyano-3-(5-dimethylaminomethyl-2-methoxyphenyl)-3-((2S,4R)-4-fluoro-2-oxazol-2-yl-pyrrolidin-1-yl)-1-(4-methoxybenzenesulfonyl)-1,3-dihydroindol-2-one; trifluoroacetic acid salt; MS (API-ES, pos) m/z=646 [M+H]⁺

Example 231

5-Chloro-3-(5-ethylaminomethyl-2-methoxyphenyl)-1-(4-methoxybenzenesulfonyl)-3-((S)-2-methyl-2-oxazol-2-yl-pyrrolidin-1-yl)-1,3-dihydroindol-2-one; trifluoroacetic acid salt; MS (API-ES, pos) m/z=651 [M+H]$^+$

Example 232

5-Chloro-3-[5-(4-ethylpiperazin-1-ylmethyl)-2-methoxyphenyl]-1-(4-methoxybenzenesulfonyl)-3-((S)-2-methyl-2-oxazol-2-yl-pyrrolidin-1-yl)-1,3-dihydroindol-2-one; trifluoroacetic acid salt; MS (API-ES, pos) m/z=720 [M+H]$^+$

Example 233

5-Chloro-3-{5-[4-(2-hydroxyethyl)piperazin-1-ylmethyl]-2-methoxyphenyl}-1-(4-methoxybenzenesulfonyl)-3-[(S)-2-(5-methyloxazol-2-yl)-pyrrolidin-1-yl]-1,3-dihydroindol-2-one; trifluoroacetic acid salt; MS (API-ES, pos) m/z=736 [M+H]$^+$

Example 234

5-Chloro-3-(5-dimethylaminomethyl-2-methoxyphenyl)-1-(4-methoxybenzenesulfonyl)-3-[(S)-2-(5-methyloxazol-2-yl)-pyrrolidin-1-yl]-1,3-dihydroindol-2-one; trifluoroacetic acid salt; MS (API-ES, pos) m/z=651 [M+H]$^+$

Example 235

5-Chloro-1-(4-methoxybenzenesulfonyl)-3-[2-methoxy-5-(4-methylpiperazin-1-ylmethyl)phenyl]-3-[(S)-2-(5-methyloxazol-2-yl)-pyrrolidin-1-yl]-1,3-dihydroindol-2-one; trifluoroacetic acid salt; MS (API-ES, pos) m/z=706 [M+H]$^+$ The compounds according to the invention represent antagonists of the so-called receptors of the vasopressin/oxytocin family. Such compounds may be investigated in suitable tests for determining the affinity for a receptor, where the affinity constant Ki is a measure of the potency of the compounds, and a smaller value represents a higher potency. The compounds according to the invention were investigated for their affinity for the V1b receptor in the receptor binding test described below.

Vasopressin V1b Receptor Binding Test:
Substances:

The test substances were dissolved at a concentration of 10$^{-2}$ M in DMSO, and were further diluted to 5×10$^{-4}$ M to 5×10$^{-9}$ M in DMSO. This DMSO predilution series was diluted 1:10 with test buffer. In the test assay the substance concentration was further diluted to 1:5 (2% DMSO in the assay).

Membrane Preparation:

CHO-K1 cells containing stably expressed human vasopressin V1b receptor (3H2 clone) were harvested, and in 50 mM tris-HCl and in the presence of protease inhibitors (Roche complete Mini #1836170) were homogenized for 2×10 seconds using a Polytron homogenizer at the center position, and were then centrifuged for 1 h at 40,000×g. The membrane pellet was homogenized again as described and centrifuged, and was then taken up in 50 mM tris-HCl at pH 7.4, homogenized, and frozen in aliquots at −190° C. and stored in liquid nitrogen.

Binding Test:

The binding test was conducted according to the method of Tahara et al. (Tahara, A. et al., Brit. J. Pharmacol. 125, 1463-1470 (1998)). The incubation buffer was 50 mM tris, 10 mM MgCl$_2$, and 0.1% BSA at pH 7.4. Membranes (50 μg/mL protein in incubation buffer) of CHO-K1 cells containing stably expressed human V1b receptors (cell line hV1b_3H2_CHO) together with 1.5 nM $^3$H-AVP (8-Arg-vasopressin, PerkinElmer #18479) in incubation buffer (50 mM tris, 10 mM MgCl$_2$, 0.1% BSA, pH 7.4) were incubated in the test assay (250 μL) (total binding), or were additionally incubated with increasing concentrations of test substance (displacement test). The nonspecific binding was determined using 1 μM AVP (Bachem #H1780). All determinations were performed in triplicate. After incubation (60 minutes at room temperature), the free radioligand was filtered off by vacuum filtration (Skatron 7000 cell harvester) through Wathman GF/B fiberglass filter mats, and the filters were transferred to scintillation vessels. The liquid scintillation measurement was conducted in a Model 2000 or 2200CA TriCarb unit (Packard). The measured cpm was converted to dpm using a standard quench series.

Analysis:

The binding parameters were calculated by nonlinear regression in SAS. The program algorithms function analogously to the LIGAND analytical program (Munson, P. J. and Rodbard, D., Analytical Biochem. 107, 220-239 (1980)). The Kd value for $^3$H-AVP for the recombinant hV2 receptors was 0.4 nM, which was used for determining the Ki value.

The affinities of the compounds according to the invention for human vasopressin receptor V1b were measured according to the above test, and the affinity constants (Ki) were determined. Table 1 below lists the V1b receptor affinity for selected compounds (+++means<10 nM, ++means 10-100 nM, and +means 100-1000 nM).

For compounds according to the invention having more than one stereogenic center, the stated affinities for the V1b receptor refer to the diastereomer which has a greater affinity (lower Ki value) for the V1b receptor.

TABLE 1

| Example | V1b Ki |
| --- | --- |
| 1 | +++ |
| 2 | ++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | ++ |
| 16 | +++ |
| 17 | +++ |
| 18 | +++ |
| 19 | +++ |
| 20 | +++ |
| 21 | +++ |
| 22 | ++ |
| 23 | +++ |
| 24 | +++ |

TABLE 1-continued

| Example | V1b Ki |
|---|---|
| 25 | +++ |
| 26 | +++ |
| 28 | + |
| 30 | + |
| 31 | + |
| 32 | + |
| 33 | + |
| 34 | + |
| 35 | + |
| 37 | + |
| 38 | + |
| 39 | + |
| 40 | + |
| 41 | ++ |
| 42 | ++ |
| 43 | + |
| 45 | +++ |
| 46 | ++ |
| 47 | +++ |
| 48 | ++ |
| 49 | ++ |
| 50 | +++ |
| 52 | ++ |
| 53 | ++ |
| 54 | ++ |
| 55 | ++ |
| 56 | +++ |
| 57 | +++ |
| 58 | ++ |
| 60 | ++ |
| 61 | ++ |
| 63 | ++, |
| 64 | ++ |
| 65 | ++ |
| 68 | ++ |
| 70 | ++ |
| 74 | ++ |
| 75 | ++ |
| 78 | ++ |
| 80 | ++ |
| 81 | ++ |
| 82 | + |
| 84 | + |
| 85 | ++ |
| 86 | ++ |
| 87 | ++ |
| 88 | +++ |
| 89 | +++ |
| 90 | ++ |
| 91 | +++ |
| 92 | +++ |
| 93 | + |
| 94 | ++ |
| 95 | ++ |
| 96 | ++ |
| 97 | ++ |
| 98 | ++ |
| 99 | ++ |
| 100 | ++ |
| 101 | ++ |
| 102 | +++ |
| 103 | +++ |
| 104 | ++ |
| 105 | +++ |
| 106 | ++ |
| 107 | ++ |
| 108 | ++ |
| 109 | ++ |
| 110 | ++ |
| 111 | ++ |
| 112 | |
| 113 | +++ |
| 114 | +++ |
| 115 | +++ |
| 116 | +++ |
| 117 | ++ |
| 118 | ++ |
| 119 | ++ |
| 120 | + |
| 121 | ++ |
| 122 | + |
| 123 | + |
| 124 | ++ |
| 125 | ++ |
| 126 | + |
| 127 | +++ |
| 128 | +++ |
| 129 | ++ |
| 130 | ++ |
| 131 | ++ |
| 132 | ++ |
| 133 | ++ |
| 134 | ++ |
| 135 | +++ |
| 136 | ++ |
| 137 | ++ |
| 138 | ++ |
| 139 | ++ |
| 140 | +++ |
| 141 | + |
| 142 | +++ |
| 143 | +++ |
| 144 | +++ |
| 145 | ++ |
| 146 | ++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | ++ |
| 157 | ++ |
| 158 | +++ |
| 159 | ++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | ++ |
| 172 | ++ |
| 173 | ++ |
| 174 | ++ |
| 175 | ++ |
| 176 | ++ |
| 177 | +++ |
| 178 | +++ |
| 179 | +++ |
| 180 | +++ |
| 181 | +++ |
| 182 | ++ |
| 183 | ++ |
| 184 | +++ |
| 185 | ++ |
| 186 | ++ |
| 187 | +++ |
| 188 | +++ |
| 189 | ++ |
| 190 | ++ |
| 191 | +++ |
| 192 | +++ |
| 193 | +++ |
| 194 | ++ |
| 195 | + |
| 196 | ++ |
| 197 | ++ |

TABLE 1-continued

| Example | V1b Ki |
|---|---|
| 198 | +++ |
| 199 | +++ |
| 200 | +++ |
| 201 | +++ |
| 202 | ++ |
| 203 | ++ |
| 204 | ++ |
| 205 | ++ |
| 206 | ++ |
| 207 | +++ |
| 208 | ++ |
| 209 | +++ |
| 210 | +++ |
| 211 | +++ |
| 212 | +++ |
| 213 | ++ |
| 214 | +++ |
| 215 | ++ |
| 216 | +++ |
| 217 | +++ |
| 218 | ++ |
| 219 | +++ |
| 220 | ++ |
| 221 | +++ |
| 222 | ++ |
| 223 | +++ |
| 224 | +++ |
| 225 | ++ |
| 226 | +++ |
| 227 | +++ |
| 228 | ++ |
| 229 | ++ |
| 230 | ++ |
| 231 | +++ |
| 232 | +++ |
| 233 | ++ |
| 234 | ++ |
| 235 | ++ |

Furthermore, the following tests may be used to determine the affinities for additional vasopressin receptors or their subtypes, for example V1a and V2, and the oxytocin (OT) receptor. The resulting quotients of the Ki values, i.e., "Ki(V1a)/Ki(V1b)," "Ki(V2)/Ki(V1b)," and/or "Ki(OT)Ki(V1b)," may be used as a measure of possible selectivity of the compounds according to the invention with respect to a specific vasopressin or oxytocin receptor.

Vasopressin V1a Receptor Binding Test:
Substances:

The test substances were dissolved at a concentration of $10^{-2}$ M in DMSO. These DMSO solutions were further diluted with incubation buffer (50 mM tris, 10 mM $MgCl_2$, 0.1% BSA at pH 7.4).

Membrane Preparation:

CHO-K1 cells containing stably expressed human vasopressin V1a receptor (5 clone) were harvested, and in 50 mM tris-HCl and in the presence of protease inhibitors (Roche complete Mini #1836170) were homogenized for 2×10 seconds using a Polytron homogenizer at the center position, and were then centrifuged for 1 h at 40,000×g. The membrane pellet was homogenized again as described and centrifuged, and was then taken up in 50 mM tris-HCl at pH 7.4, homogenized, and frozen in aliquots at −190° C. and stored in liquid nitrogen.

Binding Test:

The binding test was conducted according to the method of Tahara et al. (Tahara, A. et al., Brit. J. Pharmacol. 125, 1463-1410 (1998)). The incubation buffer was 50 mM tris, 10 mM $MgCl_2$, and 0.1% BSA at pH 7.4. Membranes (20:g/mL protein in incubation buffer) of CHO-K1 cells containing stably expressed human V1a receptors (cell line hV1a_5_CHO) together with 0.04 nM $^{125}$1-AVP (8-Arg-vasopressin, NEX 128) in incubation buffer (50 mM tris, 10 mM $MgCl_2$, 0.1% BSA at pH 7.4) were incubated in the test assay (250:L) (total binding), or were additionally incubated with increasing concentrations of test substance (displacement test). The nonspecific binding was determined using 1:M AVP (Bachem #H1780). Triplicate determinations were performed.

After incubation (60 minutes at room temperature), the free radioligand was filtered off by vacuum filtration (Skatron 7000 cell harvester) through Wathman GF/B fiberglass filter mats, and the filters were transferred to scintillation vessels.

The liquid scintillation measurement was conducted in a Model 2000 or 2200CA TriCarb unit (Packard). The measured cpm was converted to dpm using a standard quench series.

Analysis:

The binding parameters were calculated by nonlinear regression in SAS. The program algorithms function analogously to the LIGAND analytical program (Munson, P. J. and Rodbard, D., Analytical Biochem. 107, 220-239 (1980)).

The Kd value for $^{125}$1-AVP for the recombinant hV1a receptors was determined in saturation tests. A Kd value of 1.33 nM was used for determining the Ki value.

Vasopressin V2 Receptor Binding Test:
Substances:

The test substances were dissolved at a concentration of $10^{-2}$ M in DMSO. This DMSO solution was further diluted with incubation buffer (50 mM tris, 10 mM $MgCl_2$, 0.1% BSA at pH 7.4).

Membrane Preparation:

CHO-K1 cells containing stably expressed human vasopressin V2 receptor (23 clone) were harvested, and in 50 mM tris-HCl and in the presence of protease inhibitors (Roche complete Mini #1836170) were homogenized for 2×10 seconds using a Polytron homogenizer at the center position, and were then centrifuged for 1 h at 40,000×g. The membrane pellet was homogenized again as described and centrifuged, and was then taken up in 50 mM tris-HCl at pH 7.4, homogenized, and frozen in aliquots at −190° C. and stored in liquid nitrogen.

Binding Test:

The binding test was conducted according to the method of Tahara et al. (Tahara, A. et al., Brit. J. Pharmacol. 125, 1463-1470 (1998)). The incubation buffer was 50 mM tris, 10 mM $MgCl_2$, and 0.1% BSA at pH 7.4. Membranes (50:g/mL protein in incubation buffer) of CHO-K1 cells containing stably expressed human V2 receptors (cell line hV2_23_CHO) together with 1-2 nM $^3$H-AVP (8-Arg-vasopressin, PerkinElmer #18479) in incubation buffer (50 mM tris, 10 mM $MgCl_2$, 0.1% BSA at pH 7.4) were incubated in the test assay (250:L) (total binding), or were additionally incubated with increasing concentrations of test substance (displacement test). The nonspecific binding was determined using 1:M AVP (Bachem #H1780). Triplicate determinations were performed.

After incubation (60 minutes at room temperature), the free radioligand was filtered off by vacuum filtration (Skatron 7000 cell harvester) through Wathman GF/B fiberglass filter mats, and the filters were transferred to scintillation vessels.

The liquid scintillation measurement was conducted in a Model 2000 or 2200CA TriCarb unit (Packard). The measured cpm was converted to dpm using a standard quench series.

Analysis:

The binding parameters were calculated by nonlinear regression in SAS. The program algorithms function analogously to the LIGAND analytical program (Munson, P. J. and Rodbard, D., Analytical Biochem. 107, 220-239 (1980)). The Kd value for $^3$H-AVP for the recombinant hV2 receptors was 2.4 nM, which was used for determining the Ki value.

Oxytocin Receptor Binding Test

Substances:

The test substances were dissolved at a concentration of $10^{-2}$ M in DMSO and diluted with incubation buffer (50 mM tris, 10 mM $MgCl_2$, 0.1% BSA at pH 7.4).

Cell Preparation:

Confluent HEK-293 cells containing transiently expressing recombinant human oxytocin receptors were centrifuged at 750×g for 5 minutes at room temperature. The residue was taken up in ice-cold lysis buffer (50 mM tris-HCl, 10% glycerin at pH 7.4 and Roche Complete Protease Inhibitor), and were subjected to osmotic shock for 20 minutes at 4° C. The lysed cells were then centrifuged at 750×g for 20 minutes at 4° C., the residue was taken up in incubation buffer, and aliquots of $10^7$ cells/mL were prepared. The aliquots were kept frozen at −80° C. until used.

Binding Test:

On the day of the test the cells were thawed, diluted with incubation buffer, and homogenized using a Multipette Combitip (Eppendorf, Hamburg). The reaction assay of 0.250 mL was composed of $2-5 \times 10^4$ recombinant cells, 3-4 nM $^3$H oxytocin (PerkinElmer, NET 858) in the presence of test substance (inhibition curve), or only incubation buffer (total binding). The nonspecific binding was determined using $10^{-6}$ M oxytocin (Bachem AG, H2510). Triplicate determinations were assayed. Bound and free radioligand were separated by vacuum filtration using Wathman GF/B fiberglass filter mats and the Skatron 7000 cell harvester. The bound radioactivity was determined using a Model 2000 or 2200CA TriCarb beta counter unit (Packard).

Analysis:

The binding parameters were calculated by nonlinear regression (SAS), analogously to the LIGAND program of Munson and Rodbard (Analytical Biochem. 1980; 107: 220-239). The Kd value for $^3$H oxytocin for the recombinant hOT receptors was 7.6 nM, which was used for determining the Ki value.

The metabolic stability of the compounds according to the invention was determined in the following test.

Determination of Microsomal Half-Life Value:

The test substances were incubated at a concentration of 0.5:M as follows:

0.5:M test substance together with liver microsomes from various species (0.25 mg protein/mL) in 0.05 M potassium phosphate buffer at pH 7.4 was preincubated in microtiter plates for 5 min at 37° C. The reaction was initiated by adding NADPH (1 mg/mL). Aliquots were withdrawn after 0, 5, 10, 15, 20, and 30 min, and the reaction was terminated and cooled using the same volume of acetonitrile. The samples were kept frozen until the analysis. The half-life value of the compound may be calculated from the decrease in concentration of the compound over time, assuming first-order kinetics.

The invention claimed is:

1. A method for the treatment of at least one condition selected from the group consisting of hypertension, pulmonary hypertension, congestive heart failure, affective disorders, anxiety disorders and/or stress-related anxiety disorders in a patient, and depressive conditions, for the treatment or prevention of stress resulting from withdrawal from one or more of the dependency-causing factors, and/or for the treatment or prevention of stress-induced relapse into the dependencies caused by drugs, medicaments, or other factors, in a patient in need thereof, characterized in that the patient is administered an effective quantity of at least one compound of general formula (I),

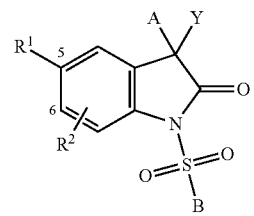

wherein

A is an aromatic, heteroaromatic, partially aromatic, or partially heteroaromatic mono- or bicyclic ring containing 1, 2, 3, 4, 5, 6, 7, 8, 9, or 10 carbon atoms as ring members, and the ring may also contain as ring members 0, 1, 2, 3, or 4 heteroatoms which are the same or different, independently selected from the group consisting of nitrogen, oxygen, and sulfur, and which is substituted with the $R_A{}^1$ radical and which may also be substituted with one, two, or three $R_A{}^{11}$, $R_A{}^{12}$, and/or $R_A{}^{13}$ radicals which, independently of one another and independently of their respective occurrence, are selected from the group consisting of bromine, chlorine, fluorine, CN, $CF_3$, $OCF_3$, $OCHF_2$, OH, O—$C_1$-$C_4$ alkyl, and $C_1$-$C_4$ alkyl;

$R_A{}^1$ is selected from the group consisting of $C_1$-$C_4$ alkylene-$R_A{}^2$, $C_0$-$C_3$ alkylene-O—$C_2$-$C_4$ alkylene-$R_A{}^2$, and $C_0$-$C_3$ alkylene-$NR_A{}^3$—$C_2$-$C_4$ alkylene-$R_A{}^2$;

$R_A{}^3$ is selected from the group consisting of hydrogen and $C_1$-$C_4$ alkyl;

$R_A{}^2$ is selected from the group consisting of OH, $NH_2$, NH($C_1$-$C_4$ alkyl), N($C_1$-$C_4$ alkyl)($C_1$-$C_4$ alkyl), NH($C_2$-$C_4$ alkylene-OH), N($C_1$-$C_4$ alkyl)($C_2$-$C_4$ alkylene-OH), NH($C_2$-$C_4$ alkylene-O—$C_1$-$C_4$ alkyl), N($C_1$-$C_4$ alkyl)($C_2$-$C_4$ alkylene-O—$C_1$-$C_4$ alkyl), NH($C_3$-$C_7$ cyclo alkyl), N($C_1$-$C_4$ alkyl)($C_3$-$C_7$ cyclo alkyl), NH($C_1$-$C_4$ haloalkyl), N($C_1$-$C_4$ alkyl)($C_1$-$C_4$ haloalkyl), and ring $R_A{}^4$;

$R_A{}^4$ independently of its respective occurrence is selected from the group consisting of the particular individual radicals

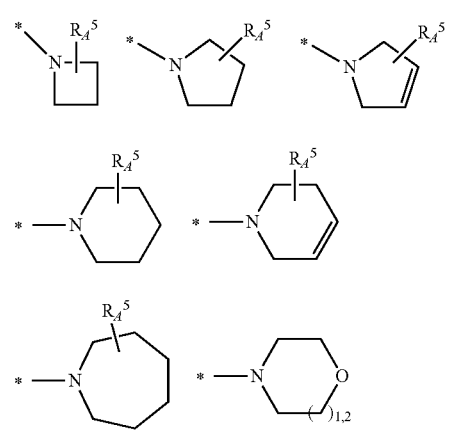

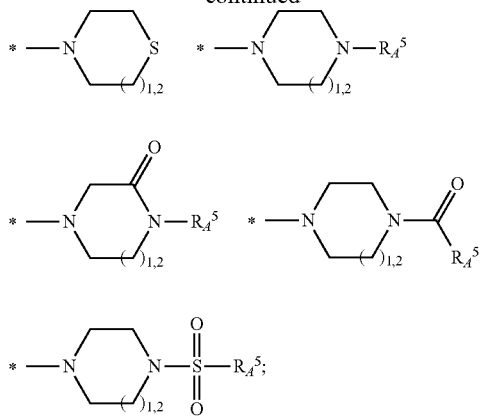

$R_A^5$ is selected from the group consisting of hydrogen, hydroxy, and optionally substituted $C_1$-$C_4$ alkyl;

B is an aromatic, heteroaromatic, partially aromatic, or partially heteroaromatic mono- or bicyclic ring containing 1, 2, 3, 4, 5, 6, 7, 8, 9, or 10 C atoms as ring members, and the ring may also contain as ring members 0, 1, 2, 3, or 4 heteroatoms which are the same or different, independently selected from the group consisting of nitrogen, oxygen, and sulfur, and may be substituted with one, two, or three radicals $R_B^1$, $R_B^2$, and/or $R_B^3$ which, independently of one another and independently of their respective occurrence, are selected from the group consisting of chlorine, bromine, fluorine, CN, $CF_3$, $OCF_3$, $OCHF_2$, OH, O—$C_1$-$C_4$ alkyl, and $C_1$-$C_4$ alkyl;

$R^1$ is selected from the group consisting of hydrogen, bromine, chlorine, fluorine, iodine, CN, $CF_3$, $OCF_3$, $OCHF_2$, O—$C_1$-$C_4$ alkyl, $C_1$-$C_4$ alkyl, $C_2$-$C_4$ alkenyl, and $C_2$-$C_4$ alkynyl;

$R^2$ is selected from the group consisting of hydrogen, $C_1$-$C_4$ alkyl, O—$C_1$-$C_4$ alkyl, chlorine, fluorine, and trifluoromethyl;

Y stands for a radical

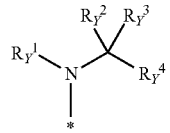

wherein
$R_Y^1$ is selected from the group consisting of hydrogen and $C_1$-$C_4$ alkyl; and
$R_Y^2$ is selected from the group consisting of hydrogen, phenyl, $C_1$-$C_6$ alkyl, and $C_3$-$C_7$ cycloalkyl,
wherein $R_Y^1$ and $R_Y^2$ combined, together with the atom to which they are bonded, may also form a 4-, 5-, 6-, or 7-membered saturated or unsaturated carbocyclic ring containing a nitrogen atom, and the ring may contain one or two substituents $R_Y^6$ and/or $R_Y^7$ which, independently of one another and independently of their respective occurrence, are selected from the group consisting of fluorine, OH, O—$C_1$-$C_4$ alkyl, phenyl, and $C_1$-$C_4$ alkyl; or when $R_Y^6$ and $R_Y^7$ occupy adjacent positions, $R_Y^6$ and $R_Y^7$ together with the respective C atom to which they are bonded may form a condensed substituted or unsubstituted benzene ring;
$R_Y^3$ is selected from the group consisting of hydrogen and methyl;
$R_Y^4$ is a saturated, partially saturated, or unsaturated ring containing 1, 2, 3, 4, 5, or 6 C atoms as ring members, and the ring may also contain as ring members 1, 2, 3, or 4 heteroatoms which are the same or different, independently selected from the group consisting of nitrogen, oxygen, and sulfur, and which may be substituted with one or two radicals $R_Y^8$ and/or $R_Y^9$, where $R_Y^8$ and $R_Y^9$ independently of one another and independently of their respective occurrence are selected from the group consisting of chlorine, bromine, fluorine, CN, OH, O—$C_1$-$C_4$ alkyl, and $C_1$-$C_4$ alkyl; or a physiologically tolerable salt of a compound of general formula (I).

2. The method of claim 1 characterized in that the patient is a mammal.

\* \* \* \* \*